(12) United States Patent
Geiger et al.

(10) Patent No.: US 9,980,942 B2
(45) Date of Patent: May 29, 2018

(54) REJUVENATION OF PRECURSOR CELLS

(71) Applicant: Children's Hospital Medical Center, Cincinnati, OH (US)

(72) Inventors: Hartmut Geiger, Ulm (DE); Maria Carolina Florian, Lonsee (DE); Yi Zheng, Cincinnati, OH (US)

(73) Assignees: CHILDREN'S HOSPITAL MEDICAL CENTER, Cincinnati, OH (US); UNIVERSITAET ULM, Ulm (DE)

( * ) Notice: Subject to any disclaimer, the term of this patent is extended or adjusted under 35 U.S.C. 154(b) by 447 days.

(21) Appl. No.: 14/398,386

(22) PCT Filed: Apr. 30, 2013

(86) PCT No.: PCT/US2013/038912
§ 371 (c)(1),
(2) Date: Oct. 31, 2014

(87) PCT Pub. No.: WO2013/166043
PCT Pub. Date: Nov. 7, 2013

(65) Prior Publication Data
US 2015/0297563 A1 Oct. 22, 2015

Related U.S. Application Data

(60) Provisional application No. 61/641,753, filed on May 2, 2012.

(51) Int. Cl.
*A61K 31/404* (2006.01)
*A61K 31/4985* (2006.01)
*A61K 35/14* (2015.01)
*G01N 33/50* (2006.01)

(52) U.S. Cl.
CPC ........ *A61K 31/404* (2013.01); *A61K 31/4985* (2013.01); *A61K 35/14* (2013.01); *G01N 33/5073* (2013.01); *G01N 2333/914* (2013.01)

(58) Field of Classification Search
None
See application file for complete search history.

(56) References Cited

U.S. PATENT DOCUMENTS

2009/0118310 A1* 5/2009 Nur-E-Kamal ...... A61K 31/519
514/264.11

FOREIGN PATENT DOCUMENTS

WO WO 2009/114725 A2 9/2009

OTHER PUBLICATIONS

Peterson JR et al. 2006. Biochemical Suppression of Small-Molecule Inhibitors: A Strategy to Identify Inhibitor Targets and Signaling Pathway Components. Chem Biol 13: 443-452.*
Florian et al., "Aging Associated Hematopoietic Stem Cell Depolarization Depends on the Rho Family GTPase CDC42," 61. *Mosbacher Kolloquium*, pp. 1-2, Apr. 10, 2010, XP002698971, retrieved from the Internet: URL:http://www.contoo.de/en_US/congress/paper/id/838.
Florian, Maria Carolina, "Impact of Cell Polarity on Hematopoietic Stem Cell Division and Aging," 2011, *Research Grant Program Winning Abstract*, 2011, XP002698970, retrieved from the Internet: URL:http://www.bdbiosciences.com/documents;BD_StemCellGrantWinner2011_MariaFlorian_Abstract.pdf, pp. 1-2.
Florian et al., "Cdc42 Activity Regulates Hematopoietic Stem Cell Aging and Rejuvenation," *Cell Stem Cell* 10, May 4, 2012 © 2012 Elsevier Inc., pp. 520-530.
The International Search Report and Written Opinion dated Sep. 30, 2013 for International Application No. PCT/US2013/038912 which claims priority of U.S. Appl. No. 61/641,753, filed May 2, 2012, and from which captioned U.S. Appl. No. 14/398,386 is a National Stage Entry.

* cited by examiner

*Primary Examiner* — Suzanne M Noakes
*Assistant Examiner* — Stephen M Chong
(74) *Attorney, Agent, or Firm* — Knobbe Martens Olson & Bear LLP

(57) ABSTRACT

The present invention relates generally to methods and pharmaceutical compositions for rejuvenating hematopoietic stem cells and progenitor cells from blood, intestinal tissue and dermal tissue by administration of at least one inhibitor of a GT-Pase, such as Cdc42 GTPase.

18 Claims, 11 Drawing Sheets

REJUVENATION OF PRECURSOR CELLS

STATEMENT REGARDING FEDERALLY SPONSORED R&D

This invention was made with U.S. government support under grant Nos. HL076604 and DK077762 awarded by the National Institutes of Health. The U.S. government has certain rights in the invention.

BACKGROUND

Technical Field

Provided are methods and pharmaceutical compositions for rejuvenating hematopoietic stem cells and progenitor cells from blood, intestinal tissue and dermal tissue by administration of at least one inhibitor of a GTPase, such as Cdc42 GTPase. Also provided are methods and pharmaceutical compositions for reducing weight in an elderly subject by administration of at least one inhibitor of a GTPase, such as Cdc42 GTPase.

Description of the Related Art

Rho family GTPases are molecular switches that control signaling pathways regulating cytoskeleton reorganization, gene expression, cell cycle progression, cell survival, and other cellular processes (Etienne-Manneville, 2002), which is incorporated herein by reference in its entirety.

Rho family proteins constitute one of three major branches of the Ras superfamily. Development of inhibitors of Rho family GTPases may be a promising new avenue for new therapeutic compounds.

SUMMARY

Embodiments disclosed herein relate to methods for rejuvenating a precursor cell in a subject. In specific embodiments, methods and and pharmaceutical compositions are provided for rejuvenating a blood precursor cell, a dermal epithelial precursor cell or an intestinal epithelial precursor cell in a subject, comprising administering to a subject in need of treatment an effective amount of at least one Cdc42-specific inhibitor. In some embodiments, methods and pharmaceutical compositions for reducing weight in an elderly subject by administration of at least one inhibitor of a GTPase, such as Cdc42 GTPase.

In some embodiments, the Cdc42-specific inhibitor is a small molecule. In some embodiments the small molecule comprises a compound of formula (I). In some embodiments, the small molecule is Cdc42 Activity-Specific Inhibitor (CASIN). In the embodiments described herein, the chemical structure of CASIN is:

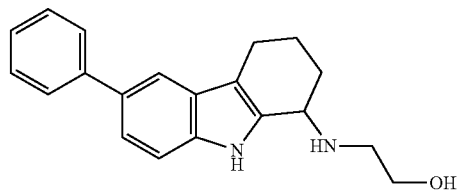 [SMILES: OCCNC1CCCc2c1[nH]c1ccc(-c3ccccc3)cc21]

Also presented herein is a method of reversing Cdc42 apolarity in a hematopoietic stem cell in a subject, the method comprising: administering to a subject in need of treatment an amount of a Cdc42-specific inhibitor that is sufficient to cause polarization of Cdc42 in said cell.

Also presented herein is a method of reversing tubulin apolarity in a hematopoietic stem cell in a subject, the method comprising: administering to a subject in need of treatment an amount of a Cdc42-specific inhibitor that is sufficient to cause polarization of tubulin in said cell.

Also presented herein is a method of restoring elevated Cdc42 activity levels to normal levels in a blood precursor cell or an epithelial precursor cell of a subject in need of such treatment, which method comprises administering to the subject an amount of a Cdc42-specific inhibitor that is sufficient to restore Cdc42 activity to normal levels in said cell.

Also presented herein is a method of restoring the organization and distribution of epithelial cells in the intestinal villi of a subject, the method comprising: administering to a subject in need thereof an amount of a Cdc42-specific inhibitor that is sufficient to cause restoration of the organization and distribution of epithelial cells in the intestinal villi in said subject.

Also presented herein is a method of restoring the activity of epithelial stem cells in the intestinal crypts of a subject, the method comprising: administering to said subject in need thereof an amount of a Cdc42-specific inhibitor that is sufficient to cause restoration of the activity of epithelial stem cells in the intestinal crypts in said subject.

Also presented herein is a method of restoring dermal thickness in a subject, the method comprising: administering to said subject in need thereof an amount of a Cdc42-specific inhibitor that is sufficient to cause restoration of dermal thickness in said subject.

Also presented herein is a method of restoring hair follicle activity in a subject, the method comprising: administering to said subject in need thereof an amount of a Cdc42-specific inhibitor that is sufficient to cause restoration of hair follicle activity in said subject.

Also presented herein is a method of restoring wound healing activity in the dermal tissue of a subject, the method comprising: administering to said subject in need thereof an amount of a Cdc42-specific inhibitor that is sufficient to cause restoration of wound healing activity in the dermal tissue of said subject.

Also presented herein is a method of ex vivo rejuvenating blood precursor cells in an autologous hematopoietic stem cell graft, the method comprising: incubating blood precursor cells that have been isolated from a subject in need thereof with an amount of a Cdc42-specific inhibitor that is sufficient to cause rejuvenation of said isolated blood precursor cells prior to reintroduction to said subject.

Also presented herein is a method of ex vivo rejuvenating blood precursor cells in an allogeneic hematopoietic stem cell graft, the method comprising: incubating blood precursor cells that have been isolated from a subject in need thereof with an amount of a Cdc42-specific inhibitor that is sufficient to cause rejuvenation of said isolated blood precursor cells prior to introduction to a recipient.

Also presented herein is a method of administering rejuvenated blood precursor cells, the method comprising: administering a blood precursor cell that has been isolated and incubated with an amount of a Cdc42-specific inhibitor that is sufficient to cause rejuvenation of said isolated blood precursor cells prior to introduction of said cells to a recipient.

Also presented herein is a method of ex vivo rejuvenating dermal or intestinal epithelial precursor cells, the method comprising: incubating dermal or intestinal epithelial precursor cells that have been isolated from a subject with an amount of a Cdc42-specific inhibitor that is sufficient to cause rejuvenation of said isolated blood precursor cells prior to introduction of said cells to a recipient.

Also presented herein is a pharmaceutical composition for rejuvenation of aging blood precursor cells comprising a Cdc42-specific inhibitor and a pharmaceutically acceptable carrier.

Also presented herein is a pharmaceutical composition for rejuvenation of aging intestinal tissue comprising a Cdc42-specific inhibitor and a pharmaceutically acceptable carrier.

Also presented herein is a pharmaceutical composition for rejuvenation of aging dermal tissue comprising a Cdc42-specific inhibitor and a pharmaceutically acceptable carrier.

Also presented herein is a method of identifying a blood precursor cell, a dermal epithelial precursor cell or an intestinal epithelial precursor cell rejuvenating agent comprising: providing Cdc42 protein or a Cdc42 peptide; providing a target protein or a target peptide that binds the Cdc42 protein or the Cdc42 peptide; providing a compound; and assaying the ability of the compound to inhibit the binding of the Cdc42 protein or the Cdc42 peptide to the target protein or the target peptide, wherein the compound that inhibits the binding rejuvenates progenitor cells but does not mobilize blood precursor cells in a subject at a given dosage.

Also presented herein is a method of identifying a blood precursor cell rejuvenating agent comprising: providing a blood precursor cell; providing a compound; and assaying the ability of the compound to rejuvenate the blood precursor cell. In some embodiments, the blood precursor cell rejuvenating agent rejuvenates the blood precursor cell at a dosage that does not mobilize a blood precursor cell.

Also presented herein is a method of identifying a dermal epithelial precursor cell rejuvenating agent comprising: providing a dermal epithelial precursor cell; providing a compound; and assaying the ability of the compound to rejuvenate the dermal epithelial precursor cell.

Also presented herein is a method of identifying an intestinal epithelial precursor cell rejuvenating agent comprising: providing an intestinal epithelial precursor cell; providing a compound; and assaying the ability of the compound to rejuvenate the intestinal epithelial precursor cell.

Also presented herein is a method for reducing weight in an aged subject comprising: administering to an elderly subject in need of treatment an effective amount of at least one Cdc42-specific inhibitor.

Also presented herein is a method of identifying an agent for weight reduction in an aged subject comprising: providing an an aged non-human subject; providing a compound; and assaying the ability of said compound to reduce the weight of the aged subject.

In any of the embodiments described herein, the methods can further comprise discontinuing exposure of the blood precursor cell, the dermal epithelial precursor cell or the intestinal epithelial precursor cell to the Cdc42-specific inhibitor, wherein the Cdc42-specific inhibitor-mediated change in the blood precursor cell, the dermal epithelial precursor cell or the intestinal epithelial precursor cell is maintained after discontinuing exposure.

In any of the embodiments described herein, said Cdc42-specific inhibitor, said hematopoietic stem cell mobilizing agent, said compound that enhances cancer therapy, said GTPase inhibitor, said inhibitor of Cdc42, said inhibitor of GTPase Cdc42, said GTPase Cdc42 inhibitor, said agent capable of inhibiting GTPase Cdc42, or said agent that specifically inhibits Cdc42 comprises a compound of formula (I):

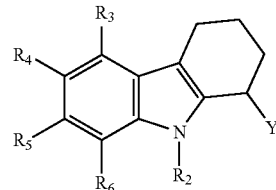

as a single enantiomer, a mixture of enantiomers, pharmaceutically acceptable salt, a solvate, or polymorph thereof, wherein:

Y is selected from the group consisting of $-OR_7$, $-NR_8R_9$, and $-NNR_8R_9$;

$R_7$ is selected from the group consisting of $C_{1-6}$ alkyl, $-(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $-(CH_2)_uC_{3-7}$cycloalkyl, $C_{2-6}$ alkenyl, $C_{1-6}$ alkoxy, hydroxy-$C_{1-6}$ alkyl, phenyl are each optionally substituted with one or more substitutents each independently selected from the group consisting of halo, $-CN$, $-OH$, $C_{1-6}$ alkoxyl, heteroaryl, $R_{19}$, and $-OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of $R_{21}$ and $R_{22}$, each $R_{21}$ is separately selected from the group consisting of halo, cyano, nitro, and hydroxy, each $R_{22}$ is separately selected from the group consisting of $C_{1-6}$ alkyl, $C_{1-6}$ alkoxy $-(CH_2)_uC_{3-7}$cycloalkyl, $C_{2-6}$ alkenyl, hydroxy-$C_{1-6}$ alkyl, $R_{19}$, and $-OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R_2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, $-(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and $-O(CH_2)_u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$ and $R_6$ are each independently selected from the group consisting of hydrogen, halo, cyano, nitro, hydroxy, $C_{1-6}$ alkyl, $(CH_2)_uC_{3-7}$cycloalkyl, $-O(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, —O$(CH_2)_uC_{3-7}$cycloalkyl, $C_{2-6}$ alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, —$(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

DETAILED DESCRIPTION

Figure 1:
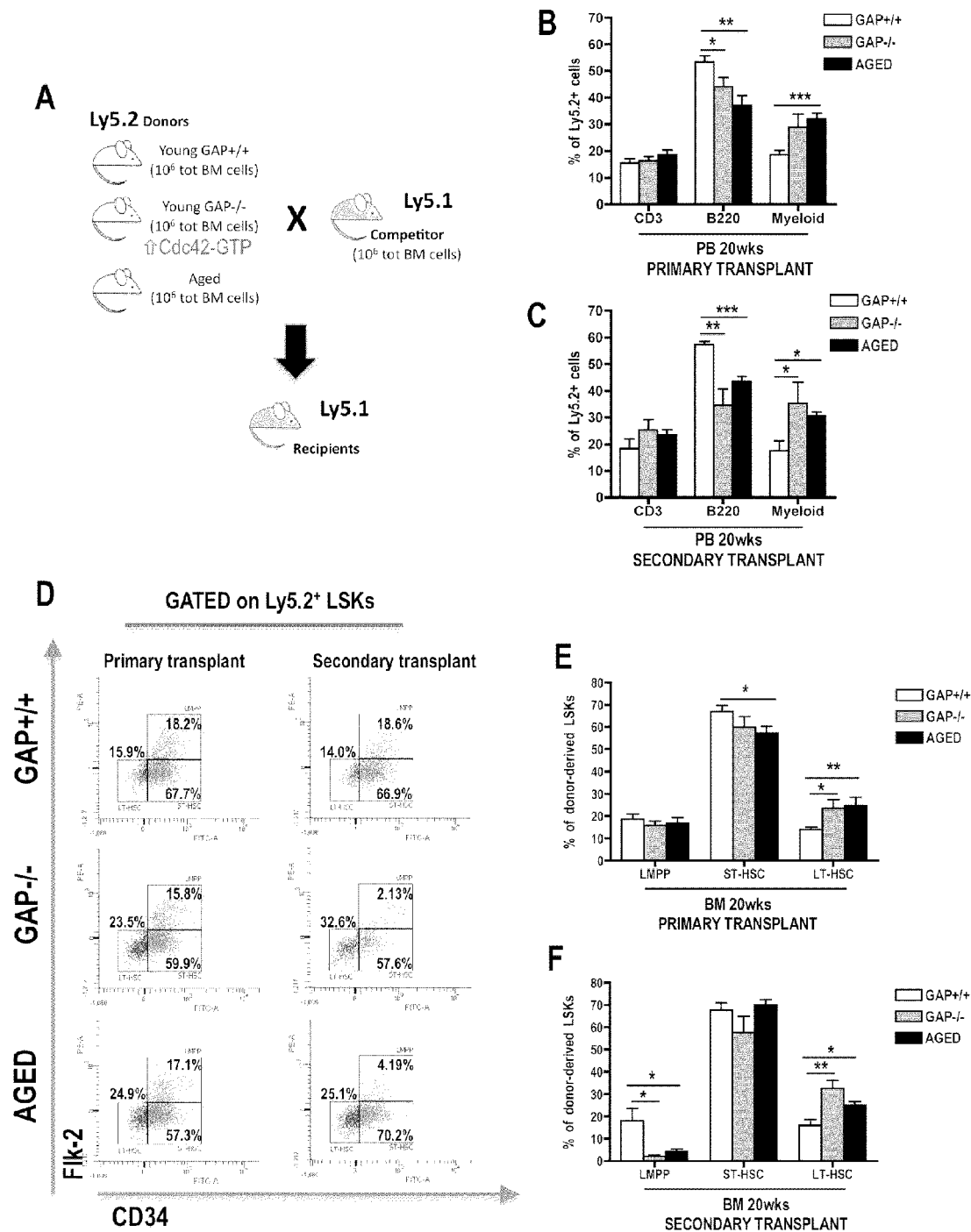
FIG. 1. Constitutively increased Cdc42 activity results in premature aging of young HSCs. (A), Scheme of the experimental set-up for competitive transplant studies. (B-C), Contribution of B-cells, T-cells and myeloid cells among donor-derived Ly5.2$^+$ cells in PB after 20 weeks in competitive primary (B) and secondary (C) transplants. (DF), Representative FACS dot plots (D) and quantitative and statistical analysis of LTHSCs, ST-HSCs and LMPPs distribution among donor-derived LSKs in primary (E) and secondary (F) transplanted mice. * P<0.05,  P<0.01, * P<0.001; columns are mean+1 S.E. The experiment was repeated three times with a cohort of 4 to 5 recipient mice per group (n=14).

Recent developments on molecular and cellular mechanisms of aging have confirmed that the functional decline in hematopoiesis in the elderly, which involves a progressive reduction in the immune response and an increased incidence of myeloid malignancy, is linked to aging of hematopoietic stem cells (HSCs). However, until recently, there was broad consensus that the phenotype of aged HSCs is fixed and dominated by cell-intrinsic regulatory mechanisms that could not be reverted by therapeutic intervention.

Presented herein is the surprising discovery that the elevated activity of the small RhoGTPase Cdc42 in aged precursor cells including HSCs plays a role in causing HSC aging and correlates with apolarity of aged HSCs, and that pharmacological inhibition of Cdc42 activity functionally rejuvenates aged HSCs and increases the percentage of polarized cells among aged HSCs to the level found in young. This discovery consequently implies a novel and critical mechanistic role for Cdc42 activity in HSC aging, identifying Cdc42 activity as a pharmacological target for ameliorating cell intrinsic stem cell aging.

As described herein, it is intended that where a range of values is provided, it is understood that each intervening value, to the tenth of the unit of the lower limit unless the context clearly dictates otherwise, between the upper and lower limit of that range and any other stated or intervening value in that stated range is encompassed within the embodiments. The upper and lower limits of these smaller ranges may independently be included in the smaller ranges is also encompassed within the embodiments, subject to any specifically excluded limit in the stated range. Where the stated range includes one or both of the limits, ranges excluding either both of those included limits are also included in the embodiments.

Unless defined otherwise, all technical and scientific terms used herein have the same meaning as commonly understood by one of ordinary skill in the art to which the embodiments belong. Although any methods and materials similar or equivalent to those described herein may also be used in the practice or testing of the embodiments, the preferred methods and materials are now described. All publications mentioned herein are expressly incorporated by reference in their entireties.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

In some contexts, the terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "heterologous sequence or gene" means a nucleic acid (RNA or DNA) sequence, which is not naturally found in association with the nucleic acid sequences of the specified molecule. The section below provides greater detail on some approaches that can be used to prepare inhibitors of Cdc42.

Methods of Rejuvenating Precursor Cells

Provided herein are methods for rejuvenating a precursor cell in a subject. In specific embodiments, methods are provided for rejuvenating a blood precursor cell, a dermal epithelial precursor cell or an intestinal epithelial precursor cell in a subject. These methods can include administering to a subject in need of treatment an effective amount of at least one Cdc42-specific inhibitor. As used herein, the term "precursor cell" refers to an unspecialized cell that is capable of replicating or self renewing itself and developing into specialized cells of a variety of cell types. Precursor cells as used herein include stem cells, which are pluripotent, and early progenitor cells that are more differentiated than stem cells.

Blood precursor cells include hematopoietic stem cells (HSC), and blood progenitor cells. As used herein in relation to blood precursor cells, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies that can be obtained in culture using known protocols. As used herein, "stem" cells are less differentiated forms of progenitor cells. Typically, hematopoietic stem cells are often positive for CD34 in humans. Some stem cells do not contain this marker, however.

The methods include rejuvenation of epithelial precursor cells and restoration of the function and activity in epithelium. Epithelial cells form the outer surface of the body and line organs, cavities and mucosal surfaces. Epithelial cells include cells from simple epithelium such as squamous epithelial cells, cuboidal epithelial cells, columnar epithelial cells and pseudostratified epithelial cells. Epithelial cells also include cells from stratified epithelium. Accordingly, rejuvenation of epithelial precursor cells can include, for example, epithelial cells of the gingival lining, tongue, palate, oesophagus, stomach, small intestine, large intestine, rectum, anus, gallbladder, thyroid follicles, skin, lactiferous gland ducts, sweat gland ducts, common hepatic duct, common bile duct, pancreatic duct, parotid duct, submaxillary duct, sublingual duct, Bartholin's ducts, ovaries, fallopian tubes, endometrium, endocervix, ectocervix, vagina, labia majora, tubuli recti, rete testis, ductuli efferentes, epidiymis, vas deferens, ejaculatory duct, bulbourethral glands, seminal vesicle, oropharynx, larynx, trachea, respiratory bronchioles, cornea, nose, kidney—proximal convoluted tubule, kidney—ascending thin limb, kidney—distal convoluted tubule, kidney—collecting duct, renal pelvis, ureter, urinary bladder, prostatic urethra, membranous urethra, penile urethra, external urethral orifice, and the like.

Dermal epithelial precursor cells can include dermal or skin regenerative cells. Skin regenerative cells occur in the basal layer of the epidermis and at the base of hair follicles. The epidermal stem cells give rise to keratinocytes, which migrate to the surface of the skin and form a protective layer. The follicular stem cells can give rise to both the hair follicle and to the epidermis. Skin regenerative cells, progenitor cells, and their progeny can be identified using methods and markers known in the art, as exemplified by Cotsarelis et al., Exp. Dermatol. (1999) 8:80-88, which is incorporated by reference in its entirety.

Intestinal epithelial precursor cells can include epithelial stem cells and intestinal progenitor cells. Epithelial stem cells in the lining of the digestive tract occur in deep crypts and give rise to several cell types: absorptive cells, goblet cells, paneth cells, and enteroendocrine cells. Intestinal eplithelial stem cells, progenitor cells, and their progeny can be identified using methods and markers known in the art, as exemplified by Montgomery et al., J. Anat. (2008) 213:52-58, which is incorporated by reference in its entirety.

In some embodiments herein, the methods include administering a Cdc-specific inhibitor to a subject in need of treatment. In some embodiments, a subject in need of treatment can comprise a subject having a population of blood precursor cells, dermal epithelial precursor cells or intestinal epithelial precursor cells that exhibit a phenotype typical of an aging cell. In some embodiments, a subject in need of treatment is an elderly subject, as is understood in the art. For example, the age of the subject can be at least 50%, 55%, 60%, 65%, 70%, 75%, 80%, 85%, 90%, 95or 100% of the life expectancy for that species, or of the life expectancy for that species and gender. For example, the subject in need of treatment can be a human subject older than about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or older than about 80 years old. In some embodiments, the subject in need of treatment is a non-human subject having one or more blood precursor cells, dermal epithelial precursor cells or intestinal epithelial precursor cells that exhibit a phenotype typical of an aging cell. The non-human subject can be elderly, as determined by an equivalent age in comparison to a human life-span. For example, the non-human subject can be a canine subject older than about 8, 9, 10, 11, 12, 13, 14, 15, 16, or older than 17 years old. Similarly, the non-human subject can be a mammalian organism, such as primate, bovine, equine, porcine, ovine, murine, canine or feline. In some embodiments the non-human subject can be a non-mammalian organism, such as avian or zebrafish. In some embodiments, the subject is not elderly, but exhibits a premature phenotype associated with an aging blood precursor cell, a dermal epithelial precursor cell or an intestinal epithelial precursor cell. For example, in some embodiments, the subject is a young subject with a genetic disruption to one or more alleles of the gene encoding the 50RhoGAP protein, which causes premature aging-like phenotypes in multiple tissues and cell types.

As used herein, the terms "aging-like phenotype" and "phenotype typical of an aging cell" and like terms refer to any phenotype of a cell that is typically seen in cells in an elderly subject, but not typically seen in a young subject. Phenotypes typical of an aging cell are known to those of skill in the art, as exemplified by the disclosure of Wang et al., Proc. Natl. Acad. Sci. USA (2007) 104:1248-1253, which is incorporated by reference in its entirety. As one example, phenotypes indicative of an aging hematopoietic precursor cell can include an increase in myeloid cell frequency and a decrease in T cell frequency in peripheral blood, as well as an overall decrease of B-cell frequency and an increase in myeloid cell frequency in bone marrow. As another example, aging hematopoietic progenitor cells can exhibit a reduction in the polar distribution of microtubules in the cell. By way of another example, phenotypes indicative of an aging precursor cell in the intestinal epithelium can include disruption of the distribution and organization of cells along the crypt-villus axis, loss of repair or survival of crypts following irradiation, and apoptotic activity along the crypt-villus axis, as described by Kirkwood, Mech. Ageing Dev. (2004) 12:911-915, which is incorporated by reference in its entirety. As another example, phenotypes indicative of an aging precursor cell in the skin can include impaired epidermal stem cell mobilization and reduced ability to respond to proliferative signals, decreased thickness of the dermal layer, reduced hair follicle distribution and activity, and decreased wound healing, as exemplified by Zouboulis et al., Exp. Gerontol. (2008) 43:986-997, which is incorporated by reference in its entirety.

In some embodiments of the methods provided herein, a Cdc42-specific inhibitor is administered in an amount effective to rejuvenate an aging blood precursor cell, dermal epithelial precursor cell or intestinal epithelial precursor cell. As used herein, "rejuvenate" refers to a full or partial reversal of at least one phenotype typical of an aging cell. In some embodiments, the effective amount of a Cdc42-specific inhibitor that is sufficient to cause rejuvenation of an aging blood precursor cell, dermal epithelial precursor cell or intestinal epithelial precursor cell is less than the amount that is necessary to cause other effects. For example, in some embodiments, an effective amount of a Cdc42-specific inhibitor sufficient to cause rejuvenation of a HSC is less than the amount that causes mobilization of peripheral blood precursor cells from bone marrow into peripheral blood. Methods of determining an effective amount of a Cdc42-specific inhibitor for rejuvenation of an aging blood precursor cell, dermal epithelial precursor cell or intestinal epithelial precursor cell can be performed in accordance with the methods Examples section below, or other methods known in the art, as applied to the teachings provided herein. Thus, provided are methods of administering an amount of Cdc42-specific inhibitor effective to rejuvenate an aging blood precursor cell, dermal epithelial precursor cell or intestinal epithelial precursor cell, but that does not cause mobilization of peripheral blood precursor cells from bone marrow into peripheral blood.

Methodologies and tools for quantifying the degree of aging of precursor cells are known in the art, as described in greater detail hereinbelow. In some embodiments, the aging blood precursor cells, dermal epithelial precursor cells or intestinal epithelial precursor cells are fully rejuvenated with respect to one or more phenotypes typical of an aging cell. In some embodiments, the precursor cells are partially rejuvenated such that a phenotype typical of an aging cell is partially reversed; for example, the phenotype, quantified as described herein or using methods otherwise known in the art, is reduced by at least 25%, 30%, 35%, 40%, 45%, 50%, 55%, 60%, 65%, 70%, 75%, 80%, 85%, 90%, 95% or 99%, in comparison with a normal, non-aged cell.

In some embodiments of the methods provided herein, the Cdc42-specific inhibitor is administered in an amount effective to reduce elevated Cdc42 activity levels to normal levels. As used herein, a normal level of Cdc42 activity is the level of Cdc42 activity in a non-aged cell of the same cell type. As used herein, an elevated level of Cdc42 activity is a level of Cdc42 activity that is greater than that found in a non-aged cell of the same cell type. In some embodiments, the amount of elevated Cdc42 activity can be 1.1 fold, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 4.0 or greater than 4 fold higher than the level Cdc42 activity found in a non-aged or normal cell of the same cell type.

A non-aged or normal can be a cell that does not exhibit a phenotype typical of an aging cell. A non-aged or normal cell can be a cell from a subject early in its life cycle or a cell reflective of a cell from a subject early in its life cycle. A cell from a subject early in its life cycle can be, for example, a cell from a subject at an age that is 0%, 5%, 10%, 15%, 20%, 25%, 30%, 35%, 40%, or 45% of the life expectancy for that species, or of the life expectancy for that species and gender, or any range of ages between the above-indicated values. A cell reflective of a cell from a subject early in its life cycle can be a cell from a different organism of the same species or from the same species or gender, that is 0%, 5%, 10%, 15%, 20%, 25%, 30%, 35%, 40%, or 45% of the life expectancy for that species, or of the life expectancy for that species and gender; or can be a plurality of cells from one or a plurality of different organisms of the same species or from the same species or gender, that is 0%, 5%, 10%, 15%, 20%, 25%, 30%, 35%, 40%, or 45% of the life expectancy for that species, or of the life expectancy for that species and gender; or can be a cell from a cell or tissue culture that is known to behave the same as a cell from the same species or from the same species or gender at an age that is 0%, 5%, 10%, 15%, 20%, 25%, 30%, 35%, 40%, or 45% of the life expectancy for that species, or of the life expectancy for that species and gender.

Methods for measuring relative levels Cdc42 activity are known in the art, and include measuring the relative level of GTP-bound Cdc42 in a cell or cell population. Methods and reagents for measuring the relative level of GTP-bound Cdc42 are known in the art, as exemplified by the Active Cdc42 pull-down and detection kit available from Thermo Fisher Scientific Inc. (Rockford, Ill.), as described in the Example section below, and by the disclosure of Asnaghi et al., Oncogene (2010) 29:2760-2771, which is incorporated by reference in its entirety. In some embodiments, the relative level of GTP-bound Cdc42 in a cell is elevated compared to a non-aged or normal cell, and administration of an effective amount of a Cdc42-specific inhibitor reduces the relative level of GTP-bound Cdc42 in the cell. In some embodiments, an elevated level of GTP-bound Cdc42 is a level that is higher than that found in a non-aged cell, or in a normal cell. The amount of elevated GTP-bound Cdc42 can be 1.1 fold, 1.2, 1.3, 1.4, 1.5, 1.6, 1.7, 1.8, 1.9, 0.0, 2.1, 2.2, 2.3, 2.4, 2.5, 2.6, 2.7, 2.8, 2.9, 3.0, 4.0 or greater than 4 fold higher than the level of GTP-bound Cdc42 found in a non-aged or normal cell.

In some embodiments, administration of a Cdc42-specific inhibitor reduces the relative level of GTP-bound Cdc42 in the cell to a level typically seen in a non-aged or normal cell. In some embodiments, the relative level of GTP-bound Cdc42 is measured as the ratio of GTP-bound Cdc42 to total Cdc42 in a cell. Thus, for example, where the ratio of GTP-bound Cdc42 to total Cdc42 in a non-aged cell is normalized to 1.0, the ratio in an aged cell is greater than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or greater than about 3.0 prior to administering an effective amount of a Cdc42-specific inhibitor.

Figure 3:
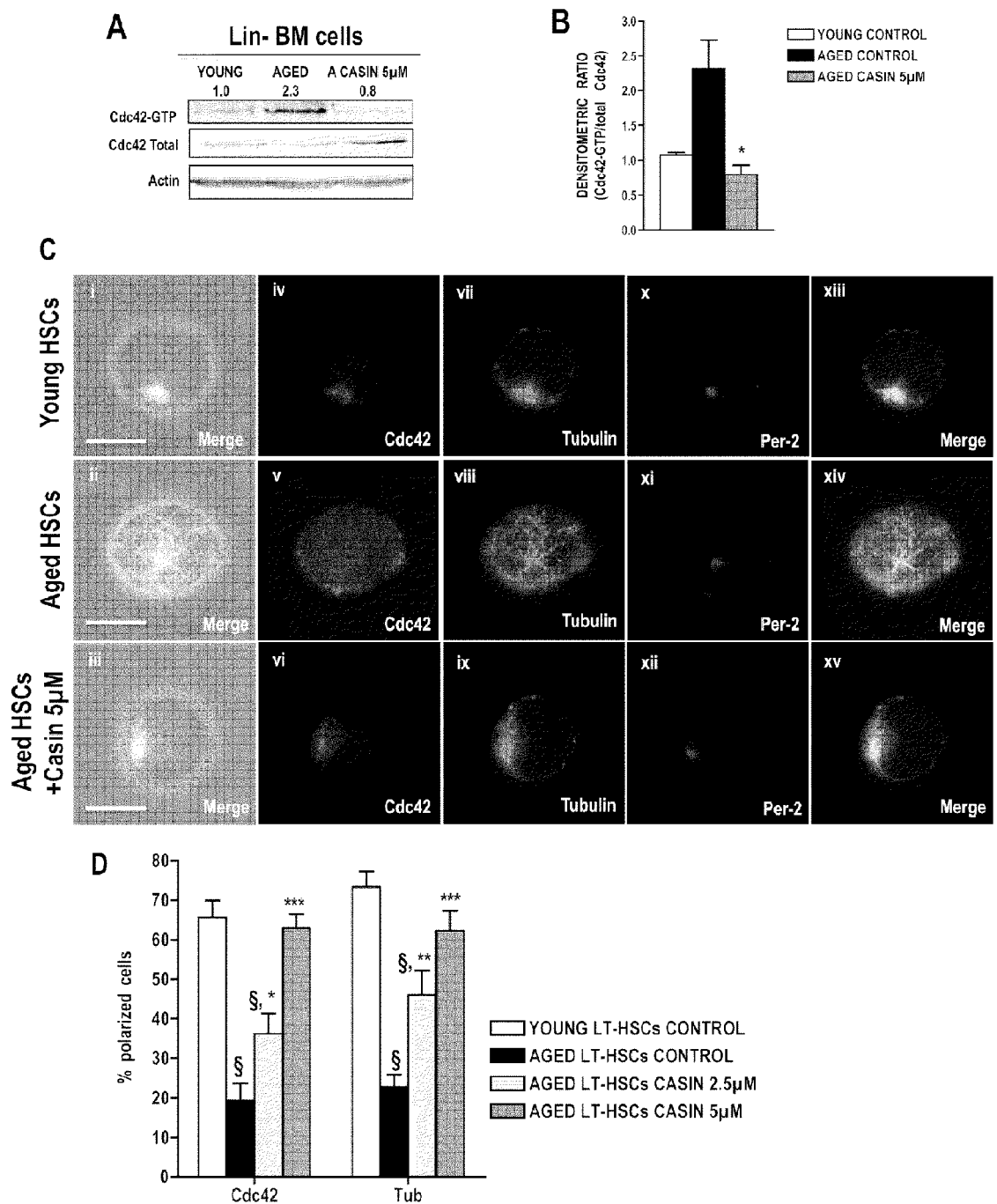
FIG. 3. Pharmacological targeting of Cdc42 reverts aged apolar LT-HSCs to polar cells. (A), Representative Cdc42 activity in young, aged and CASIN (5 μM) treated aged lineage depleted bone marrow (Lin-BM) as determined by a pulldown/Western Blot assay. Active Cdc42 (Cdc42-GTP) was normalized with respect to total Cdc42 and actin as delineated by the numbers. (B), Ratio of the densitometric score of the Cdc42-GTP form and the total Cdc42 expression. Shown are mean+1 S.E., n=3, *P<0.05 vs. aged. (C), Representative distribution of Cdc42, tubulin and Per-2 in young, aged and aged LT-HSCs treated with 5 μM CASIN. Shown are overlaps with the phase contrast picture (panels i-iii) or cells on a dark background (panels iv-xv). Bar=5 μm. (D), Percentages of cells polarized for Cdc42 and tubulin in young, aged and aged LT-HSCs treated with 2.5 and 5 μM CASIN. For each sample cells were singularly analyzed and scored for Cdc42 and tubulin polar distribution. Shown are mean mean+1 S.E., n=4, ~200-300 cells scored per sample in total. § p<0.001 vs young control; * p<0.001 vs. aged control,  p<0.01 vs. aged control, * p<0.05 vs. aged control.
Figure 5:
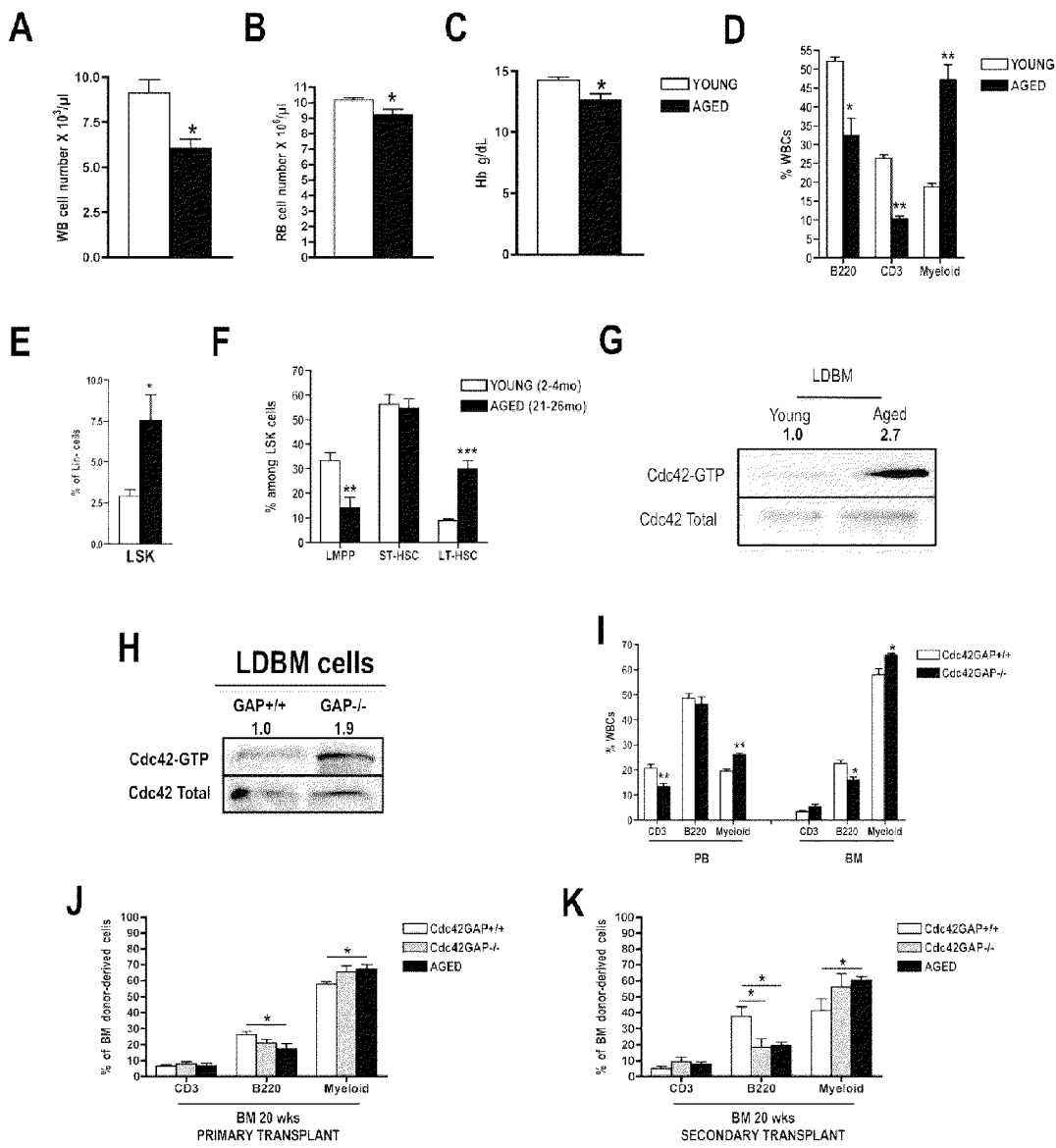
FIG. 5. Hematopoietic parameters in young and aged C57/BL6 mice and young Cdc42GAP−/− mice. (A-D), WB cell count (A), RB cell count (B), hemoglobin dosage (C) and percentage of B220+, CD3+ and myeloid cells among WBCs (D). * P<0.05,  P<0.01, * P<0.001; shown are mean+1 S.E., n=7. (E-F), Percentage of LSKs among Lin_ cells (E) and of LT-HSCs, ST-HSCs and LMPPs distribution among LSKs (F) in BM of young and aged C57/BL6 mice. * P<0.05,  P<0.01, * P<0.001; shown are mean+1 SEM. (G) Representative Cdc42 activity in young, aged hematopoietic progenitor cells (LDBM) as determined by a pulldown/Western Blot assay. Active Cdc42 (Cdc42-GTP) was normalized with respect to total Cdc42. Numbers indicate ratio of the densitometric score of the Cdc42-GTP form and the total Cdc42 expression. (H) Representative Cdc42 activity in young Cdc42GAP+/+ and Cdc42GAP−/− hematopoietic progenitor cells (LDBM) as determined by a pulldown/Western Blot assay. Active Cdc42 (Cdc42-GTP) was normalized with respect to total Cdc42. Numbers indicate ratio of the densitometric score of the Cdc42-GTP form and the total Cdc42 expression. (I) Percentage of $B220_+$, $CD3_+$ and myeloid cells among WBCs in PB and among BM cells in $Cdc42GAP_{+/+}$ and $Cdc42GAP_{-/-}$ mice. (J-K) Percentage of $B220_+$, $CD3_+$ and myeloid cells among donor-derived Ly5.2$^+$ cells in BM 20 weeks post primary (J) and secondary (K) transplant. * P<0.05; shown are mean values+1 S.E. The experiment was performed three times with a cohort of 3 to 5 recipient mice per group (n=14).

In some embodiments, administration of an effective amount of a Cdc42-specific inhibitor is sufficient to bring the relative level of GTP-bound Cdc42 back to about the same relative level of GTP-bound Cdc42 in a non-aged cell. Thus, in some embodiments, administration of an effective amount of a Cdc42-specific inhibitor modulates the ratio of GTP-bound Cdc42 to total Cdc42 in an aged cell from an elevated level back to a level of about 0.8, 0.9, 1.0, 1.1 or 1.2 or more, when normalized to a non-aged cell. For example, as seen in FIG. 3A and in FIGS. 5G-H presented herein, GTP-bound Cdc42 levels relative to total Cdc42 are measured by pull-down/Western Blot assay and compared as a ratio to the levels observed in non-aged or young cells.

In some embodiments, administration of an effective amount of a Cdc42-specific inhibitor is sufficient to reduce the relative level of GTP-bound Cdc42 in an aged cell. Thus, in some embodiments, administration of an effective amount of a Cdc42-specific inhibitor reduces the ratio of GTP-bound Cdc42 to total Cdc42 in an aged cell from an elevated level to a level of greater than about 0.8 and less than about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or less than about 3.0, when normalized to a non-aged cell, after administering the inhibitor.

In some embodiments, a population of cells in the subject in need of treatment have elevated levels of GTP-bound Cdc42. In some embodiments, at least 10%, 20%, 30%, 40%, 50%, 60%, 70%, 80%, or at least 90% of contacted blood precursor cells have elevated Cdc42 activity levels prior to administering the Cdc42-specific inhibitor. In some embodiments, at least 10%, 20%, 30%, 40%, 50%, 60%, 70%, 80%, or at least 90% of contacted skin epithelial precursor cells have elevated Cdc42 activity levels prior to administering the Cdc42-specific inhibitor. In some embodiments, at least 10%, 20%, 30%, 40%, 50%, 60%, 70%, 80%, or at least 90% of contacted intestinal epithelial precursor cells have elevated Cdc42 activity levels prior to administering the Cdc42-specific inhibitor.

Methods of Reversing Apolarity

Also presented herein are methods of reversing apolarity in a hematopoietic stem cell in a subject. The methods can comprise administering to a subject in need of treatment an amount of a Cdc42-specific inhibitor that is sufficient to reverse apolarity in the cell. As used herein, the term "apolarity" refers to a partial or full loss of a polarized phenotype in a cell. As used herein, the terms "reversing apolarity" and "restoration of polarity" refers to a partial or full restoration of a polarized phenotype in a cell. While not intending to be limited to the following, it is postulated that the age associated loss of germ-line stem cell function correlates with loss of cell polarity, as exemplified by a reduction in the frequency of cells with a polar distribution of microtubules among aged early hematopoietic progenitor cells. As such, a restoration of polarity includes fully or partially increasing the proportion of polarized cells in a population of cells. In some embodiments, a restoration of polarity includes increasing the proportion of polarized cells in a population of cells to a level that is some percentage of the proportion of polarized cells in a population of non-aged cells of the same cell type. Thus, as one example, where a 65% of a population of non-aged cells are polarized, and 20% of a population of aged cells are polarized, the methods provided herein can comprise increasing the population of polarized aged cells to a population where 25%, 30%, 35%, 40%, 45%, 50%, 55%, 60%, 65%, 70%, 75%, 80%, 85%, 90%, 95% or 100% of the contacted aged cells are polarized. In some embodiments, the amount of a Cdc42-specific inhibitor that is sufficient to reverse apolarity in the cell is an amount that is less than or equivalent to the amount that is sufficient to reduce GTP-bound Cdc42 levels in an aged HSC to the about the levels of GTP-bound Cdc42 in a normal, non-aged HSC, as described in greater detail hereinabove.

Methods of analyzing and measuring polarity of a cell are known in the art. For example, as described in the Example section below, cell polarity can be scored by staining cells using an antibody specific for a marker of cell polarity and then determining whether the localization of the stained marker has an asymmetric distribution, for example, by drawing a line across the middle of the cell and evaluating asymmetry with respect to the line. It will be appreciated that any suitable quantitative or qualitative method known in the art for determining polarization in a cell can be used in the methods provided herein.

Any one of a number of markers of cell polarity known in the art can be analyzed for loss of polarized microtubule distribution in a cell. For example, as set forth in the Example section below, markers such as Cdc42 and tubulin are asymmetrically distributed in young HSCs, but not in aged cells. Other markers of cell polarity include, but are not limited to, gp135, Crumbs, Stardust, Par6, Par3, Dlg, Scribble, Lg1 and similar markers, as are known in the art and as exemplified by P. Humbert et al., Trends Cell Biol. (2006) 16:622-630, incorporated herein by reference in its entirety. Accordingly, the methods provided herein can include a method of reversing Cdc42 apolarity in a hematopoietic stem cell in a subject, the method comprising: administering to a subject in need of treatment an amount of a Cdc42-specific inhibitor that is sufficient to cause polarization of Cdc42 in the cell. The methods provided herein can also include a method of reversing tubulin apolarity in a hematopoietic stem cell in a subject, the method comprising: administering to a subject in need of treatment an amount of a Cdc42-specific inhibitor that is sufficient to cause polarization of tubulin in the cell.

Methods of Rejuvenating Intestinal Epithelium

Also presented herein are methods of rejuvenating the intestinal epithelium of a subject. As used herein, rejuvenating the intestinal epithelium of a subject refers to partially or fully restoring the organization, distribution and activity of epithelial cells in the intestinal epithelium to levels seen in normal, non-aged cells of the same cell type. Organization and distribution of epithelial cells refers to the three-dimensional architecture of intestinal villi. The intestinal epithelium has a well-defined architecture where proliferation and differentiation take place along organized structures. As is known in the art, the organization and distribution of the intestinal epithelium can be evaluated and quantified by any one of a number of methods, including measuring apoptotic activity along the crypt-villus axis, measuring proliferation activity along the crypt-villus axis, and quantifying the differentiation activity of cells into the various epithelial cell progeny along the crypt-villus axis, as exemplified, for example, by Kirkwood, Mech. Ageing Dev. (2004) 12:911-915, which is incorporated by reference in its entirety. In embodiments where apoptotic activity is quantified, the methods can include restoring an aged intestinal villus to one having 25%, 30%, 35%, 40%, 45%, 50%, 55%, 60%, 65%, 70%, 75%, 80%, 85%, 90%, 95% or 100% of the apoptotic activity in an equivalent intestinal villus in a normal, non-aged subject. An equivalent intestinal villus can be a villus from the equivalent location along the intestinal tract, such as duodenum, jejunum, colon, and the like. A normal, non-aged intestinal villus can be a collection of normal, non-aged cells or cells representative of normal, non-aged cells, as described above. In embodiments where proliferative activity is quantified, the methods can include restoring an aged intestinal villus to one having 25%, 30%, 35%, 40%, 45%, 50%, 55%, 60%, 65%, 70%, 75%, 80%, 85%, 90%, 95% or 100% of the proliferative activity in an equivalent intestinal villus in a normal, non-aged subject. In embodiments where differentiation activity is quantified, the methods can include restoring an aged intestinal villus to one having 25%, 30%, 35%, 40%, 45%, 50%, 55%, 60%, 65%, 70%, 75%, 80%, 85%, 90%, 95% or 100% of the differentiation activity in an equivalent intestinal villus in a normal, non-aged subject.

Thus, in some embodiments are presented methods of restoring the organization and distribution of epithelial cells in the intestinal villi of a subject. The method can comprise administering to a subject in need thereof an amount of a Cdc42-specific inhibitor that is sufficient to cause restoration of the organization and distribution of epithelial cells in the intestinal villi in the subject. In some embodiments, the amount of a Cdc42-specific inhibitor that is sufficient to cause restoration of the organization and distribution of epithelial cells in the intestinal villi is an amount that is less than or equivalent to the amount that is sufficient to reduce GTP-bound Cdc42 levels in an aged epithelial stem cell to the about the levels of GTP-bound Cdc42 in a normal, non-aged epithelial stem cell, as described in greater detail hereinabove.

Also presented herein are methods of restoring the activity of epithelial stem cells in the intestinal crypts of a subject, the method comprising: administering to a subject in need thereof an amount of a Cdc42-specific inhibitor that is sufficient to cause restoration of the activity of epithelial stem cells in the intestinal crypts in said subject. In some embodiments, the amount of a Cdc42-specific inhibitor that is sufficient to cause restoration of the activity of epithelial stem cells is an amount that is less than or equivalent to the amount that is sufficient to reduce GTP-bound Cdc42 levels in an aged epithelial stem cell to about the levels of GTP-bound Cdc42 in a normal, non-aged epithelial stem cell, as described in greater detail hereinabove. As used herein, restoration of the activity of intestinal epithelial stem cells refers to partially or fully restoring the activity of intestinal epithelial stem cells to levels seen in normal, non-aged cells of the same cell type. Method for measuring and quantifying the activity of intestinal epithelial stem cells are well-known in the art, and can include direct markers of activity or indirect markers. Direct markers include measures of the number of stem cells per crypt and the proliferative activity of those stem cells, and can be quantified using known markers and methods, as exemplified by Montgomery et al., J. Anat. (2008) 213:52-58, which is incorporated by reference in its entirety. Indirect markers of stem cell can include measurement of progeny cell differentiation, proliferation and apoptosis as described above. Accordingly, in some embodiments where stem cell activity is quantified, the methods can include restoring stem cell activity in an aged villus to 25%, 30%, 35%, 40%, 45%, 50%, 55%, 60%, 65%, 70%, 75%, 80%, 85%, 90%, 95% or 100% of the stem cell activity in an equivalent intestinal villus in a normal, non-aged subject.

Methods of Rejuvenating Dermal Epithelium

Also presented herein are methods of rejuvenating the dermal epithelium of a subject. As used herein, rejuvenating the dermal epithelium of a subject refers to partially or fully restoring the activity of epithelial cells in the dermal epithelium to levels seen in normal, non-aged cells of the same cell type. Cellular regeneration of skin epidermis and hair follicles is maintained along lifespan of individuals by different adult stem/progenitor cell subpopulations localized within the specialized microenvironments, niches in basal layer of epidermis, sebaceous gland and hair follicle bulge region. These small subpopulations of immature cells endowed with a high self-renewal capacity and multilineage differentiation ability contribute to replenish the different skin cell lineages, including mature and specialized keratinocytes, sebocytes or melanocytes, in homeostatic conditions or after intense skin injuries. The activity of cells in the epidermis, sebaceous gland and hair follicle are dependent upon the activity, stress-resistance and survival of skin regenerative cells. Thus, in some embodiments, the methods provided herein allow for restoring the activity of skin regenerative cells which can be measured by thickness of the dermis and/or epidermis, activity of hair follicles, and would healing activity.

Accordingly, in some embodiments a method is provided for restoring dermal thickness in a subject, the method comprising: administering to the subject in need thereof an amount of a Cdc42-specific inhibitor that is sufficient to cause restoration of dermal thickness in the subject. Any one of a number of methodologies for quantifying dermal thickness known in the art can be used in the methods provided herein, including visual and/or microscopic quantification of skin thickness, high frequency ultrasound measurement, and mechanical tools such as caliper instrumentation, as exemplified by Kaloudi et al, Ann. Rheum. Dis. (2010) 69:1140-1143, incorporated herein by reference in its entirety. In embodiments where thickness of the dermis and/or epidermis is quantified, the methods can include restoring thickness of the dermis and/or epidermis in an aged subject to 25%, 30%, 35%, 40%, 45%, 50%, 55%, 60%, 65%, 70%, 75%, 80%, 85%, 90%, 95% or 100% of the thickness of the dermis and/or epidermis in a normal, non-aged subject. In some embodiments, the amount of a Cdc42-specific inhibitor that is sufficient to cause restoration of dermal thickness is an amount that is less than or equivalent to the amount that is sufficient to reduce GTP-bound Cdc42 levels in an aged skin regenerative cell to the about the levels of GTP-bound Cdc42 in a normal, non-aged skin regenerative cell, as described in greater detail hereinabove.

In some embodiments a method is provided for restoring hair follicle activity in a subject, the method comprising: administering to the subject in need thereof an amount of a Cdc42-specific inhibitor that is sufficient to cause restoration of hair follicle activity in the subject. As used herein, hair follicle activity refers generally to the individual activities of hair follicle formation, hair follicle regeneration and hair shaft production activity. In embodiments where hair follicle activity is quantified, the methods can include restoring hair follicle activity of the dermis and/or epidermis in an aged subject to 25%, 30%, 35%, 40%, 45%, 50%, 55%, 60%, 65%, 70%, 75%, 80%, 85%, 90%, 95% or 100% of the hair follicle activity in a normal, non-aged subject. Any one of a number of methodologies for quantifying hair follicle activity known in the art can be used in the methods provided herein, including visual and/or histochemical quantification of hair follicle formation, hair follicle regeneration and hair shaft production activity, as exemplified by Ito et al., Nature (2007) 447:316-320, incorporated herein by reference in its entirety. These methodologies can include quantification of markers of hair follicle activity such as gamma-glutamyl transpeptidase, as exemplified by Kawabe et al., J. Invest. Dermatol. (1994) 103:122-126; incorporated herein by reference in its entirety. In some embodiments, the amount of a Cdc42-specific inhibitor that is sufficient to cause restoration of hair follicle activity is an amount that is less than or equivalent to the amount that is sufficient to reduce GTP-bound Cdc42 levels in an aged skin regenerative cell to the about the levels of GTP-bound Cdc42 in a normal, non-aged skin regenerative cell, as described in greater detail hereinabove.

In some embodiments a method is provided for restoring wound healing activity in a subject, the method comprising: administering to the subject in need thereof an amount of a Cdc42-specific inhibitor that is sufficient to cause restoration of wound healing activity in the subject. Wound healing activity in a subject can be quantified using any of a number of techniques known in the art, as exemplified by Levy et al., Dermatology (1995) 190:136-141; incorporated herein by reference in its entirety. In embodiments where wound healing activity is quantified, the methods can include restoring wound healing activity of the dermis and/or epidermis in an aged subject to 25%, 30%, 35%, 40%, 45%, 50%, 55%, 60%, 65%, 70%, 75%, 80%, 85%, 90%, 95% or 100% of the wound healing activity in a normal, non-aged subject. In some embodiments, the amount of a Cdc42-specific inhibitor that is sufficient to cause restoration of wound healing activity is an amount that is less than or equivalent to the amount that is sufficient to reduce GTP-bound Cdc42 levels in an aged skin regenerative cell to the about the levels of GTP-bound Cdc42 in a normal, non-aged skin regenerative cell, as described in greater detail hereinabove.

Methods of Reducing Weight

In some embodiments, methods and pharmaceutical compositions for reducing weight in an elderly subject by administration of at least one inhibitor of a GTPase, such as Cdc42 GTPase. Also provided are methods for reducing weight gain in an elderly subject by administration of at least one inhibitor of a GTPase, such as Cdc42 GTPase. Such methods can include administering to an elderly subject in need of treatment an effective amount of at least one Cdc42-specific inhibitor. Such methods can include administering to an elderly subject in need of treatment an effective amount of at least one Cdc42-specific inhibitor. In some such methods, the subject is overweight, obese or morbidly obese. Classification of overweight, obese or morbidly obese would be in accordance with the standard methods used by a qualified clinician.

The inventors have found that administering to an elderly subject an effective amount of at least one Cdc42-specific inhibitor can lead to a weight reduction in the subject. Thus, as provided herein, Cdc42-specific inhibitor can be effective to reduce the level of weight gain in a subject or to reduce the subject's weight. In some embodiments, the level of weight gain in the subject is reduced by at least or at least about 25%, 30%, 35%, 40%, 45%, 50%, 55%, 60%, 65%, 70%, 75%, 80%, 85%, 90%, 95% or 100% of the weight the subject would have gained in the absence of administration of the Cdc42-specific inhibitor. In some embodiments, the subject's weight is stabilized within a range of +5% to −5% of the subject's weight. Methods for reduction of weight gain or stabilization of weight are typically directed to subjects with a history of weight gain or with a health condition, such, for example, as diabetes, that is associated with weight gain. In some embodiments, the subject's weight is reduced. In some such embodiments, the weight of the subject is reduced by at least, at least about, up to, or up to about 0.5%, 1%, 2%, 3%, 4%, 5%, 6%, 7%, 8%, 9%, 10%, 15%, 20%, 25%, 30%, or 35%, or a range in between any of the aforementioned numbers.

Ex Vivo Methods of Rejuvenating Precursor Cells

Also presented herein are methods of ex vivo rejuvenating precursor cells. Methods of ex vivo rejuvenation can be useful where precursor cells from subject have a probability of exhibiting one or more phenotypes typical of an aging cell, and where it is desirable to partially or fully reverse the one or more phenotypes typical of an aging cell prior to further manipulation and/or transplantation of the precursor cells. In some embodiments, the cells are ex vivo rejuvenated prior to reintroduction of the cells to the same subject (i.e., autologous transplantation). In some embodiments, the cells are ex vivo rejuvenated prior to reintroduction of the cells to a different subject (i.e., allogeneic transplantation). In some embodiments, the methods comprise incubating precursor cells that have been isolated from a donor subject in need thereof with an amount of a Cdc42-specific inhibitor that is sufficient to cause rejuvenation of said isolated blood precursor cells prior to reintroduction to the same or a separate subject.

In one embodiment, a method is provided for ex vivo rejuvenating blood precursor cells in an autologous hematopoietic stem cell graft, the method comprising: incubating blood precursor cells that have been isolated from a subject in need thereof with an amount of a Cdc42-specific inhibitor that is sufficient to cause rejuvenation of said isolated blood precursor cells prior to reintroduction to the subject.

In one embodiment, a method is provided for ex vivo rejuvenating blood precursor cells in an allogeneic hematopoietic stem cell graft, the method comprising: incubating blood precursor cells that have been isolated from a subject in need thereof with an amount of a Cdc42-specific inhibitor that is sufficient to cause rejuvenation of said isolated blood precursor cells prior to introduction to a recipient.

In one embodiment, a method is provided for administering rejuvenated blood precursor cells, the method comprising: administering a blood precursor cell that has been isolated and incubated with an amount of a Cdc42-specific inhibitor that is sufficient to cause rejuvenation of said isolated blood precursor cells prior to introduction of said cells to a recipient.

In one embodiment, a method is provided for ex vivo rejuvenating dermal or intestinal epithelial precursor cells, the method comprising: incubating dermal or intestinal epithelial precursor cells that have been isolated from a subject with an amount of a Cdc42-specific inhibitor that is sufficient to cause rejuvenation of said isolated blood precursor cells prior to introduction of said cells to a recipient.

In some embodiments, the rejuvenation comprises partially or fully reversing one or more phenotypes typical of an aging cell prior to further manipulation and/or transplantation of the precursor cells. Methodologies and tools for quantifying phenotypes typical of an aging cell in view of the teachings herein are known in the art, as described in greater detail hereinbelow. In some embodiments, one or more phenotypes typical of an aging blood precursor cell, dermal epithelial precursor cell or intestinal epithelial precursor cell are fully reversed. In some embodiments, the precursor one or more phenotypes typical of an aging blood precursor cell, dermal epithelial precursor cell or intestinal epithelial precursor cell are partially reversed; for example, the phenotype, quantified as described herein, is reduced by at least 25%, 30%, 35%, 40%, 45%, 50%, 55%, 60%, 65%, 70%, 75%, 80%, 85%, 90%, 95% or 99%, in comparison with a normal, non-aged cell.

In some embodiments, the amount of a Cdc42-specific inhibitor that is sufficient to cause rejuvenation of said isolated precursor cells prior to reintroduction to the same or a separate subject is an amount that is less than or equivalent to the amount that is sufficient to reduce GTP-bound Cdc42 levels in an aged precursor cell to the about the levels of GTP-bound Cdc42 in a normal, non-aged precursor cell, as described in greater detail hereinabove.

Long-term Effects

Presented herein is the discovery that treatment of a subject with a Cdc42-specific inhibitor to rejuvenate a blood precursor cell, a dermal epithelial precursor cell or an intestinal epithelial precursor cell can be performed transiently and the rejuvenating effect of the treatment can be maintained long after the treatment with the Cdc42-specific inhibitor. Accordingly, provided herein are methods of rejuvenating a blood precursor cell, dermal epithelial precursor cell or intestinal epithelial precursor cell, further comprising discontinuing exposure of the blood precursor cell, the dermal epithelial precursor cell or the intestinal epithelial precursor cell to the Cdc42-specific inhibitor, wherein the Cdc42-specific inhibitor-mediated change in the blood precursor cell, the dermal epithelial precursor cell or the intestinal epithelial precursor cell is maintained after discontinuing exposure. In some embodiments, the inhibitor-mediated change is maintained for 1, 2, 3, 4, 5, 6, 7, 8, 9, 10, 11, 12, 13, 14, 15, 16, 17, 18, 19, 20, 21 days or longer, 3, 4, 5, 6, 7, 8, 9, 10, 11, 12, 13, 14, 15, 16 weeks or longer, 2, 3, 4, 5, 6, 7, 8, 9, 10, 11, 12, 13, 14, 15, 16, 17, 18, 19, 20, 21, 22, 23, 24 months or longer re, or 2, 3, 4, 5, 6, 7, 8, 9, 10, 11, 12 years or longer after discontinuing exposure to the Cdc42-specific inhibitor. For example, as set forth in the Example section below, inhibitor-mediated restoration of cell polarity can be maintained in blood precursor cells for weeks or longer after discontinuing exposure to the Cdc42-specific inhibitor. As a further example, as set forth in the Example section below, inhibitor-mediated restoration of the structure, organization and distribution of epithelial cells in the intestinal villus can be maintained for weeks or longer after discontinuing exposure to the Cdc42-specific inhibitor. As a further example, as set forth in the Example section below, inhibitor-mediated restoration of the structure, organization and distribution of epithelial cells in the skin can be maintained for weeks or longer after discontinuing exposure to the Cdc42-specific inhibitor.

Pharmaceutical Compositions

Also provided herein are pharmaceutical compositions for the methods provided herein, including methods of rejuvenation of aging blood precursor cells, aging intestinal tissue and aging dermal tissue. In some embodiments, the pharmaceutical compositions comprise a Cdc42-specific inhibitor and a pharmaceutically acceptable carrier. In some embodiments where the pharmaceutical composition is for rejuvenation of aging dermal tissue, the composition can comprise, for example a topical formulation. In some embodiments, the topical formulation is a non-transdermal composition, formulated so as to not penetrate beyond the dermal layer. Non-transdermal formulations are known in the art, and include matrical or micellar solutions, bandages, wound dressings, aerosol sprays, foams, non-transdermal topical patches, topical administrative agents and the like.

In some embodiments, the pharmaceutical composition comprises a Cdc42-specific inhibitor in a dosage formulated in an amount that is less than or equivalent to the amount that is sufficient to reduce GTP-bound Cdc42 levels in an aged precursor cell to the about the levels of GTP-bound Cdc42 in a normal, non-aged precursor cell, as described in greater detail hereinabove. In some embodiments, the pharmaceutical composition comprises a Cdc42-specific inhibitor in a dosage formulated in an amount that is less than the amount that is sufficient to mobilize hematopoietic stem cells and progenitor cells from bone marrow into peripheral blood.

Cdc42-specific Modulators and Inhibitors

Embodiments disclosed herein relate to compounds, compositions, pharmaceutical compositions, methods, uses, and kits that comprise at least one Cdc42-specific inhibitor. In some embodiments, the Cdc42-specific inhibitor can be a chemical inhibitor such as a small molecule (e.g., CASIN). Small molecules include, for example, chemical molecules with a low molecular weight (e.g. a molecular weight below 2000 daltons). Additionally, the Cdc42-specific inhibitor can be an siRNA molecule, an antisense molecule, a small RNA (e.g., a micro RNA) or modified nucleic acid, a ribozyme, an antibody (such as a neutralizing antibody), or a polypeptide (e.g., a dominant negative peptide). Any type of inhibitor which is known to one of skill in the art may be used.

Another aspect of the preferred embodiments relates to the regulation of biological pathways in which a GTPase is involved, particularly pathological conditions, e.g., aging of hematopoietic cells, intestinal epithelial cells and dermal epithelial cells. Thus, the preferred embodiments relate to all aspects of a method of modulating an activity of a Cdc42 GTPase comprising, administering an effective amount of an active agent, an effective amount of a compound which specifically and/or selectively modulates the activity of a Cdc42 GTPase, or combination thereof. The activity of Cdc42 which is modulated can include: GTP binding, GDP binding, GEF binding, GTPase activity, integrin binding, coupling or binding of Cdc42 to receptor or effector-like molecules (such as integrins, growth factor receptors, tyrosine kinases, PI-3K, PIP-5K, etc.). Increasing, reducing, antagonizing, or promoting Cdc42 can modulate the activity. The modulation of Cdc42 can be measured by assay for GTP hydrolysis, binding to GEF, etc. An effective amount is any amount which, when administered, modulates the Cdc42 activity. The activity can be modulated in a cell, a tissue, a whole organism, in situ, in vitro (test tube, a solid support, etc.), in vivo, or in any desired environment.

Other assays for Cdc42-mediated signal transduction can be accomplished according to procedures known in the art, e.g., as described in U.S. Pat. Nos. 5,141,851; 5,420,334; 5,436,128; and 5,482,954, all of which are incorporated herein by reference in their entirety where permitted. In addition, peptides that inhibit the interaction, e.g., binding, between an active agent and a G-protein, such as Cdc42, can be identified.

Also presented herein is a method of identifying a blood precursor cell, a dermal epithelial precursor cell or an intestinal epithelial precursor cell rejuvenating agent. In some embodiments, the method comprises: providing Cdc42 protein or a Cdc42 peptide; providing a target protein or a target peptide that binds the Cdc42 protein or the Cdc42 peptide; providing a compound; and assaying the ability of the compound to inhibit the binding of the Cdc42 protein or the Cdc42 peptide to the target protein or the target peptide, wherein the compound that inhibits the binding rejuvenates progenitor cells but does not mobilize blood precursor cells in a subject at a given dosage. Methods for detecting inhibition of Cdc42 activity are known in the art, as exemplified by the Active Cdc42 pull-down and detection kit available from Thermo Fisher Scientific Inc. (Rockford, Ill.), as described in the Example section below, and by the incorporated materials of Asnaghi et al., Oncogene (2010) 29:2760-2771. In some embodiments, the method includes comparing the inhibitory properties of a compound being tested to the inhibitory properties of one or more reference compounds. Such a reference compound can be, for example, CASIN or other compounds described herein.

The preferred embodiments also relate to a method of testing for and identifying an agent which modulates the activity of Cdc42 GTPase, or a biologically-active fragment thereof, or which modulates the binding between an active agent, or a biologically-active fragment thereof, and a GTPase, or a biologically-active fragment thereof, to which it binds.

Also presented herein is a method of identifying a blood precursor cell rejuvenating agent comprising: providing a blood precursor cell; providing a compound; and assaying the ability of the compound to rejuvenate the blood precursor cell. Methods for detecting rejuvenation of blood precursor cells are known in the art, and include, for example, detecting restoration of polarity of blood precursor cells as discussed in greater detail herein above. In some embodiments, the blood precursor cell rejuvenating agent rejuvenates the blood precursor cell at a dosage that does not mobilize a blood precursor cell. In some embodiments the method includes comparing the rejuvenating properties of a compound being tested to the rejuvenating properties of one or more reference compounds. Such a reference compound can be, for example, CASIN or other compounds described herein.

Also presented herein is a method of identifying a dermal epithelial precursor cell rejuvenating agent comprising: providing a dermal epithelial precursor cell; providing a compound; and assaying the ability of the compound to rejuvenate the dermal epithelial precursor cell. Methods for detecting rejuvenation of dermal epithelial precursor cells are known in the art, and include detection of dermal stem cell markers as discussed in greater detail herein above. In some embodiments, the dermal epithelial precursor cell rejuvenating agent rejuvenates the dermal epithelial precursor cells at a dosage that does not mobilize a blood precursor cell. In some embodiments the method includes comparing the rejuvenating properties of a compound being tested to the rejuvenating properties of one or more reference compounds. Such a reference compound can be, for example, CASIN or other compounds described herein.

Also presented herein is a method of identifying an intestinal epithelial precursor cell rejuvenating agent comprising: providing an intestinal epithelial precursor cell; providing a compound; and assaying the ability of the compound to rejuvenate the intestinal epithelial precursor cell. Methods for detecting rejuvenation of intestinal epithelial precursor cells are known in the art, and include detection of intestinal epithelial stem cell markers, as discussed in greater detail herein above. In some embodiments, the intestinal epithelial precursor cell rejuvenating agent rejuvenates the intestinal epithelial precursor cells at a dosage that does not mobilize a blood precursor cell. In some embodiments the method includes comparing the rejuvenating properties of a compound being tested to the rejuvenating properties of one or more reference compounds. Such a reference compound can be, for example, CASIN or other compounds described herein.

By modulating, it is meant that addition of the agent affects the activity or binding. The binding or activity modulation can be affected in various ways, including inhibiting, blocking, preventing, increasing, enhancing, or promoting it. The binding or activity effect does not have to be achieved in a specific way, e.g., it can be competitive, noncompetitive, allosteric, sterically hindered, via crosslinking between the agent and the GEF or GTPase, etc. The agent can act on either the active agent or GTPase. The agent can be an agonist, an antagonist, or a partial agonist or antagonist. The presence or amount of binding can be determined in various ways, e.g., by assaying for an activity promoted or inhibited by the active agent, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof The methods provided herein can be performed in vitro or in vivo as will be understood in the art. Examples of in vitro and in vivo methods are provided herein. The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds. Such a reference compound can be, for example, CASIN or other compounds described herein.

In certain embodiments, the methods can comprise an in vivo assay as described herein or otherwise known in the art. For example, in certain embodiments, the method comprises treating an animal with a compound provided herein, and evaluating the effects of treating the animal with the compound. In certain embodiments, the method comprises using an animal model for hemorrhagic shock, such as acute lung injury as described herein or otherwise known in the art. In certain embodiments, the method comprises using an animal model for neutrophil infiltration, hemorrhagic shock, inflammatory bowel disease, or lung inflammation.

The agent can be added simultaneously or sequentially. For example, the agent can be added to the active agent and then the resultant mixture can be further combined with the GTPase. The method can be carried out in liquid on isolated components, on a matrix (e.g., filter paper, nitrocellulose, agarose), in cells, on tissue sections, etc.

The method further relates to obtaining or producing agents that have been identified according to the above-described method. The preferred embodiments also relate to products identified in accordance with such methods.

Small Molecules

Small molecule inhibitors can be used to specifically inhibit and/or modulate Cdc42 as disclosed herein. Any type of small molecule inhibitor which is known to one of skill in the art may be used. Many methods are known to identify small molecule inhibitors and commercial laboratories are available to screen for small molecule inhibitors. For example, chemicals can be obtained from the compound collection at Merck® Research Laboratories (Rahway, N.J.) or a like company. The compounds can be screened for inhibition of a Cdc42 by automated robotic screening in a 96-well plate format. For example, the compounds can be dissolved at an initial concentration of about 50 µM in DMSO and dispensed into the 96-well plate. The 96-well plate assay may contain an appropriate number of units of Cdc42 and target (a substrate). Compounds that cause greater than a 50% inhibition of Cdc42 activity can be further diluted and tested to establish the concentration necessary for a 50% inhibition of activity. In some embodiments, the screen will include Cdc42 protein and one or more of its binding proteins and candidate inhibitors. The inhibitory effect of screened compound to disrupt Cdc42 target binding can be monitored using, for example, an ELISA-type test with Cdc42 or the target immobilized on the surface and residual binding can be detected, for example, using antibodies of Cdc42 target (binding)-molecule conjugated to a reporter (e.g., alkaline phosphate). Binding assays can also be performed using surface plasmon resonance (SPR) based interaction screening including Cdc42 and it's binding target and inhibitor or any other assay screening protein interactions (eg. yeast two hybrid systems, immunoprecipitation, immunocapture experiments coupled to enymatic or FACS detection etc.). In some embodiments, the candidate Cdc42 inhibitor can be tested for its ability to inhibit Cdc42 GTPase activity using assays known in the art. In other embodiments, the Cdc42 inhibitor can be tested for its ability to reduce the quantity of GTP-bound Cdc42, for example, relative to the quantity GDP-bound Cdc42, using assays known in the art.

Information disclosed herein (e.g., polypeptide or nucleic acid sequences, data from assays, etc.) can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments of the invention utilize computer-based systems that contain the information described herein and convert this information into other types of usable information (e.g., models for rational drug design). The term "a computer-based system" refers to the hardware, software, and any database used to analyze information (e.g., a Cdc42-specific inhibitor that enhances cancer therapy or a precursor cell rejuvenating agent), or fragments of these biomolecules so as to construct models or to conduct rational drug design. The computer-based system preferably includes the storage media described above, and a processor for accessing and manipulating the sequence data. The hardware of the computer-based systems of this embodiment comprise a central processing unit (CPU) and a database. A skilled artisan can readily appreciate that any one of the currently available computer-based systems are suitable.

In some embodiments, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. Information described herein can be stored in a well known manner in the main memory, any of the secondary storage devices, and/or a removable storage medium. Software for accessing and processing these sequences (such as search tools, compare tools, and modeling tools etc.) reside in main memory during execution.

As used herein, "a database" refers to memory that can store an information described herein (e.g., levels of cell rejuvenation, cancer inhibition, and values, levels or results from functional assays). Additionally, a "database" refers to a memory access component that can access manufactures having recorded thereon information described herein. In other embodiments, a database stores a "functional profile" comprising the values or levels and results (e.g., ability to rejuvenation of blood precursor cells, dermal epithelial precursor cells or intestinal epithelial precursor cells) from one or more functional assays, as described herein or known in the art, and relationships between these values or results. The data and values or results from functional assays can be stored and manipulated in a variety of data processor programs in a variety of formats. For example, the sequence data can be stored as text in a word processing file, a html file, or a pdf file in a variety of database programs familiar to those of skill in the art.

A "search program" refers to one or more programs that are implemented on the computer-based system to compare information (e.g., levels of cell rejuvenation or cancer inhibition). A search program also refers to one or more programs that compare one or more protein models to several protein models that exist in a database and one or more protein models to several peptides, peptidomimetics, and chemicals that exist in a database. A search program is used, for example, to compare levels of cell rejuvenation or cancer inhibition by providing a cancer therapy to cancer cells with or without a compound (e.g., a Cdc42-specific inhibitor) that are present in one or more databases. Still further, a search program can be used to compare values, levels or results from functional assays.

A "retrieval program" refers to one or more programs that can be implemented on the computer-based system to identify a homologous nucleic acid sequence, a homologous protein sequence, or a homologous protein model. A retrieval program can also used to identify, for example, Cdc42-specific inhibitors that can rejuvenation of blood precursor cells, dermal epithelial precursor cells or intestinal epithelial precursor cells. That is, a retrieval program can also be used to obtain a functional profile. Further, a functional profile can have one or more symbols that represent these molecules and/or models, an identifier that represents one or more inhibitors including, but not limited to values, levels, or results from a functional assay.

In any of the embodiments described herein, said Cdc42-specific inhibitor, said hematopoietic stem cell mobilizing agent, said compound that enhances cancer therapy, said GTPase inhibitor, said inhibitor of Cdc42, said inhibitor of GTPase Cdc42, said GTPase Cdc42 inhibitor, said agent capable of inhibiting GTPase Cdc42, or said agent that specifically inhibits Cdc42 comprises a compound of formula (I):

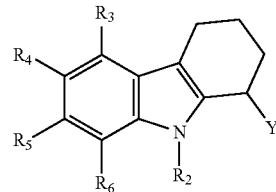

as a single enantiomer, a mixture of enantiomers, pharmaceutically acceptable salt, a solvate, or polymorph thereof, wherein:

Y is selected from the group consisting of —$OR_7$, —$NR_8R_9$, and —$NNR_8R_9$;

$R_7$ is selected from the group consisting of $C_{1-6}$ alkyl, —$(CH_2)_u C_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, —$(CH_2)_u C_{3-7}$cycloalkyl, $C_{2-6}$ alkenyl, $C_{1-6}$ alkoxy, hydroxy-$C_{1-6}$ alkyl, phenyl are each optionally substituted with one or more substitutents each independently selected from the group consisting of halo, —CN, —OH, $C_{1-6}$ alkoxyl, heteroaryl, $R_{19}$, and —$OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)_u C_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of $R_{21}$ and $R_{22}$, each $R_{21}$ is separately selected from the group consisting of halo, cyano, nitro, and hydroxy, each $R_{22}$ is separately selected from the group consisting of $C_{1-6}$ alkyl, $C_{1-6}$ alkoxy —$(CH_2)_u C_{3-7}$cycloalkyl, $C_{2-6}$ alkenyl, hydroxy-$C_{1-6}$ alkyl, $R_{19}$, and —$OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R_2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, —$(CH_2)_u C_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and —$O(CH_2)_u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$ and $R_6$ are each independently selected from the group consisting of hydrogen, halo, cyano, nitro, hydroxy, $C_{1-6}$ alkyl, $(CH_2)_u C_{3-7}$cycloalkyl, —$O(CH_2)_u C_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $-O(CH_2)_uC_{3-7}$cycloalkyl, $C_{2-6}$ alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, $-(CH_2)_u$ $C_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, $-(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

In some embodiments, one, two or three of $R_3$, $R_4$, $R_5$ and $R_6$ are not hydrogen.

In some embodiments, $R_4$ is selected from the group consisting of $C_{1-6}$ alkyl, $-(CH_2)_uC_{3-7}$cycloalkyl, $-O(CH_2)_uC_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said $C_{1-6}$ alkyl, $-(CH_2)_uC_{3-7}$cycloalkyl, $-O(CH_2)_uC_{3-7}$ cycloalkyl, $C_{2-6}$ alkenyl, $C_{1-6}$ alkoxy, and phenyl, each optionally substituted with one or more substituents each independently selected from the group consisting of halo$C_{1-6}$ alkyl, $-(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro.

In some embodiments: Y is $-NR_8R_9$, $R_8$ is hydrogen; and $R_9$ is $C_{1-6}$ alkyl optionally substituted with one or more substituents each independently selected from the group consisting of hydroxy, $R_{19}$ and $-OR_{20}$; each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments: each $R_{19}$ is independently phenyl optionally substituted with one or more substituents each independently selected from the group consisting of halo, $C_{1-6}$ alkyl, and $C_{1-6}$ alkoxy; and each $R_{20}$ is independently phenyl optionally substituted with one or more substituents each independently selected from the group consisting of halo, $C_{1-6}$ alkyl, and $C_{1-6}$ alkoxy.

In some embodiments, $R_2$ and $R_8$ are hydrogen.

In some embodiments, Y may be $-NR_8R_9$ and $R_8$ and $R_2$ come together to be $C_{1-3}$ alkyl linking together as a ring.

In some embodiments, $R_9$ is hydrogen.

In some embodiments, $R_9$ is $C_{1-6}$ alkyl optionally substituted with one or more substituents each independently selected from the group consisting of hydroxy, $R_{19}$ or $-OR_{20}$;

each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments, $R_9$ is hydrogen or $C_{1-6}$ alkyl, optionally substituted with one or more substituents each independently selected from the group consisting of hydroxyl, $R_{19}$ and $-OR_{20}$;

each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments, $R_4$ is selected from the group consisting of $C_{1-6}$ alkyl, $-(CH_2)_uC_{3-7}$cycloalkyl, $-O(CH_2)_uC_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said $C_{1-6}$ alkyl, $-(CH_2)_uC_{3-7}$cycloalkyl, $-O(CH_2)_uC_{3-7}$cycloalkyl, $C_{2-6}$ alkenyl, $C_{1-6}$ alkoxy, and phenyl, each optionally substituted with one or more $R_{23}$, each $R_{23}$ is independently selected from the group consisting of halo, $C_{1-6}$ alkyl, $-(CH_2)_uC_{3-7}$ cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, $C_{1-6}$ alkyl, $-(CH_2)_uC_{3-7}$cycloalkyl, $C_{2-6}$ alkenyl, $C_{1-6}$ alkoxy, $C_{1-6}$ alkyl substituted with up to 5 fluoro, and $C_{1-6}$ alkoxy substituted with up to 5 fluoro.

In some embodiments, $R_4$ is selected from the group consisting of $C_{1-6}$ alkyl, $C_{3-7}$cycloalkyl, $-OC_{3-7}$cycloalkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, $C_{1-6}$ alkyl, $C_{1-6}$ alkoxy, $C_{1-6}$ alkyl substituted with up to 5 fluoro, and $C_{1-6}$ alkoxy substituted with up to 5 fluoro.

In some embodiments, Y may be $-NR_8R_9$ and $R_8$ and $R_2$ come together to be $C_{1-3}$ alkyl linking together as a ring.

In some embodiments, $R_2$ is a hydrogen or selected from the group consisting of $C_{1-6}$ alkyl, $C_{3-7}$ cycloalkyl, and phenyl, said $C_{1-6}$ alkyl optionally substituted with one or more halo.

In some embodiments, $R_2$ is a hydrogen.

In some embodiments, $R_9$ is hydrogen, or $C_{1-6}$ alkyl, optionally substituted with one or more substituents each independently selected from the group consisting of hydroxyl, $R_{19}$ and —$OR_{20}$;

each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

In some embodiments, the compound of formula (I) is selected from the group consisting of:

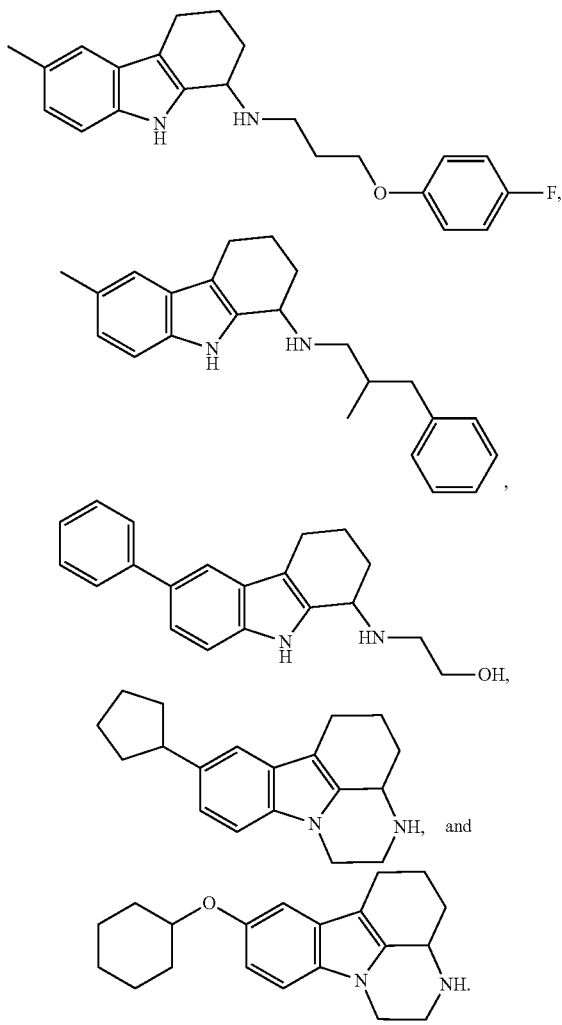

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR' or —(R)$_n$—NHC(O)R', where R and R' are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J.F.W. McOmie, *Protective Groups in Organic Chemistry* Plenum Press, 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane).

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

As used herein, the term "alkyl" refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group of the compounds of the invention may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

The substituent "R" appearing by itself and without a number designation refers to a substituent selected from the group consisting of hydrogen, alkyl, cycloalkyl, aryl, heteroaryl (bonded through a ring carbon) and heteroalicyclic (bonded through a ring carbon).

An "O-carboxy" group refers to a RC(=O)O— group, where R is as defined herein.

A "C-carboxy" group refers to a —C(=O)OR groups where R is as defined herein.

An "acetyl" group refers to a —C(=O)CH$_3$, group.

A "trihalomethanesulfonyl" group refers to a $X_3$CS(=O)$_2$— group where X is a halogen.

A "cyano" group refers to a —CN group.

An "isocyanato" group refers to a —NCO group.

A "thiocyanato" group refers to a —CNS group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonarnido" group refers to a $X_3$CS(=O)$_2$NR— group with X and R as defined herein.

An "O-carbamyl" group refers to a —OC(=O)—N(R)$_2$, group-with R as defined herein.

An "N-carbamyl" group refers to a ROC(=O)NH— group, with R as defined herein.

An "O-thiocarbamyl" group refers to a —OC(=S)—N(R)$_2$, group with R as defined herein.

An "N-thiocarbamyl" group refers to an ROC(=S)NH— group, with R as defined herein.

A "C-amido" group refers to a —C(=O)—N(R)$_2$ group with R as defined herein.

An "N-amido" group refers to a RC(=O)NH— group, with R as defined herein.

The term "perhaloalkyl" refers to an alkyl group where all of the hydrogen atoms are replaced by halogen atoms.

The term "acylalkyl" refers to a RC(=O)R'—group, with R as defined herein, and R' being a diradical alkylene group. Examples of acylalkyl, without limitation, may include CH$_3$C(=O)CH$_2$—, CH$_3$C(=O)CH$_2$CH$_2$—, CH$_3$CH$_2$C(=O)CH$_2$CH$_2$—, CH$_3$C(=O)CH$_2$CH$_2$CH$_2$—, and the like.

Unless otherwise indicated, when a substituent is deemed to be "optionally substituted," it is meant that the substitutent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

As used herein, "heterocyclyl" means a cyclic ring system comprising at least one heteroatom in the ring system backbone. The heteroatoms are independently selected from oxygen, sulfur, and nitrogen. Heterocyclyls may include multiple fused rings. Heterocyclyls may have any degree of saturation provided that at least one ring in the ring system is not aromatic. Heterocyclyls may be substituted or unsubstituted, and are attached to other groups via any available valence, preferably any available carbon or nitrogen. Preferred monocyclic heterocycles are of 5 or 6 members. In six membered monocyclic heterocycles, the heteroatom(s) are selected from one up to three of oxygen, sulfur, and nitrogen, and wherein when the heterocycle is five membered, preferably it has one or two heteroatoms selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. The attachment point of a heterocycle radical can be at the position of a nitrogen heteroatom or via a carbon atom of the heterocycle.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

As used herein, the term "heteroaryl" means an aromatic radical having one or more heteroatom(s) (e.g., oxygen, sulfur, or nitrogen) in the ring backbone and may include a single ring (e.g., pyridine) or multiple condensed rings (e.g., quinoline). Heteroaryl groups can carry one or more substituents, each independently selected from halo, hydroxy, amino, cyano, nitro, cycloalkyl, haloalkyl, aryl, heterocyclyl, mercapto, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, and trifluoromethyl. Representative examples of heteroaryl groups include, but are not limited to, optionally substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents can be halo, hydroxy, cyano, O—$C_{1-6}$-alkyl, $C_{1-6}$-alkyl, hydroxy-$C_{1-6}$-alkyl, and amino-$C_{1-6}$-alkyl.

Antisense Molecules

In some embodiments, the Cdc42-specific inhibitor can be an antisense molecule. The term "antisense" (AS) or "antisense fragment" refers to a polynucleotide fragment (comprising either deoxyribonucleotides, ribonucleotides or a mixture of both) having inhibitory antisense activity, which causes a decrease in the expression of the endogenous genomic copy of the corresponding gene. An AS polynucleotide refers to a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (see, for example, Aboul-Fadl T., Curr Med. Chem. 2005; 12(19): 2193-214; Crooke S T, Curr Mol. Med. 2004 August; 4(5):465-87; Crooke S T, Annu Rev Med. 2004; 55:61-95; Vacek M et al., Cell Mol Life Sci. 2003 May; 60(5):825-33; Cho-Chung Y S, Arch Pharm Res. 2003 March; 26(3):183-91; Moreira J N et al., Rev Recent Clin Trials 2006 September; 1(3):217-35). There are further reviews on the chemical (Crooke, 1995; Uhlmann et al, 1990), cellular (Wagner, 1994) and therapeutic (Hanania, et al, 1995; Scanlon, et al, 1995; Gewirtz, 1993) aspects of this technology. Antisense intervention in the expression of specific genes can be achieved by the use of synthetic AS oligonucleotide sequences (see, e.g., Lefebvre-d'Hellencourt et al, 1995; Agrawal, 1996; LevLehman et al, 1997).

AS oligonucleotide sequences may be short sequences of DNA, typically a 15-mer to a 30-mer but may be as small as a 7-mer (Wagner et al, 1996), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix, which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996). For example, the computer program OLIGO® (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art.

Further, the oligonucleotides are also selected as needed so that analogue substitutions do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for the glial fibrillary acidic protein (GFAP), for the establishment of tectal plate formation in chick (Galileo et al., 1991) and for the N-myc protein, responsible for the maintenance of cellular heterogeneity in neuroectodermal cultures (ephithelial vs. neuroblastic cells, which differ in their colony forming abilities, tumorigenicity and adherence) (Rosolen et al., 1990; Whitesell et al, 1991). Antisense oligonucleotide inhibition of basic fibroblast growth factor (bFgF), having mitogenic and angiogenic properties, suppressed 80% of growth in glioma cells (Morrison, 1991) in a saturable and specific manner. Being hydrophobic, antisense oligonucleotides interact well with phospholipid membranes (Akhter et al., 1991). Following their interaction with the cellular plasma membrane, they are actively (or passively) transported into living cells (Loke et al., 1989), in a saturable mechanism predicted to involve specific receptors (Yakubov et al., 1989).

siRNA

In other embodiments, the Cdc42-specific inhibitor can be a "small interfering RNA" (siRNA). siRNA refers to an RNA molecule which decreases or silences (prevents) the expression of a gene/mRNA (e.g., Cdc42) of its endogenous cellular counterpart. The term is understood to encompass "RNA interference" (RNAi). RNA interference (RNAi) refers to the process of sequence-specific post transcriptional gene silencing in mammals mediated by small interfering RNAs (siRNAs, e.g., short hairpin RNAs (shRNAs)) (Fire et al, 1998, Nature 391, 806). The corresponding process in plants is commonly referred to as specific post transcriptional gene silencing or RNA silencing and is also referred to as quelling in fungi. The RNA interference response may feature an endonuclease complex containing an siRNA, commonly referred to as an RNA-induced silencing complex (RISC), which mediates cleavage of single-stranded RNA having sequence complementary to the antisense strand of the siRNA duplex. Cleavage of the target RNA may take place in the middle of the region complementary to the antisense strand of the siRNA duplex (Elbashir et al 2001, Genes Dev., 15, 188). For recent information on these terms and proposed mechanisms, see Bernstein E., Denli A M., Hannon G J: The rest is silence. RNA. 2001 November; 7(11):1509-21; and Nishikura K.: A short primer on RNAi: RNA-directed RNA polymerase acts as a key catalyst. Cell. 2001 November 16; 107(4):415-8.

RNAi is an efficient method for the inactivation of genes (Nature Reviews, 2002, v. 3, p. 737-47; Nature, 2002, v. 418, p. 244-51). As a method, it is based on the ability of dsRNA species to enter a specific protein complex, where it is then targeted to the complementary cellular RNA and specifically degrades it. In more detail, dsRNAs are digested into short (17-29 bp) inhibitory RNAs (siRNAs) by type III RNAses (DICER, Drosha, etc) (Nature, 2001, v. 409, p. 363-6; Nature, 2003, 425, p. 415-9). These fragments and complementary mRNA are recognized by the specific RISC protein complex. The whole process is culminated by endonuclease cleavage of target mRNA (Nature Reviews, 2002, v. 3, p. 737-47; Curr Opin Mol. Ther. 2003 June; 5(3):217-24).

For disclosure on how to design and prepare siRNA to known genes see, for example, Chalk A M, Wahlestedt C, Sonnhammer E L. 2004 Jun. 18; 319(1):264-74; Sioud M, Leirdal M., Methods Mol. Biol. 2004; 252:457-69; Levenkova N, Gu Q, Rux J J. 2004 Feb. 12; 20(3):430-2; and Ui-Tei K, Naito Y, Takahashi F, Haraguchi T, Ohki-Hamazaki H, Juni A, Ueda R, Saigo K., Nucleic Acids Res. 2004 Feb. 9; 32(3):936-48. See also PCT publications WO 2004/015107 (Atugen) and WO 02/44321 (Tuschl et al), and also Chiu Y L, Rana T M. RNA 2003 September; 9(9):1034-48 and U.S. Pat. Nos. 5,898,031 and 6,107,094 (Crooke) for production of modified/more stable siRNAs.

DNA-based vectors capable of generating siRNA within cells have been developed. The method generally involves transcription of short hairpin RNAs that are efficiently processed to form siRNAs within cells. (see, e.g., Paddison et al. PNAS 2002, 99:1443-1448; Paddison et al. Genes & Dev 2002, 16:948-958; Sui et al. PNAS 2002, 8:5515-5520; and Brummelkamp et al. Science 2002, 296:550-553). These reports describe methods to generate siRNAs capable of specifically targeting numerous endogenously and exogenously expressed genes.

For methods related to the delivery of siRNAs, see, for example, Shen et al (FEBS letters 539: 111-114 (2003)), Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details, see, for example, Tolentino et al., Retina 24(1) February 2004 pp 132-138.

In some embodiments the oligoribonucleotide according to embodiments disclosed herein comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

Ribozymes

In some embodiments, the Cdc42-specific inhibitor can be a ribozyme. The term "ribozyme" refers to an RNA molecule that possesses RNA catalytic ability and cleaves a specific site in a target RNA. In accordance with the embodiments disclosed herein, ribozymes which cleave mRNA (e.g., Cdc42 mRNA) may be utilized as inhibitors. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stochiochemistry. (Hampel and Tritz, 1989; Uhlenbeck, 1987).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

The term "nucleic acids", as used herein, may be DNA or RNA or modified versions thereof. Nucleic acids may also include modified nucleotides that permit correct read through by a polymerase and do not alter expression of a polypeptide encoded by that nucleic acid. The terms "nucleic acid" and "oligonucleotide" are used interchangeably to refer to a molecule comprising multiple nucleotides. As used herein, the terms refer to oligoribonucleotides as well as oligodeoxyribonucleotides. The terms shall also include polynucleosides (e.g., a polynucleotide minus the phosphate) and any other organic base containing polymer. Nucleic acids include vectors, e.g., plasmids, as well as oligonucleotides. Nucleic acid molecules can be obtained from existing nucleic acid sources, but are preferably synthetic (e.g., produced by oligonucleotide synthesis).

Polynucleotides to be used according to embodiments disclosed herein may undergo modifications so as to possess improved therapeutic properties. Modifications or analogs of nucleotides can be introduced to improve the therapeutic properties of polynucleotides. Improved properties include increased nuclease resistance and/or increased ability to permeate cell membranes. Nuclease resistance, where needed, is provided by any method known in the art that does not interfere with biological activity of the AS polynucleotide, siRNA, cDNA and/or ribozymes as needed for the method of use and delivery (Iyer et al., 1990; Eckstein, 1985; Spitzer and Eckstein, 1988; Woolf et al., 1990; Shaw et al., 1991). Modifications that can be made to oligonucleotides in order to enhance nuclease resistance include modifying the phosphorous or oxygen heteroatom in the phosphate backbone. These include preparing methyl phosphonates, phosphorothioates, phosphorodithioates and morpholino oligomers. In one embodiment it is provided by having phosphorothioate bonds linking between the four to six 3'-terminus nucleotide bases. Alternatively, phosphorothioate bonds link all the nucleotide bases. Other modifications known in the art may be used where the biological activity is retained, but the stability to nucleases is substantially increased.

All analogues of, or modifications to, a polynucleotide may be employed with the embodiments disclosed herein, provided that said analogue or modification does not substantially affect the function of the polynucleotide. The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiuracil, 8-halo adenine, 8-aminoadenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of polynucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, cyclic backbones, or acyclic backbones, as well as LNA ("locked nucleic acid").

Embodiments disclosed herein also include nucleic acids (e.g., siRNA) that can have the following degrees of homology or identity to a Cdc42-specific inhibitory nucleic acid: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate Cdc42-specific inhibitory nucleic acids having greater than or equal to 35% homology or identity can be identified by methods known in the art and can be subsequently examined using functional assays, for example, the assays described herein and those known in the art.

The term "homology" refers to the percent of identity between two polynucleotide or two polypeptide moieties. The correspondence between the sequence from one moiety to another can be determined by techniques known in the art. For example, homology can be determined by a direct comparison of the sequence information between two polynucleotide or polypeptide molecules by aligning the sequence information and using readily available computer programs. Alternatively, homology can be determined by hybridization of polynucleotides under conditions, which form stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

Preparation of Peptides and Polypeptides

In some embodiments, the Cdc42-specific inhibitor can be a polypeptide (e.g., a dominant negative peptide, an antibody, or an affibody). Polypeptides may be produced, for example, via several methods known in the art (e.g., synthetically or via recombinant methods).

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. Polypeptide products can be biochemically synthesized such as by employing standard solid phase techniques. Such methods include but are not limited to exclusive solid phase synthesis, partial solid phase synthesis methods, fragment condensation, classical solution synthesis. These methods are preferably used when the peptide is relatively short (e.g., 10 kDa) and/or when it cannot be produced by recombinant techniques (e.g., not encoded by a nucleic acid sequence) and therefore involves different chemistry. Solid phase polypeptide synthesis procedures are well known in the art and further described by John Morrow Stewart and Janis Dillaha Young, Solid Phase Peptide Syntheses (2nd Ed., Pierce Chemical Company, 1984). Synthetic polypeptides can optionally be purified by preparative high performance liquid chromatography [Creighton T. (1983) Proteins, structures and molecular principles. WH Freeman and Co. N.Y.], after which their composition can be confirmed via amino acid sequencing. In cases where large amounts of a polypeptide are desired, it can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In some embodiments, the method of making the polypeptides or fragments thereof is to clone a polynucleotide comprising the cDNA of the gene into an expression vector and culture the cell harboring the vector so as to express the encoded polypeptide, and then purify the resulting polypeptide, all performed using methods known in the art as described in, for example, Marshak et al., "Strategies for Protein Purification and Characterization. A laboratory course manual." CSHL Press (1996). (in addition, see, e.g., Bibl Haematol. 1965; 23:1165-74 Appl Microbiol. 1967 July; 15(4):851-6; Can J. Biochem. 1968 May; 46(5):441-4; Biochemistry. 1968 July; 7(7):2574-80; Arch Biochem Biophys. 1968 Sep. 10; 126(3):746-72; Biochem Biophys Res Commun. 1970 Feb. 20; 38(4):825-30).).

The expression vector can include a promoter for controlling transcription of the heterologous material and can be either a constitutive or inducible promoter to allow selective transcription. Enhancers that can be required to obtain necessary transcription levels can optionally be included. The expression vehicle can also include a selection gene.

Vectors can be introduced into cells or tissues by any one of a variety of methods known within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al. (1986).

Preparation of Anti-Cdc42 Antibodies

Antibodies that bind to Cdc42 or a fragment derived therefrom may be prepared using an intact polypeptide or fragments containing smaller polypeptides as the immunizing antigen. For example, it may be desirable to produce antibodies that specifically bind to the N- or C-terminal or any other suitable domains of Cdc42. The polypeptide used to immunize an animal can be derived from translated cDNA or chemical synthesis and can be conjugated to a carrier protein, if desired. Such commonly used carriers which are chemically coupled to the polypeptide include keyhole limpet hemocyanin (KLH), thyroglobulin, bovine serum albumin (BSA) and tetanus toxoid. The coupled polypeptide is then used to immunize the animal If desired, polyclonal or monoclonal antibodies can be further purified, for example by binding to and elution from a matrix to which the polypeptide or a peptide to which the antibodies were raised is bound. Those skilled in the art know various techniques common in immunology for purification and/or concentration of polyclonal as well as monoclonal antibodies (Coligan et al, Unit 9, Current Protocols in Immunology, Wiley Interscience, 1994).

Methods for making antibodies of all types, including fragments, are known in the art (See for example, Harlow and Lane, Antibodies: A Laboratory Manual, Cold Spring Harbor Laboratory, New York (1988)). Methods of immunization, including all necessary steps of preparing the immunogen in a suitable adjuvant, determining antibody binding, isolation of antibodies, methods for obtaining monoclonal antibodies, and humanization of monoclonal antibodies are all known to the skilled artisan The antibodies may be humanized antibodies or human antibodies. Antibodies can be humanized using a variety of techniques known in the art including CDR-grafting (EP239,400: PCT publication WO0.91/09967; U.S. Pat. Nos. 5,225,539; 5,530,101; and 5,585,089, veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,332).

The monoclonal antibodies as defined include antibodies derived from one species (such as murine, rabbit, goat, rat, human, etc.) as well as antibodies derived from two (or more) species, such as chimeric and humanized antibodies.

Completely human antibodies are particularly desirable for therapeutic treatment of human patients. Human antibodies can be made by a variety of methods known in the art including phage display methods using antibody libraries derived from human immunoglobulin sequences. See also U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Additional information regarding all types of antibodies, including humanized antibodies, human antibodies and antibody fragments can be found in WO 01/05998, which is incorporated herein by reference in its entirety.

Neutralizing antibodies can be prepared by the methods discussed above, possibly with an additional step of screening for neutralizing activity by, for example, a survival assay.

Embodiments disclosed herein also relate to the preparation and use of affibodies, binding proteins of non-Ig origin developed by combinatorial protein engineering principles, as described, for example, in Nygren Pa. 2008 FEBS Journal 275:2668-2676.

The polypeptides employed in embodiments disclosed herein may also be modified, optionally chemically modified, in order to improve their therapeutic activity. "Chemically modified"—when referring to the polypeptides, refers to a polypeptide where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, GPI anchor formation, covalent attachment of a lipid or lipid derivative, methylation, myristylation, pegylation, prenylation, phosphorylation, ubiqutination, or any similar process.

Additional possible polypeptide modifications (such as those resulting from nucleic acid sequence alteration) include substitutions, deletions, and insertions.

A "conservative substitution" refers to the substitution of an amino acid in one class by an amino acid of the same class, where a class is defined by common physicochemical amino acid side chain properties and high substitution frequencies in homologous polypeptides found in nature, as determined, for example, by a standard Dayhoff frequency exchange matrix or BLOSUM matrix.

A "non-conservative substitution" refers to the substitution of an amino acid in one class with an amino acid from another class; for example, substitution of an Ala, a class II residue, with a class III residue such as Asp, Asn, Glu, or Gln.

A "deletion" refers to a change in either nucleotide or amino acid sequence in which one or more nucleotides or amino acid residues, respectively, are absent.

An "insertion" or "addition" refers to a change in a nucleotide or amino acid sequence which has resulted in the addition of one or more nucleotides or amino acid residues, respectively, as compared to the naturally occurring sequence.

A "substitution" refers to the replacement of one or more nucleotides or amino acids by different nucleotides or amino acids, respectively. As regards amino acid sequences the substitution may be conservative or non-conservative.

Embodiments disclosed herein also include polypeptides (e.g., dominant negative polypeptides or antibodies) that can have the following degrees of homology or identity to a Cdc42-specific inhibitory polypeptide: 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Candidate Cdc42-specific inhibitory polypeptides having greater than or equal to 35% homology or identity can be identified by methods known in the art and can be subsequently examined using functional assays, for example, the assays described herein and those known in the art.

Other Methods for Rejuvenation and Treatments

The method of rejuvenation of blood precursor cells, dermal epithelial precursor cells or intestinal epithelial precursor cells, can be used for stem/progenitor cells in patients who will undergo cytoreductive therapy, such as chemotherapy or radiation therapy. Before or after rejuvenation, the stem/progenitor cells are collected from the peripheral blood and either stored, or expanded in culture. The method of rejuvenation of blood precursor cells, dermal epithelial precursor cells or intestinal epithelial precursor cells can also be used for stem/progenitor cells in individuals who will serve as allogenic donors of progenitor cells. Other diseases and disorders for which the active compound is beneficial in addition to those already described are leukopenia of various origins including, congenital leukopenia, childhood or adult cyclic neutropenia, post-infective neutropenia, and myelodysplastic syndrome. The methods can further be used to cause tolerance of a recipient for organ transplantation.

The methods of rejuvenation of blood precursor cells, dermal epithelial precursor cells or intestinal epithelial precursor cells can also be used in cancer therapy methods and in methods for inhibiting, ameliorating, or ablation of cancer cells and/or tumors, where Cdc42 activity levels are restored to normal levels in accordance with the teachings provided herein. Rejuvenation of blood precursor cells, dermal epithelial precursor cells or intestinal epithelial precursor cells (e.g., by administering a Cdc42-specific inhibitor) can be a used in combination with traditional cancer therapies (e.g., chemotherapy or radiotherapy) to provide more effective or improved cancer therapy methods and methods for inhibiting, ameliorating, or ablation of cancer cells and/or tumors.

The methods can additionally be used for gene therapy. Because pluripotent stem cells are self-renewing, and give rise to cell progenitors as well as mature blood cells, the stem cells are an appropriate target for gene therapy. Before or after rejuvenation, stem/progenitor cells can be collected. The stem/progenitor cells can be modified to deliver gene products upon reintroduction to the individual. After modification, the cells are reinfused into the affected individual.

In some contexts, the terms "ameliorating," "treating," "treatment," "therapeutic," or "therapy" do not necessarily mean total cure or abolition of the disease or condition. Any alleviation of any undesired signs or symptoms of a disease or condition, to any extent, can be considered amelioration, and in some respects a treatment and/or therapy.

Typical conditions that can be ameliorated or otherwise benefited by the treatment methods herein include, but are not limited to, hematopoietic disorders, such as aplastic anemia, Fanconi anemia, leukemias, drug-induced anemias, and hematopoietic deficits from chemotherapy or radiation therapy. The methods are also useful in enhancing the success of transplantation during and following immunosuppressive treatments as well as in effecting more efficient wound healing and treatment of bacterial inflammation. The methods are also useful for treating subjects who are immunocompromised or whose immune system is otherwise impaired. Typical conditions that are ameliorated or otherwise benefited by the method of the present invention, include retrovirus infections and more specifically human immunodeficiency virus (HIV) infections. The methods thus target a broad spectrum of conditions for which elevation of progenitor cells and/or stem cells in a subject would be beneficial or, where harvesting of progenitor cells and/or stem cell for subsequent stem cell transplantation would be beneficial.

The compounds of preferred embodiments can be used in relation to disorders arising from bone marrow cells. In normal bone marrow, the myelocytic series (polymorphonuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphonuclear leukocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each are known to the person of ordinary skill in the art and are found, for example, in *Immunology, Imunopathology and Immunity*, Fifth Edition, Sell et al. Simon and Schuster (1996), which is incorporated herein by reference in its entirety. Accordingly, the preferred embodiments are directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; Fanconi anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadenoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

The preferred embodiments relate to methods of treatment of disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory myopathies, mixed connective tissue disease, and polyarteritis *nodosa* and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Szary syndrome, and Hodgkin disease.

The compounds of preferred embodiments can be used in relation to diseases of the skin. Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma, tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and *porphyria*; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

The compounds of preferred embodiments can be used in relation to disorders involving the spleen. Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

The compounds of preferred embodiments can be used in relation to disorders involving blood vessels. Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

The compounds of preferred embodiments can be used in relation to disorders involving red cells. Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

The compounds of preferred embodiments can be used in relation to disorders involving B-cells. Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

The compounds of preferred embodiments can be used in relation to disorders related to reduced platelet number. Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

The compounds of preferred embodiments can be used in relation to disorders involving precursor T-cell neoplasms. Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Szary syndrome, peripheral T-cell lymphoma, unspecified, angioimmunoblastic T-cell lymphoma, angiocentric lymphoma (NK/T-cell lymphoma4a), intestinal T-cell lymphoma, adult T-cell leukemia/lymphoma, and anaplastic large cell lymphoma.

The compounds of preferred embodiments can be used in relation to disorders of the bone. Bone-forming cells include the osteoprogenitor cells, osteoblasts, and osteocytes. The disorders of the bone are complex because they can have an impact on the skeleton during any of its stages of development. Hence, the disorders can have variable manifestations and can involve one, multiple or all bones of the body. Such disorders include, congenital malformations, achondroplasia and thanatophoric dwarfism, diseases associated with abnormal matrix such as type 1 collagen disease, osteoporosis, Paget disease, rickets, osteomalacia, high-turnover osteodystrophy, low-turnover of aplastic disease, osteonecrosis, pyogenic osteomyelitis, tuberculous osteomyelitism, osteoma, osteoid osteoma, osteoblastoma, osteosarcoma, osteochondroma, chondromas, chondroblastoma, chondromyxoid fibroma, chondrosarcoma, fibrous cortical defects, fibrous dysplasia, fibrosarcoma, malignant fibrous histiocytoma, Ewing sarcoma, primitive neuroectodermal tumor, giant cell tumor, and metastatic tumors.

The compounds of preferred embodiments can be used in relation to disorders involving the tonsils. Disorders involving the tonsils include, but are not limited to, tonsillitis, Peritonsillar abscess, squamous cell carcinoma, dyspnea, hyperplasia, follicular hyperplasia, reactive lymphoid hyperplasia, non-Hodgkin's lymphoma and B-cell lymphoma.

The compounds of preferred embodiments can be used in relation to disorders involving the liver. Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A-E infection and infection by other hepatitis viruses, clinicopathologic syndromes, such as the carrier state, asymptomatic infection, acute viral hepatitis, chronic viral hepatitis, and fulminant hepatitis; autoimmune hepatitis, drug- and toxin-induced liver disease, such as alcoholic liver disease; inborn errors of metabolism and pediatric liver disease, such as hemochromatosis, Wilson disease, alpha.1-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrahepatic cholestasis of pregnancy; hepatic complications of organ or bone marrow transplantation, such as drug toxicity after bone marrow transplantation, graft-versus-host disease and liver rejection, and non-immunologic damage to liver allografts; tumors and tumorous conditions, such as nodular hyperplasias, adenomas, and malignant tumors, including primary carcinoma of the liver and metastatic tumors.

The compounds of preferred embodiments can be used in relation to disorders involving the colon. Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

The compounds of preferred embodiments can be used in relation to disorders involving the lung. Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

The compounds described herein can be administered as sole active ingredients and/or in a mixture with one or more additional active ingredients or agents that are therapeutically or nutritionally useful, such as antibiotics, vitamins, herbal extracts, anti-inflammatories, glucose, antipyretics, analgesics, growth factors (e.g., granulocyte-macrophage colony stimulating factor (GM-CSF), Interleukins (IL-1, IL-2, IL-3, IL-4, IL-5, IL-6, IL-7, IL-8, IL-9, IL-10 IL-11, IL-12, IL-13, IL-14, or IL-15), TPO, or SCF), or other growth factors such as CSF-1, SF, EPO, leukemia inhibitory factor (LIF), or fibroblast growth factor (FGF), as well as C-KIT ligand, M-CSF and TNF-α, PIXY-321 (GM-CSF/IL-3 fusion protein), macrophage inflammatory protein, stem cell factor, thrombopoietin, growth related oncogene, G-CSF, VEGF, chemical agents (e.g., AMD3100) or chemotherapy and the like.

The term, "in conjunction with", as used herein, refers to concurrent administration of the active compound with and additional agent (e.g., a growth factor or chemical agent), as well as administration of the active compound within several days (e.g., within approximately 1 to 7 days) of administration of the growth factor. Administration of the additional agent can be before, concurrent, or after administration of the active compound.

Some embodiments disclosed herein concern improved therapeutic approaches, wherein an effective amount of a Cdc42-specific inhibitor is combined or co-administered with at least one additional therapeutic agent (including, but not limited to, chemotherapeutic antineoplastics, apoptosis modulating agents, immunotherapeutics, antimicrobials, antivirals, antifungals, and anti-inflammatory agents) and/or therapeutic technique (e.g., surgical intervention, and/or radiotherapies). In some embodiments, compounds disclosed herein (e.g., a Cdc42-specific inhibitor) can sensitize a subject or cells within the subject to a second agent (e.g., a chemotherapeutic agent) or therapeutic technique (e.g., radiotherapy).

The terms "sensitize" and "sensitizing," as used herein, refer to making, through the administration of a first agent (e.g., a Cdc42-specific inhibitor), an animal or a cell within an animal more susceptible, or more responsive, to the biological effects (e.g., promotion or retardation of an aspect of cellular function including, but not limited to, cell growth, proliferation, invasion, angiogenesis, or apoptosis) of a second agent or therapeutic technique. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent or therapeutic technique with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450%, or at least 500% over the response in the absence of the first agent.

The term "hyperproliferative disease" or "hyperproliferative disorder" as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (non-cancerous) or malignant (cancerous).

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "anti-neoplastic agent," as used herein, refers to any compound that retards the proliferation, growth, or spread of a targeted (e.g., malignant) neoplasm.

The term "apoptosis modulating agents," as used herein, refers to agents which are involved in modulating (e g, inhibiting, decreasing, increasing, promoting) apoptosis. Examples of apoptosis modulating agents include, but are not limited to, proteins and nucleic acids, which comprise a death domain or encode a death domain such as, but not limited to, Fas/CD95, TRAMP, TNF RI, DR1, DR2, DR3, DR4, DR5, DR6, FADD, and RIP. Small RNAs such as MIR RNAs can also be apoptosis modulating agents (e.g., MIR-34a). Other examples of apoptotic modulating agents include, but are not limited to, TNF-alpha, Fas ligand, antibodies to Fas/CD95 and other TNF family receptors, TRAIL, antibodies to TRAILR1 or TRAILR2, Bcl-2, p53, BAX, BAD, Akt, CAD, PI3 kinase, PP1, and caspase proteins. Modulating agents broadly include agonists and antagonists of TNF family receptors and TNF family ligands. Apoptosis modulating agents may be soluble or membrane bound (e.g. ligand or receptor). Preferred apoptosis modulating agents are inducers of apoptosis, such as TNF or a TNF-related ligand, particularly a TRAMP ligand, a Fas/CD95 ligand, a TNFR-1 ligand, or TRAIL.

A number of suitable anticancer agents are contemplated for combination or co-administration with a Cdc42-specific inhibitor to treat, prevent, or ameliorate any of the aforementioned diseases, maladies, conditions, or disorders. Indeed, some embodiments contemplate, but are not limited to, administration of a Cdc42-specific inhibitor in combination or co-administered with numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) Cdc42; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-alpha) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteasome inhibitors: NF-KB modulators; anti-CDK compounds; HDAC inhibitors; and the like. Numerous other examples of chemotherapeutic compounds and anticancer therapies suitable for mixture or co-administration with the disclosed inhibitors of Cdc42 are known to those skilled in the art.

In more embodiments, the Cdc42-specific inhibitors described herein and used in the methods disclosed are mixed or combined or co-administered with anticancer agents that induce or stimulate apoptosis. Agents that induce apoptosis which are suitable in such compositions, mixtures, therapies and methods include, but are not limited to, radiation (e.g., X-rays, gamma rays, UV); tumor necrosis factor (TNF)-related factors (e.g., TNF family receptor proteins, TNF family ligands, TRAIL, antibodies to TRAILR1 or TRAILR2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, plateletderived growth factor receptor (PDGFR) kinase inhibitor, and Bcr-Abl kinase inhibitors (such as GLEEVEC®)); antisense molecules; antibodies (e.g., HERCEPTIN®, RITUXAN®, ZEVALIN®, and AVASTIN®); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); antiinflammatory drugs (e.g., butazolidin, DECADRON®, DELTASONE®, dexamethasone, dexamethasone intensol, DEXONE®, HEXADROL®, hydroxychloroquine, METICORTEN®, oradexon, ORASONE®, oxyphenbutazone, PEDIAPRED®, phenylbutazone, PLAQUENIL®, prednisolone, prednisone, PRELONE®, and TANDEARIL®); and cancer chemotherapeutic drugs (e.g., irinotecan (CAMPTOSAR®), CPT-11, fludarabine (FLUDARA®), dacarbazine (DTIC®), dexamethasone, mitoxantrone, MYLOTARG®, VP-16®, cisplatin, carboplatin, oxaliplatin, 5-FU®, doxorubicin, gemcitabine, bortezomib, gefitinib, bevacizumab, TAXOTERE® or TAXOL®); cellular signaling molecules; ceramides and cytokines; staurosporine, and the like.

In still other embodiments, compositions and methods described provide a Cdc42-specific inhibitor and at least one anti-hyperproliferative or antineoplastic agent selected from alkylating agents, antimetabolites, and natural products (e.g., herbs and other plant and/or animal derived compounds).

Alkylating agents suitable for use in the present compositions, mixtures, therapies, and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC®; dimethyltriazenoimid-azolecarboxamide).

In some embodiments, antimetabolites suitable for use in the present compositions, mixtures, therapies, and methods include, but are not limited to: 1) folic acid analogs (e.g., methotrexate (amethopterin)); 2) pyrimidine analogs (e.g., fluorouracil (5-fluorouracil; 5-FU®), floxuridine (fluorodeoxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use with the compositions, mixtures, therapies, and methods described herein include, but are not limited to: 1) *vinca* alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods disclosed herein. For example, the U.S. Food and Drug Administration maintains a formulary of oncolytic agents approved for use in the United States. International counterpart agencies to the U.S.F.D.A. maintain similar formularies.

In some embodiments, conventional anticancer agents for use in administration with the present compounds include, but are not limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, bevacizumab, demethylating agents, inhibitors of her-2, inhibitors of IGF-1R, VEGF, inhibitors of VEGFR, mTOR inhibitors, mitotic inhibitors, Smad inhibitors and taxanes. These agents can be prepared and used singularly, in combined therapeutic compositions, in kits, or in combination with immunotherapeutic agents, and the like.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

Some embodiments disclosed herein relate to an improved radiation therapy, wherein a Cdc42-specific inhibitor is provided before, during, or after a radiation therapy. Embodiments disclosed herein are not limited by the types, amounts, or delivery and administration systems used to deliver the therapeutic dose of radiation to a subject. For example, the subject may receive photon radiotherapy, particle beam radiation therapy, other types of radiotherapies, and combinations thereof. In some embodiments, the radiation is delivered to the subject using a linear accelerator. In still other embodiments, the radiation is delivered using a gamma knife, and in others, the radiation administered in the form of a radioactive implantable pellet.

The source of radiation can be external or internal to the subject. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The subject may optionally receive radiosensitizers in addition to the Cdc42-specific inhibitor and radiation (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of cancer cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation refers to radiation comprising particles or photons that have sufficient energy to produce ionization, e.g., gain or loss of electrons (as described in, for example, U.S. Pat. No. 5,770,581 incorporated herein by reference in its entirety). The effects of radiation can be at least partially controlled by the clinician. The dose of radiation can be fractionated for maximal target cell exposure and reduced toxicity.

Pharmaceutical Compositions and Administration

Compounds, or mixtures of compounds described herein, can be synthetic, naturally-occurring, or a combination thereof. Compounds, or mixtures of compounds described herein can comprise amino acids, nucleotides, hydrocarbons, lipids, polysaccharides, etc. Compounds, or mixtures of compounds described herein preferably comprise a Cdc42-specific inhibitor (e.g., CASIN). Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some emodiments comprise the administration of a pharmaceutically effective quantity of active agent or its pharmaceutically acceptable salts or esters, active agent analogs or their pharmaceutically acceptable salts or esters, or a combination thereof The compositions and preparations described preferably contain at least 0.1% of active agent. The percentage of the compositions and preparations can, of course, be varied, and can contain between about 2% and 60% of the weight of the amount administered. Preferably, the percentage of the compositions and preparations can contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The active agent can form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agents which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents which contain an acidic moiety, such as, but not limited to a carboxylic acid, can form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the preferred embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof. Solvates of the active agent are preferably hydrates.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds according to the preferred embodiments are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methyl ammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts can be prepared by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guanidine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

As indicated above, a further object of the preferred embodiments relates to a pharmaceutical composition comprising at least one compound (e.g., a Cdc42-specific inhibitor such as CASIN) and a pharmaceutically acceptable vehicle or support.

The compounds can be formulated in various forms, including solid and liquid forms, such as tablets, gel, syrup, powder, aerosol, creams, lotions, tinctures, foams, etc.

The compositions of the preferred embodiments can contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds according to the preferred embodiments can also be used enterally. Orally, the compounds according to the preferred embodiments are suitable administered at the rate of 100 µg to 100 mg per day per kg of body weight. Preferably, orally, the compounds according to the preferred embodiments are suitable administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance. Preferably, a method of administration consists in using a suitable form containing from about 1, 2, 5, 10, 25, or 50 mg to about 100, 200, 300, 400, 500 mg of active substance.

The compounds according to the preferred embodiments can also be administered parenterally in the form of solutions or suspensions for intravenous or intramuscular perfusions or injections. In that case, the compounds according to the preferred embodiments are generally administered at the rate of about 10 µg to 10 mg per day per kg of body weight; a preferred method of administration consists of using solutions or suspensions containing approximately from 0.01 mg to 1 mg of active substance per ml. Preferably, the compounds according to the preferred embodiments are generally administered at the rate of about 10, 20, 30, 40, 50, 60, 70, 80, 90, or 100 µg to 1, 2, 3, 4, 5, 6, 7, 8, 9, or 10 mg per day per kg of body weight; a preferred method of administration consists of using solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml.

The compounds can be used in a substantially similar manner to other known anti-tumor agents for treating (both chemopreventively and therapeutically) various tumors. For the compounds of the preferred embodiments, the anti-tumor dose to be administered, whether a single dose, multiple dose, or a daily dose, will of course vary with the particular compound employed because of the varying potency of the compound, the chosen route of administration, the size of the recipient, the type of tumor, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. For example, an oncologist skilled in the art of cancer treatment will be able to ascertain, without undue experimentation, appropriate protocols for the effective administration of the compounds of the preferred embodiments related to cancer therapy, such as by referring to the earlier published studies on compounds found to have anti-tumor properties.

The active compounds and/or pharmaceutical compositions of the embodiments disclosed herein can be administered according to various routes, typically by injection, such as local or systemic injection(s). For example, intratumoral injections are preferred for treating existing cancers. However, other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions of the preferred embodiments will include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds that fit the criteria of the claims are preferably also be considered when choosing an active compound.

The compound is preferably administered such that a therapeutically effective concentration of the compound is in contact with the affected cells of the body. The dose administered to a subject, particularly a human, in the context of the preferred embodiments is preferably sufficient to effect a therapeutic response in the subject over a reasonable period of time. The dose will be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds of the preferred embodiments are therapeutically effective at low doses. The generally useful dose range is from about 0.001 mM, or less, to about 100 mM, or more. Preferably, the effective dose range is from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds will be generally administered in low doses.

The compound can be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the preferred embodiments.

The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example *arachis* oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds of the preferred embodiments can also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

In some embodiments the composition can comprise, for example a topical formulation. In some embodiments, the topical formulation is a non-transdermal composition, formulated so as to not penetrate beyond the dermal layer. Non-transdermal formulations are known in the art, and include matrical or micellar solutions, bandages, wound dressings, aerosol sprays, foams, non-transdermal topical patches, tinctures, topical administrative agents and the like.

Pharmaceutical compositions of the preferred embodiments can also be in the form of oil-in-water emulsions. The oil phase can be a vegetable oil, for example olive oil or *arachis* oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

For all regimens of use disclosed herein for active agent, the daily oral dosage regimen will preferably be from about 0.01 to about 200 mg/Kg of total body weight. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. Preferably, the daily dosage for administration by injection, including intravenous, intramuscular, subcutaneous and parenteral injections, and use of infusion techniques will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily vaginal dosage regime will preferably be from 0.01 to 200 mg/Kg of total body weight. The daily topical dosage regimen will preferably be from 0.01 to 200 mg administered between one to four times daily. The concentration for vaginal dosage and topical dosage will preferably be that required to maintain a daily dose is of from 0.1 to 200 mg/Kg. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily inhalation dosage regimen will preferably be from 0.01 to 10 mg/Kg of total body weight. Preferably, the daily inhalation dosage regimen will preferably be from about 0.01, 0.05, 0.1, 0.5, to about 1, 2, 3, 4, 5, or 10, mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

The active compounds can be incorporated into pharmaceutical compositions suitable for administration to a subject, e.g., a human. Such compositions typically comprise the nucleic acid molecule, protein, modulator, or antibody and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the preferred embodiments. Supplementary active compounds can also be incorporated into the compositions. A pharmaceutical composition of the preferred embodiments is formulated to be compatible with its intended route of administration. Examples of routes of administration include parenteral, e.g., intravenous, intradermal, subcutaneous, oral (e.g., inhalation), transdermal, non-transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid, buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes) can also be used as pharmaceutically acceptable carriers. These can be prepared according to methods known to those skilled in the art.

It is especially advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the preferred embodiments, a therapeutically effective amount of one, two, or more of the active agents of the preferred embodiments is administered to a subject afflicted with a disease or disorder related to the aging of blood precursor cells, dermal epithelial precursor cells or intestinal epithelial precursor cells, or to a tissue which has such disease or disorder, or to a subject for whom weight control is weight reduction is indicated. The active agents of the preferred embodiments can be administered in accordance with the method of the preferred embodiments either alone of in combination with other known therapies. When co-administered with one or more other therapies, the active agents of the preferred embodiments can be administered either simultaneously with the other treatment(s), or sequentially. If administered sequentially, the attending physician will decide on the appropriate sequence of administering the active agents of the preferred embodiments in combination with the other therapy.

Generally, a therapeutically effective amount of active agent (i.e., an effective dosage) ranges from about 0.001 to 5000 mg/kg body weight, more preferably about 0.01 to 1000 mg/kg body weight, more preferably about 0.01 to 500 mg/kg body weight, more preferably about 0.01 to 250 mg/kg body weight, more preferably about 0.01 to 100 mg/kg body weight, more preferably about 0.001 to 60 mg/kg body weight, more preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount can include a single treatment or, preferably, can include a series of treatments. In a preferred example, a subject is treated in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage used for treatment can increase or decrease over the course of a particular treatment. Changes in dosage can result and become apparent from the results of diagnostic assays as described herein.

The preferred embodiments encompass one or more additional agents that modulate expression or activity of Cdc42 GTPase. An agent can, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In one embodiment, the additional agent can be a prenylation inhibitor, such as disclosed by U.S. Pat. Nos. 6,649,638, 5,420,245; 5,574,025; 5,523,430; 5,602,098; 5,631,401; 5,705,686; 5,238,922; 5,470,832; and 6,191,147, all of which are incorporated herein by reference in their entirety.

In another embodiment, the additional agent comprises one or more inhibitor of farnesyl protein transferase (FPTase), prenyl-protein transferase or geranylgeranyl-protein transferase as described in U.S. Pat. Nos. 6,572,850; 6,458,783; 6,423,751; 6,387,926; 6,242,433; 6,191,147; 6,166,067; 6,156,746; 6,083,979; 6,011,029; 5,929,077; 5,928,924; 5,843,941; 5,786,193; 5,629,302; 5,618,964; 5,574,025; 5,567,841; 5,523,430; 5,510,510; 5,470,832; 5,447,922, 6,596,735; 6,586,461; 6,586,447; 6,579,887; 6,576,639; 6,545,020; 6,539,309; 6,535,820; 6,528,523; 6,511,800; 6,500,841; 6,495,564; 6,492,381; 6,458,935; 6,451,812; 6,441,017; 6,440,989; 6,440,974; 6,432,959; 6,426,352; 6,410,541; 6,403,581; 6,399,615; 6,387,948;

6,387,905; 6,387,903; 6,376,496; 6,372,747; 6,362,188; 6,358,968; 6,329,376; 6,316,462; 6,294,552; 6,277,854; 6,268,394; 6,265,382; 6,262,110; 6,258,824; 6,248,756; 6,242,458; 6,239,140; 6,228,865; 6,228,856; 6,225,322; 6,218,401; 6,214,828; 6,214,827; 6,211,193; 6,194,438, which are specifically incorporated herein by reference in their entirety.

A "farnesyl protein transferase inhibitor" or "FPT inhibitor" or "FTI" is defined herein as a compound which: (i) potently inhibits FPT (but generally not geranylgeranyl protein transferase I) and (ii) blocks intracellular farnesylation of ras. FPT catalyzes the addition of an isoprenyl lipid moiety onto a cysteine residue present near the carboxy-terminus of the Ras protein. This is the first step in a post-translational processing pathway that is essential for both Ras membrane-association and Ras-induced oncogenic transformation. A number of FPT inhibitors have been reported, including a variety of peptidomimetic inhibitors as well as other small molecule inhibitors.

Farnesyl transferase inhibitors generally fall into two classes: analogs of farnesyl diphosphate; and protein substrates for farnesyl transferase. Farnesyl transferase inhibitors have been described in U.S. Pat. Nos. 5,756,528, 5,141,851, 5,817,678, 5,830,868, 5,834,434, and 5,773,455, all of which are incorporated herein by reference in their entirety. Among the farnesyl transferase inhibitors shown to be effective for inhibiting the transfer of the farnesyl moiety to Ras-related proteins are L-739,749 (a peptidomimetic analog of the C-A-A-X sequence), L-744,832 (a peptidomimetic analog of the C-A-A-X sequence), SCH 44342 (1-(4-pyridylacetyl)-4-(8-chloro-5,6 dihydro-IIH benzo[5,6]cyclohepta[1,2-b]pyridin-11-yhdene)piperidine), BZA-5B (a benzodiazepine peptidomimetic), FTI-276 (a C-A-A-X peptidomimetic), and B1086 (a C-A-A-X peptidomimetic). Administration of farnesyl transferase inhibitors (FTIs) is accomplished by standard methods known to those of skill in the art, most preferably by administration of tablets containing the FTI, and is expected to fall approximately within a range of about 0.1 mg/kg of body to weight to about 20 mg/kg of body weight per day.

In another embodiment, the additional agent comprises one or more inhibitor of geranylgeranyl-protein transferase (GGT) as have been described in U.S. Pat. No. 5,470,832 (Gibbs & Graham), which is incorporated herein by reference in its entirety. These compounds can be administered to an individual in dosage amounts of between 0.5 mg/kg of body weight to about 20 mg/kg of body weight. Alternatively, one or more inhibitors of isoprenylation, including farnesyl transferase (FT) inhibitors and/or geranylgeranyl transferase inhibitors (GGT) are administered to a patient.

In another embodiment, the additional agent comprises one or more toxins such as toxins A and B from *C. difficile* and *C. sordellii* lethal toxin (LT). In addition, Rac 1 and Rac2 can be inhibited when Rho is specifically ADP ribosylated by C3 enzyme, which is one of the botulinum toxins, and Staphylococcal toxin EDIN (Narumiya, S. and Morii, S., *Cell Signal*, 5, 9-19, 1993; Sekine, A. et al., *J. Biol. Chem.*, 264, 8602-8605, 1989, all of which are incorporated herein by reference in their entirety).

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the preferred embodiments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses can be determined using the assays described herein. When one or more of these small molecules is to be administered to a subject (e.g., a human) in order to modulate expression or activity of a polypeptide or nucleic acid of the preferred embodiments, a physician, veterinarian, or researcher can, for example, prescribe a relatively low dose at first, subsequently increasing the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Suitable dosage ranges for the active compound can vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages can be higher when the compounds are administered orally or transdermally as compared to, for example, i. v. administration. The compounds can be administered as a single bolus dose, a dose over time, as in i. v. or transdermal administration, or in multiple dosages.

The amount of active compound to be administered can vary according to the discretion of the skilled artisan. The amount of active compound to be administered to the recipient is within the ranges described above. However, the administration of such amounts will vary according to the standards set forth by clinicians in the field of stem cell enhancement therapy. Administration should generally occur daily following chemotherapy or other treatment for 1 or more days, preferably daily or intermittently for up to 200 days.

The dosage regimen for rejuvenation of blood precursor cells, dermal epithelial precursor cells or intestinal epithelial precursor cells or weight control with the active compounds is based on a variety of factors, including the type of injury, the age, weight, sex, medical condition of the individual, the severity of the condition, the route of administration, and the particular compound employed. Thus, the dosage regimen can vary widely, but can be determined routinely by a physician using standard methods. Dosage levels of the order of between 0.1 ng/kg and 10 mg/kg body weight of the active compounds per body weight are useful for all methods of use disclosed herein.

The treatment regime will also vary depending on the disease being treated, based on a variety of factors, including the type of injury, the age, weight, sex, medical condition of the individual, the severity of the condition, the route of administration, and the particular compound employed. For example, the active compounds are administered to an oncology patient for up to 30 days prior to a course of chemotherapy and for up to 60 days post-chemotherapy. The therapy is administered for 1 to 6 times per day at dosages as described above.

In a preferred embodiment, the active compound is administered subcutaneously. A suitable subcutaneous dose of the active compound is preferably between about 0.1 μg/kg and about 10 mg/kg administered twice daily for a time sufficient to increase rejuvenation of blood precursor cells, dermal epithelial precursor cells or intestinal epithelial precursor cells. This dosage regimen maximizes the therapeutic benefits of the treatments while minimizing the amount of agent needed. Such an application minimizes costs as well as possible deleterious side effects.

For subcutaneous administration, the active ingredient can comprise from 0.0001% to 10% w/w, e.g. from 1% to 2% by weight of the formulation, although it can comprise as much as 10% w/w, but preferably not more than 5% w/w, and more preferably from 0.1% to 1% of the formulation. In a most preferred embodiment, subcutaneous administration of between about 1 to 1000 μg/kg/day of the active compounds is initiated at between one week before to one week after administration of a cancer therapy (e.g., a chemotherapeutic agent).

In another preferred embodiment, a subject undergoes repeated cycles of treatment according to the method disclosed herein. Preferably, a subsequent treatment cycle commences only after the administration of the compounds disclosed herein have been terminated and the subject's blood cell counts (e.g., white blood cell count) have returned to a therapeutically acceptable level (as determined by the attending veterinarian or physician), permitting the repeated chemotherapy.

In all of these embodiments, the compounds can be administered prior to, simultaneously with, or subsequent to chemotherapeutic exposure or any other therapeutic exposure.

The active compounds can be administered by any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intraarterial, intramuscular, intrasternal, intratendinous, intraspinal, intracranial, intrathoracic, infusion techniques or intraperitoneally. In some embodiments, the active compounds are administered as a depot comprising a bio-compatible matrix formulated for continuous delivery of the agent in vivo. In some embodiments, the depot is formulated to degrade over time, thereby releasing the agent in a continuous or near-continuous manner. In some embodiments, the depot is formulated for release of the agent over the range of about 1 day to about 1, 2, 3, 4, 5, 6 months or more. In some embodiments, the depot can be an injectable depot for local administration. In some embodiments, the injectable depot is formulated for subcutaneous, intravenous, intraarterial, intramuscular, intrasternal, intratendinous, intraspinal, intracranial, intrathoracic, infusion techniques or intraperitoneallysubcutaneous, intravenous, intraarterial, intramuscular, intrasternal, intratendinous, intraspinal, intracranial, intrathoracic, infusion techniques or intraperitoneal injection. In some embodiments, the injectable depot is formulated for local injection at or near the stroma of the intestinal tract.

The active compounds can be made up in a solid form (including granules, powders or suppositories) or in a liquid form (e.g., solutions, suspensions, or emulsions). The compounds can be applied in a variety of solutions. Suitable solutions for use in accordance with the preferred embodiments are sterile, dissolve sufficient amounts of the peptide, and are not harmful for the proposed application. In this regard, the compounds disclosed herein are very stable but are hydrolyzed by strong acids and bases. The compounds are soluble in organic solvents and in aqueous solutions at pH 5-8.

The active compounds can be subjected to conventional pharmaceutical operations such as sterilization and/or can contain conventional adjuvants, such as preservatives, stabilizers, wetting agents, emulsifiers, buffers etc.

For administration, the active compounds are ordinarily combined with one or more adjuvants appropriate for the indicated route of administration. The compounds can be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the compounds disclosed herein can be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent can include time delay material, such as glyceryl monostearate or glyceryl distearate alone or with a wax, or other materials well known in the art.

Kits

In a further aspect, kits are provided for increasing rejuvenation of blood precursor cells, dermal epithelial precursor cells or intestinal epithelial precursor cells, wherein the kits comprise an effective amount of the active compounds for increasing rejuvenation of blood precursor cells, dermal epithelial precursor cells or intestinal epithelial precursor cells, or weight control of a subject, and instructions for using the amount effective of active compound as a therapeutic. In a preferred embodiment, the kit further comprises a pharmaceutically acceptable carrier, such as those adjuvants described above. In another preferred embodiment, the kit further comprises a means for delivery of the active compound to a subject. Such devices include, but are not limited to syringes, matrical or micellar solutions, bandages, wound dressings, aerosol sprays, lipid foams, transdermal patches, topical administrative agents, polyethylene glycol polymers, carboxymethyl cellulose preparations, crystalloid preparations (e.g., saline, Ringer's lactate solution, phosphate-buffered saline, etc.), viscoelastics, polyethylene glycols, and polypropylene glycols. The means for delivery can either contain the effective amount of the active compounds, or can be separate from the compounds, that are then applied to the means for delivery at the time of use.

In another aspect a method is disclosed that comprises pharmaceutical compositions for increasing rejuvenation of blood precursor cells, dermal epithelial precursor cells or intestinal epithelial precursor cells following cancer therapy (e.g., chemotherapy), comprising the active compounds disclosed herein, an amount effective for decreasing the growth or neoplastic cells of an anti-neoplastic agent, and a pharmaceutically acceptable carrier. According to this aspect, any cytotoxic agent can be included in the pharmaceutical composition, including, but not limited to, cyclophosphamide, taxol, 5-fluorouracil, adriamycin, cisplatinun, methotrexate, cytosine arabinoside, mitomycin C, prednisone, vindesine, carbaplatinum, and vincristine. The cytotoxic agent can also be an antiviral compound that is capable of destroying proliferating cells.

The compositions and preparations described preferably contain at least 0.1% of active compound. The percentage of the compositions and preparations can, of course, be varied, and can contain between about 2% and 60% of the weight of the amount administered. The amount of active compounds in such pharmaceutically useful compositions and preparations is such that a suitable dosage will be obtained.

One embodiment also pertains to kits useful in the methods. Such a kit contains an appropriate quantity of active compound, and other components useful for the methods. For example, a kit used to facilitate in vivo expansion of hematopoietic stem cells contains an appropriate amount of the active compound to facilitate rejuvenation, as well as an amount of the active compound to enhance the expansion of the stem cells by growth factors. Such a kit can also contain an appropriate amount of a growth factor.

The methods, kits, and pharmaceutical compositions of the present invention, by increasing white blood cell survival following chemotherapy and rejuvenation of blood precursor cells, dermal epithelial precursor cells or intestinal epithelial precursor cells, or weight control of a subject, significantly enhance the utility of presently available treatments for clinical chemotherapeutic treatments.

In addition, information regarding procedural or other details supplementary to those set forth herein, are described in cited references specifically incorporated herein by reference.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof Accordingly, the invention is not intended to be limited by the specific disclosures of preferred embodiments herein, but instead by reference to claims attached hereto.

The following examples provide illustrations of some of the embodiments described herein but are not intended to limit the invention.

EXAMPLE 1

Experimental Procedures

The following materials and methods were utilized to perform the experiments described in Examples 2-4.

Serial Competitive Transplantation

Bone marrow (BM) cells ($10^6$) from 4-6-week-old $Cdc42GAP_{+/+}$ and $Cdc42GAP_{-/-}$ mice and aged (20- to 26-month-old) C57BL/6 mice (donors, Ly5.2$^+$) were mixed with $10^6$ BM cells from young (2-4-month-old) BoyJ competitor mice (Ly5.1$^+$) and injected into the retro-orbital sinus of irradiated BoyJ recipient mice (Ly5.1$^+$) in 200 µl in PBS. Primary transplanted mice were sacrificed after 20 weeks and $2\times10^6$ BM cells from each recipient mouse were injected into a secondary pre-conditioned recipient BoyJ mouse. Serial BM transplantation experiments were repeated three times with a cohort of 4 to 5 recipient mice per donor.

For competitive LT-HSC transplantation, young (2-4-month-old) and aged (20-26-month-old) C57BL/6 mice (Ly5.2$^+$) were used as donors. 200 LT-HSCs were sorted into 96 multi-well plates and cultured (either in suspension or adherent to fibronectin) for 16 hrs in HBSS+10% FBS±CASIN (5 µM) in a water jacketed incubator at 37° C., 5% $CO_2$, 3% $O_2$. Stem cells were then mixed with $3\times10^5$ BM cells from young (2-4-month-old) BoyJ competitor mice (Ly5.1$^+$) and then transplanted into BoyJ recipient mice (Ly5.1$^+$).

Peripheral blood (PB) chimerism was determined by FACS analysis every 8 weeks. 24 weeks post primary transplants, $2\times10^6$ BM cells from an individual primary recipient mouse were injected into an individual secondary pre-conditioned recipient BoyJ mouse. Experiment was performed three times with LT-HSCs cultured in suspension and two times with LTHSCs cultured on a fibronectin-coated substrate without any difference in experimental outcome. Primary transplanted mice were regarded engrafted when PB chimerism was higher or equal to 1.0% and contribution was detected in all lineages. Secondary transplanted mice were regarded as engrafted when PB chimerism was higher or equal to 0.5% and contribution was detected in all lineages.

Flow Cytometry and Cell Sorting

PB and BM cell immunostaining was performed according to standard procedures and samples were analyzed on a LSRII flow cytometer (BD Biosciences). Lineage FACS analysis data are plotted as the percentage of B220+, CD3+ and Myeloid (Gr-1+, Mac-1+ and Gr-1+Mac-1+) cells among donor-derived Ly5.2$^+$ cells. As for early hematopoiesis analysis, mononuclear cells were isolated by low-density centrifugation (Histopaque 1083, Sigma) and stained with a cocktail of biotinylated lineage antibodies. After lineage depletion by magnetic separation (Dynalbeads, Invitrogen), cells were stained with anti-Sca-1 (clone D7) (eBioscience), anti-c-kit (clone 2B8) (eBioscience), anti-CD34 (clone RAM34) (eBioscience), anti-CD127 (clone A7R34) (eBioscience), anti-Flk-2 (clone A2F10) (eBioscience) and Streptavidin (eBioscience). Early hematopoiesis FACS analysis data were plotted as percentage of long-term hematopoietic stem cells (LTHSCs, gated as LSK $CD34_{-/low}Flk2_-$), short-term hematopoietic stem cells (ST-HSCs, gated as LSK $CD34_+Flk2_-$) and lymphoid-primed multipotent progenitors (LMPPs, gated as LSK $CD34_+Flk2_+$) (Adolfsson et al., 2005) distribution among donor-derived LSKs ($Lin_{neg}$c-kit$_+$sca-1$_+$ cells). LSK and common lymphoid progenitor cells (CLP, gated as Lin_c-Kit$_{-/low}$ Sca-1$_{-/low}$ IL7Rα$_+$) (Karsunky et al., 2008) were plotted as percentage among donor-derived $Lin_{neg}$ cells. In order to isolate LT-HSCs, lineage depletion was performed to enrich for lineage negative cells. Lineage negative cells were then stained as aforementioned and sorted using a BD FACS Aria I or a BD FACS Aria III (BD Bioscience).

Monoclonal antibodies to Ly5.2 (clone 104, eBioscience) and Ly5.1 (clone A20, eBioscience) were used to distinguish donor from recipient and competitor cells. For lineage analysis the antibodies used were all from eBioscience: anti-CD3e (clone 145-2C11), anti-B220 (clone RA3-6B2), anti-Mac-1 (clone M1/70) and anti-Gr-1 (clone RC57BL/6-8C5). Biotinilated antibodies used for lineage staining were all rat anti-mouse antibodies: anti-CD11b (clone M1/70), anti-B220 (clone RA3-6B2), anti-CD5 (clone 53-7.3) anti-Gr-1 (clone RB6-8C5), anti-Ter119 and anti-CD8a (Clone 53-6.7) (all from eBioscience).

Immunofluorescence Staining

Freshly sorted LT-HSCs were seeded on fibronectin-coated glass coverslips in HBSS+10% FBS. CASIN (referred to in (Peterson et al., 2006) as Pirl1-related compound 2) was obtained from Chembridge Corporation, and purified to greater than 99% by high-performance liquid chromatography. After 16 hours of incubation at 37° C., 5% $CO_2$, 3% $O_2$, cells were fixed with BD Cytofix Fixation Buffer (BD Biosciences).

After fixation cells were gently washed with PBS, permeabilized with 0.2% Tryton X-100 (Sigma) in PBS for 20 minutes and blocked with 10% Donkey Serum (Sigma) for 30 minutes. Primary and secondary antibodies incubations were performed for 1 hr at room temperature. Coverslips were mounted with ProLong Gold Antifade Reagent (Molecular Probes). The cells were coimmunostained with an anti-alpha tubulin antibody (Abcam, rat monoclonal ab6160) detected with an anti-rat AMCA-conjugated secondary antibody or an anti-rat DyLight 488-conjugated antibody (Jackson ImmunoResearch), an anti-Cdc42 antibody (Millipore, rabbit polyclonal) detected with an anti-rabbit DyLight 549-conjugated antibody (Jackson ImmunoResearch) and an anti-Pericentrin-2 antibody (Santa Cruz Biotechnology, goat polyclonal) detected with an anti-goat MCAconjugated antibody (Jackson ImmunoResearch). Samples were imaged with an AxioObserver Z1 microscope (Zeiss) equipped with a 63X PH objective. Images were analyzed with AxioVision 4.6 software. Alternatively, samples were analyzed with an LSM710 confocal microscope (Zeiss) equipped with a 63X objective. Primary raw data were imported into the Volocity Software package (Version 4.3, Improvision, UK) for further processing and conversion into 3-dimensional images. As for polarity scoring, the localization of each single stained protein was considered polarized when a clear asymmetric distribution was visible by drawing a line across the middle of the cell. A total of 50 to 100 LT-HSCs were singularly analyzed per sample. Data are plotted as percentage of the total number of cells scored per sample. Specificity of the anti-Cdc42 antibody in immunofluorescence was tested on LT-HSCs sorted from mice in which cdc42 was targeted deleted specifically in the hematopoietic system (Mx1-Cre; Cdc42flox/flox mice (Yang et al., 2007b)) (data not shown).

Mice

C57BL/6 mice (10-12-week-old) were obtained from Janvier. Aged C57BL/6 mice (20-26-month-old) were obtained from the divisional stock (derived from mice obtained from both. The Jackson Laboratory and Janvier). Congenic C57BL/6.SJL-Ptprca/Boy (BoyJ) mice were obtained from Charles River Laboratories or from the divisional stock (derived from mice obtained from Charles River Laboratories). Cdc42GAP mice were described previously (Wang et al., 2007). All mice were housed in the animal barrier facility under pathogen-free conditions at the University of Ulm. All mouse experiments were performed in compliance with the German Law for Welfare of Laboratory Animals and were approved by the Institutional Review Board of the University of Ulm.

Apoptosis and Cell Cycle staining

Hoechst/PY staining was performed as previously described (Passegue et al., 2005). Briefly, 25,000 FACS-sorted LT-HSCs were incubated for 16 hrs in HBSS+10% FBS±CASIN (5 μM) in a water jacketed incubator at 37° C., 5% CO2, 3% O2. Then HOECHST 33342 (Invitrogen) was added directly to the medium at a final concentration of 20 μg/ml and samples were kept in incubation at 37° C., 5% CO2, 3% O2 for 45 min. PironinY (Sigma-Aldrich) was then added at a concentration of 1 μg/ml, and cells were incubated for additional 15 minutes. Cells were resuspended and incubated with anti-Annexin V (BD Pharmingen) according to manufacturer's instruction, washed and immediately analyzed on a LSRII (BD Biosciences).

Western Blot and Cdc42-GTPase Effector Domain Pull-Down Assays

Relative levels of GTP-bound Cdc42 were determined by an effector pull-down assay. Briefly, lineage depleted BM cells ($10^6$) were lysed in a Mg2+ lysis/wash buffer (Upstate cell signaling solutions) containing 10% glycerol, 25 mM sodium fluoride, 1 mM sodium orthovanadate and a protease inhibitor cocktail (Roche Diagnostics). Samples were incubated with PAK-1 binding domain/agarose beads and bound (activated) as well as unbound (non-activated) Cdc42 fractions were probed by immunoblotting with an anti-Cdc42 antibody (Millipore, rabbit polyclonal). Activated protein was normalized to total protein and/or β-actin (Sigma) and the relative amount was quantified by densitometry.

Statistical Analyses

A paired Student's t test was used to determine the significance of the difference between means of two groups. One-way Anova or two-way Anova were used to compare means among three or more independent groups. Bonferroni post-test to compare all pair of data set was determined when overall p value was <0.05. All statistical analyses were determined with Prism 4.0c version.

EXAMPLE 2

Constitutively Increased Cdc42 Activity Results in Premature Aging of Young HSCs To test the role of Cdc42 activity in cell-intrinsic aging of HSCs, it was determined whether constitutively increased Cdc42 activity in young HSCs by genetic means is sufficient to cause pre-mature aging of HSCs, using as a model HSCs deficient for the p50RhoGAP protein (Cdc42GAP$_{-/-}$ mice). This RhoGAP protein is a highly selective negative regulator of Cdc42-activity, and therefore Cdc42GAP$_{-/-}$ mice present with a gain-of-activity specific for Cdc42 in all tissues, including primitive hematopoietic cells (FIG. 5H). Cdc42GAP$_{-/-}$ mice present with premature aging-like phenotypes in multiple tissues and cell types. As for the hematopoietic system, a significant increase in myeloid cell frequency and a decrease in T cell frequency in PB was detected in young Cdc42GAP$_{-/-}$ mice as well as an overall decrease of B-cell frequency and an increase in myeloid cell frequency in BM, which are phenotypes consistent with aging in hematopoiesis (FIG. 5I). To determine the functional status of Cdc42GAP$_{-/-}$ HSC, competitive serial transplant assays were performed (FIG. 1A), which are regarded as a gold standard for determining stem cell intrinsic parameters of HSC aging.

Results demonstrated that young Cdc42GAP$_{-/-}$ HSCs were similar to aged and distinct from young control Cdc42GAP$_{+/+}$ HSCs with respect to a decreased contribution to the B-cell lineage and an increased contribution to the myeloid cell lineage in PB (FIGS. 1B-C) and in BM (FIG. 5J-K) in both primary and secondary recipients. Aged HSCs, contributed significantly more to the pool of LT-HSCs compared to young Cdc42GAP$_{+/+}$ controls, while the contribution of chronologically young Cdc42GAP$_{-/-}$ LT-HSCs was almost identical to aged HSCs both in primary and in secondary recipients (FIG. 1D-F). There was also a significant decrease in the contribution of aged and Cdc42GAP$_{-/-}$ HSCs to LMPPs in secondary recipients compared to young Cdc42GAP$_{+/+}$ cells (FIG. 1F). Thus, chronologically young Cdc42GAP$_{-/-}$ HSCs are functionally similar to chronologically aged HSCs in competitive transplantation assays, implying a mechanistic role for elevated Cdc42 activity in cell-intrinsic aging of HSCs.

EXAMPLE 3

Figure 2:
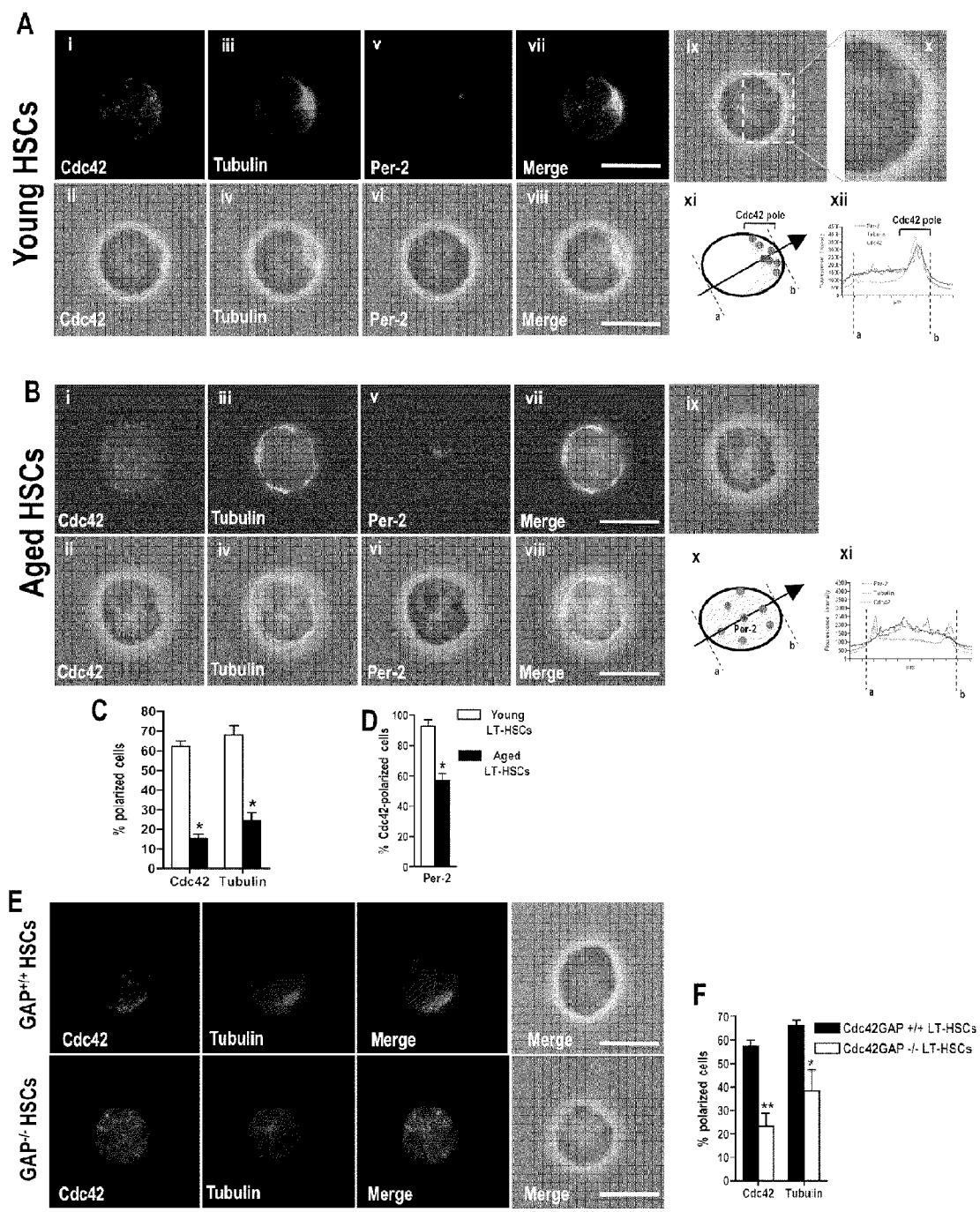
FIG. 2. Increased Cdc42 activity correlates with a de-polarized phenotype in LTHSCs. (A), Representative distribution of Cdc42, tubulin and pericentrin-2 (Per-2) in young LT-HSCs determined by IF. Pictures are shown on a dark background (panels i, iii, v and vii) or as overlap with the phase contrast picture (panels ii, iv, vi and viii). Bar=5 μm. Panel ix and x show Cdc42 (red) and Per-2 (blue) distribution over the phase contrast picture. Panel xi: schematic presentation of a representative distribution of Cdc42 in young LT-HSCs (Per-2, blue dot; Cdc42, red dots). The arrow indicates the direction from "a" to "b" followed for determining fluorescence intensity in panel xii. Panel xii: representative fluorescence intensity plot obtained by collecting pixel intensity through the section of the cell as indicated in xi. (B), Representative distribution of Cdc42, tubulin and Per-2 in aged LT-HSCs determined by IF. Pictures are shown on a dark background (panels i, iii, v and vii) or as overlap with the phase contrast picture (panels ii, iv, vi and viii). Bar=5 μm. Panel ix shows Cdc42 (red) and Per-2 (blue) distribution over the phase contrast picture. Panel x: schematic presentation of a representative distribution of Cdc42 in aged LT-HSCs (Per-2, blue dot; Cdc42, red dots). The arrow indicates the direction from "a" to "b" followed for determining fluorescence intensity in panel xi. Panel xii: representative fluorescence intensity plot obtained by collecting pixel intensity through the section of the cell as indicated in x. (C), Percentage of young and aged LT-HSC cells with a polar distribution of Cdc42 and tubulin. Shown are mean+1 S.E., n=10; ~500-700 cells scored per sample in total. * p<0.001. (D), Percentage of Per-2 polarized cells of Cdc42 polarized young and aged LT-HSCs. Cdc42-polarized cells were analyzed for Per-2 localization and scored positive when Per-2 was found at the Cdc42-pole. Shown are mean+1 S.E., n=4, ~150-250 cells scored per sample in total. * p<0.05. (E), Representative distribution of Cdc42 and tubulin in young Cdc42GAP$_{+/+}$ and Cdc42GAP$_{-/-}$ LT-HSCs. Pictures are shown on a dark background (panels i-vi) or as overlap with the phase contrast picture (panels vii and viii). Bar=5 μm. (F), Percentages of young Cdc42GAP$_{+/+}$ (WT Control) and Cdc42GAP$_{-/-}$ LT-HSC cells with a polar distribution of Cdc42 and tubulin. Shown are mean mean+1 S.E., n=4, ~200-300 cells scored per sample in total. ** P<0.01, *P<0.05.
Figure 6:
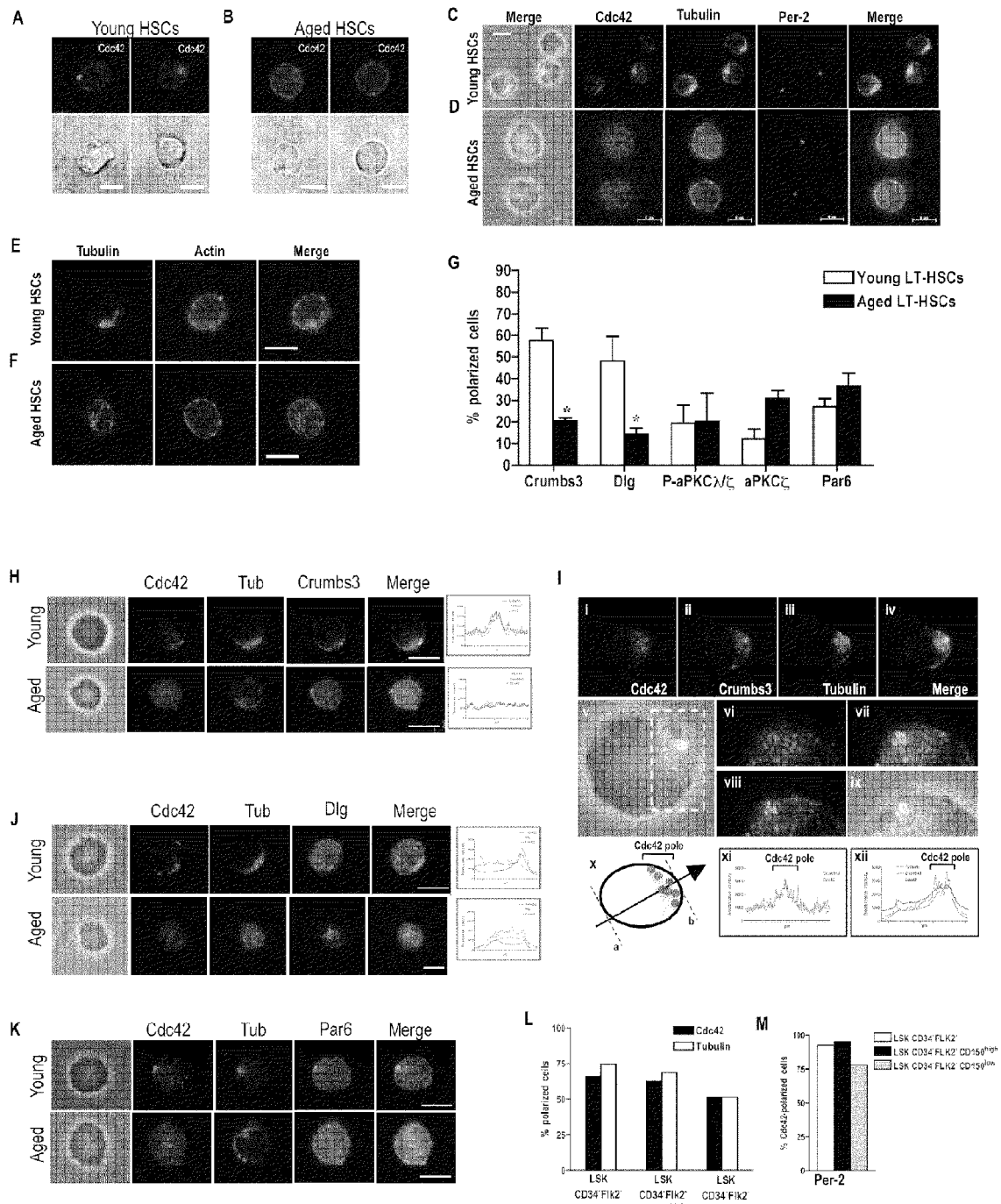
FIG. 6. Young LT-HSCs show a polar distribution of Cdc42, tubulin, Dlg and Crumbs3 but not of actin, Par6 and aPKCξ while aged LT-HSCs present with an overall apolar distribution. (A-B), Cdc42 localization in young (A) and aged (B) LT-HSCs as determine by confocal microscopy. Bar=5 μm. (C), Representative pictures of a group of three polarized young LT-HSCs stained for Cdc42, Tubulin and Perincentrin-2. Bar=5 μm. (D), Representative pictures of two apolar aged LT-HSCs stained for Cdc42, Tubulin and Perincentrin-2. Bar=5 μm. (E-F), Representative distribution of tubulin and actin in young (E) and aged (F) LT-HSCs. Bar=5 μm. (G), Percentage of young and aged LT-HSCs with a polar distribution of Crumbs3, Dlg, phospho-aPKCξ (P-aPKCξ), total aPKCξ and Par6. Each cell was singularly analyzed and scored for proteins distribution. Shown are mean values+1 S.E., n=3. (H), Representative distribution of Cdc42, tubulin and Crumbs3 in young and aged LT-HSCs determined by IF. Bar=5 μm. The graphs show a representative respective fluorescence intensity plot obtained by collecting pixel intensity through the circumference of the cell. (I), Representative distribution of Cdc42, tubulin and Crumbs3 in young LT-HSCs determined by IF. Pictures are shown on a dark background (panels i, ii, iii and iv and vii) and the merge is shown also as overlap with the phase contrast picture (panels v). Bar=5 μm. Panels vi to ix shows the detail marked in panel v. Panel x: schematic presentation of a representative distribution of Cdc42 in young LT-HSCs (Cdc42, red dots). The arrow indicates the direction from "a" to "b" followed for determining fluorescence intensity in panel xii. Panel xi: representative fluorescence intensity plot obtained by collecting pixel intensity through the circumference of the cell. Panel xii: representative fluorescence intensity plot obtained by collecting pixel intensity through the section of the cell as indicated in xi. (J), Representative distribution of Cdc42, tubulin and Dlg in young and aged LT-HSCs determined by IF. Bar=5 μm. The graphs show a representative respective fluorescence intensity plot obtained by collecting pixel intensity through the section of the cell. (K), Representative distribution of Cdc42, tubulin and Par6 in young and aged LT-HSCs determined by IF. Bar=5 μm. (L), Percentage of cells with a polar distribution of Cdc42 and tubulin in LT-HSCs, in LTHSCs CD150high and in LT-HSCs $CD150_{low}$ cells. The experiment was repeated twice with similar results, shown are mean values. (M), Percentage of cells with a polar distribution of Per-2 among LT-HSCs, LT-HSCs CD150high and LT-HSCs $CD150_{low}$ cells with a polar distribution of Cdc42. The experiment was repeated twice, shown are mean values.

Increased Cdc42 Activity in HSC Correlates with a De-Polarized Phenotype in LT-HSC In *D. melanogaster*, the age-associated loss of germ-line stem cell function correlates with loss of cell polarity. Further, a reduction in the frequency of cells with a polar distribution of microtubules among aged early hematopoietic progenitor cells (LSK cells) has been observed, suggesting a role for changes in cell polarity in aging of HSCs. Cdc42 activity has been implicated in the regulation of polarity in fibroblasts and epithelial cells and in the maintenance of polarity and stemness in neuronal stem cells. Therefore, it was tested whether aged HSCs alter their polarity status upon aging, and whether Cdc42 activity might be involved in regulating such changes. To test this, the localization of Cdc42, which in itself is a cell polarity marker, and tubulin was initially determined in LT-HSCs in single-cell immunofluorescence (IF) analyses. Interestingly, in the majority of young LTHSCs, Cdc42 and tubulin were asymmetrically distributed and were found at the same location inside the cell (FIGS. 2A and C, FIGS. 6A and C). This highly asymmetric localization of Cdc42 and tubulin did not correlate with the side of the cell bound to the substrate nor with an uneven distribution of the whole cytoplasm, as for example F-actin always showed a cortical and unpolarized distribution staining also the opposite side of the cell (FIG. 6E-F). The asymmetry was oriented along the xy plane on one the side of the nucleus where also the centrosome was localized (FIG. 2A, panels ix-xii). Therefore, in young LT-HSCs, Cdc42 and the microtubules were highly concentrated in the immediate pericentriolar zone and in the cytoplasmatic space along the nucleus/centrosome/cell membrane axis (FIGS. 2A and D). In contrast, Cdc42 and tubulin were distributed throughout the cell body in an unpolarized fashion in aged LT-HSCs (FIG. 2B-C, FIGS. 6B, D and F) and the centrosome was mostly found in the middle of the cell, oriented perpendicularly to the nucleus along the z-axis (FIG. 2B panels ix-xi, FIG. 2D). Similar results (young HSCs polar, aged HSCs apolar) were also obtained by analyzing additional established cell polarity markers like Crumbs3 (FIGS. 6G-I) and DgI (FIGS. 6G and J), while Par6 (FIGS. 6G and K) and the aPKCζ (FIG. 6G) did not follow this pattern. In summary, young HSCs present with a polar phenotype similar to the one previously described for memory T-cells—another non-tissue resident hematopoietic cell-type with a high proliferative potential—which is lost upon aging.

Recently CD150 expression was described as a marker for functionally distinct subpopulations within the pool of LT-HSCs. To test whether the polarity phenotype identifying phenotypically different type of LT-HSCs (polar vs. apolar) might thus constitute another surrogate marker for the distinct cell subsets stained by CD150 expression, the following experiments were performed. The frequency of young LT-HSCs polarized for Cdc42 and tubulin though was independent of the expression of CD150 on LT-HSCs (FIG. 6L-M). Consistent with a critical role of elevated Cdc42 activity in age-associated phenotypes like apolarity, IF staining revealed that the majority of chronologically young Cdc42GAP$_{-/-}$ LT-HSCs, which functionally resemble aged LT-HSCs, were apolar with respect to Cdc42 and tubulin distribution (FIG. 2E-F). These data identify Cdc42 as a novel polarity protein in LT-HSCs, show distinct polarity phenotypes in young and aged LTHSCs and support at a role for Cdc42 activity in the regulation of LT-HSC polarity.

EXAMPLE 4

Pharmacological Reduction of Cdc42 Activity Rejuvenates Aged LT-HSCS

The data from the previous examples imply that the aging-associated increase in Cdc42 activity might be the underlying stem-cell intrinsic molecular mechanism resulting in both apolarity and impaired function of LT-HSCs with age. To test whether inhibiting Cdc42 activity in aged LT-HSCs to the level in young LT-HSCs by pharmacological means might be a possible approach to at least in part revert apolarity as well as the impaired function of aged LT-HSCs, additional experiments were performed.

Figure 7:
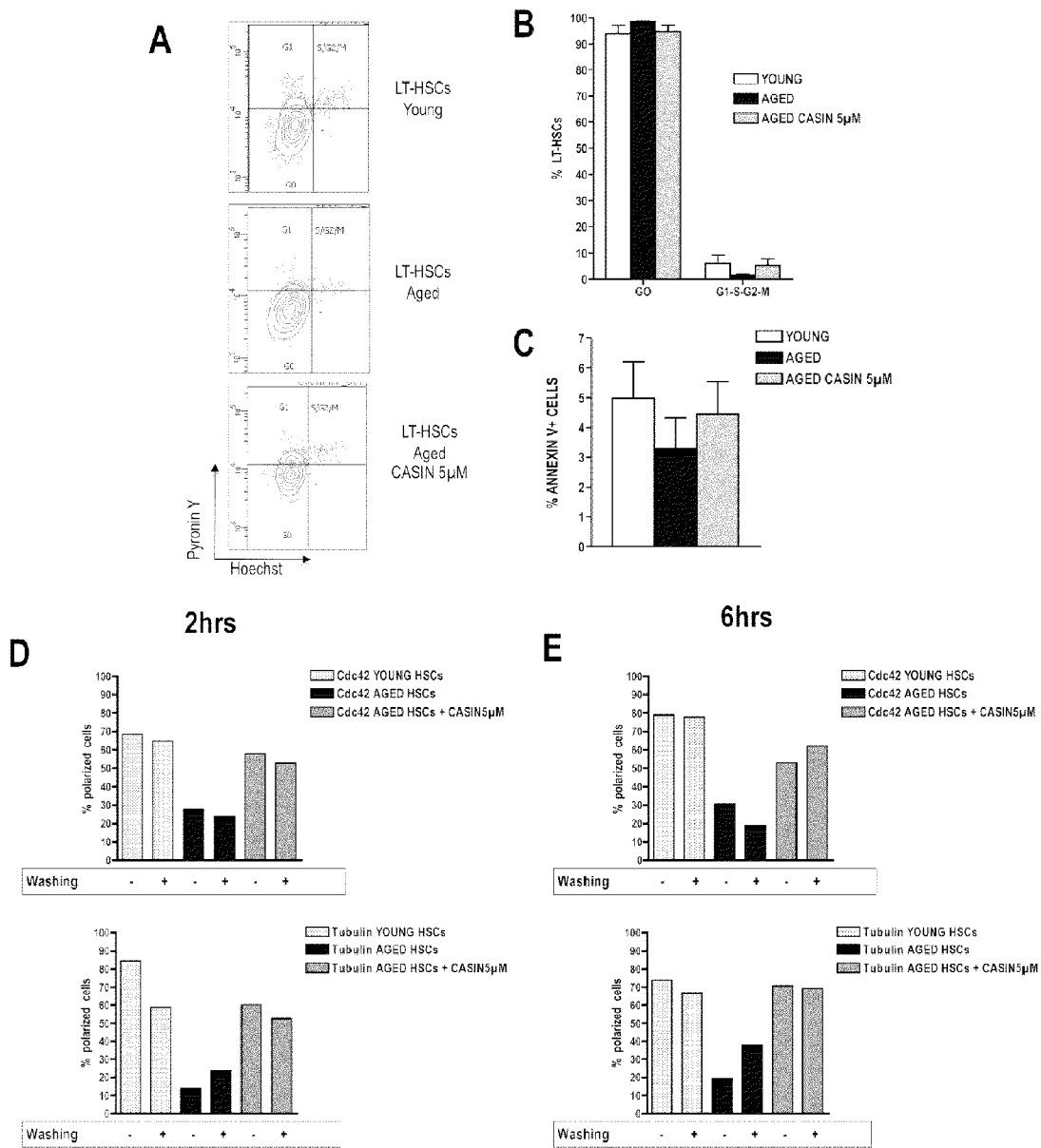
FIG. 7. CASIN treatment doesn't alter cell cycle and apoptotic parameters in aged LT-HSCs. (A-B), Representative FACS densitometry plots (A) and quantification (B) of young LT-HSCs, aged LT-HSCs and aged LT-HSCs treated with 5 μM CASIN in $G_0$, $G_1$ and $S/G_2/M$ phases of the cell cycle as determined by PyroninY and Hoechst staining. Shown are mean values+1 S.E., n=3. (C), Frequency of AnnexinV+(apoptotic) LT-HSCs among young LT-HSCs, aged LT-HSCs and aged LTHSCs treated with 5 μM CASIN. Shown are mean values+1 S.E., n=3. (D-E), Percentages of young, aged and aged LT-HSCs treated with CASIN that present with a polar distribution of Cdc42 and tubulin, 2 (D) and (E) 6 hours after washing/withdrawal of CASIN. Each cell was singularly analyzed and scored for Cdc42 and tubulin polar distribution. The experiment was performed twice with similar results.

To exclude stem cell extrinsic effects and focus on cell intrinsic mechanisms, LT-HSCs from aged mice were treated in vitro with a selective Cdc42 activity inhibitor termed CASIN. Treatment with CASIN (5 μM) reduced the elevated level of active Cdc42 observed in aged primitive hematopoietic cells to the level observed in young cells (FIG. 3A-B). CASIN treatment did not alter cell cycle status or apoptosis in aged LT-HSCs (FIG. 7A-C). In response to treatment with CASIN, LT-HSCs from aged mice showed a dose-dependent increase in the percentage of polarized cells, becoming progressively indistinguishable from young cells (FIG. 3C-D). These data demonstrate that elevated Cdc42-GTP levels in aged LT-HSCs cell-intrinsically regulate both Cdc42 and tubulin distribution and that the apolar distribution of these proteins can be reverted to a polar one by decreasing Cdc42 activity. Thus, CASIN treatment reverted aged LT-HSCs to young HSCs with respect to the polarity phenotype.

Figure 4:
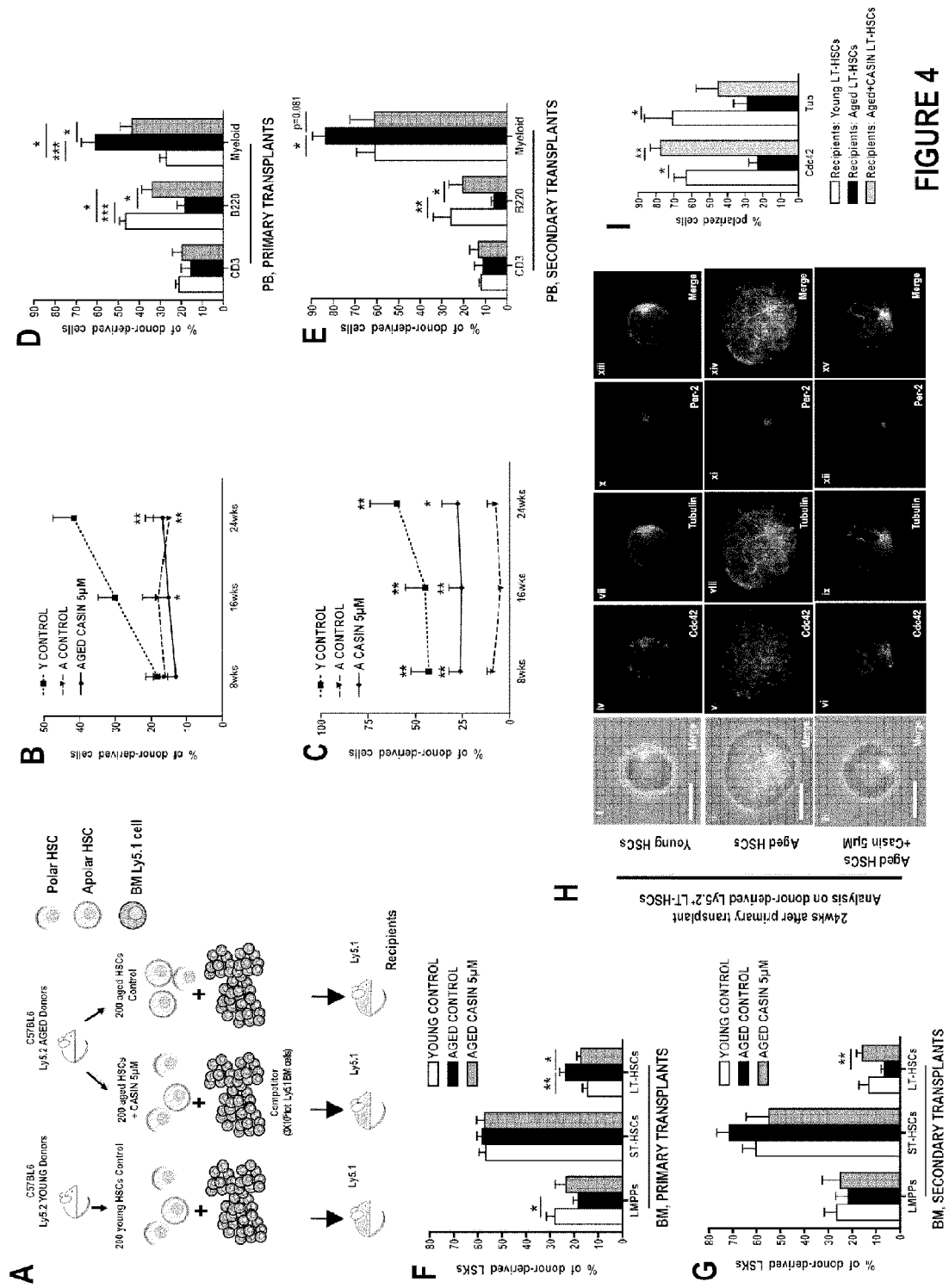
FIG. 4. Pharmacological targeting of Cdc42 activity rejuvenates LT-HSCs function. (A), Schematic representation of the experimental setup. 200 aged and young donor (Ly5.2$^+$) LT-HSCs were cultured for 16 hrs as indicated and subsequently transplanted into recipient (Ly5.1$^+$) mice along with 3×10$_5$ BM competitor (Ly5.1+) cells. 24 wks post transplant recipient mice were sacrificed and secondary transplants were performed. (B-C), Percentage of donor contribution (Ly5.2$^+$ cells) contribution to total WBC in PB 8, 16 and 24 wks post transplant in primary (B) and secondary (C) transplants. Shown are mean values+1 S.E.; ** p<0.01 and * p<0.05 vs young control in B; * p<0.001,  p<0.01, * p<0.05 vs aged control in C. (D-E), Percentage of B220+, CD3+ and myeloid cells among donor-derived Ly5.2$^+$ cells in PB 24 weeks after primary (D) and secondary (E) transplants. * p<0.05,  p<0.01, * p<0.001; shown are mean values+1 S.E. (F-G), Percentage of LT-HSCs, ST-HSCs and LMPPs cells in BM among donor-derived LSKs cells 24 weeks after primary (F) and secondary (G) transplants.  p<0.01; shown are mean values+1 S.E. Data is based on five (primary transplants) and four (secondary transplants) experimental repeats with 5 recipient mice per group (e.g. n=25 for primaries and n=20 for secondary transplants). (H), Representative distribution of Cdc42, tubulin and Per-2 in donor-derived LT-HSCs sorted from young, aged and aged CASIN treated LT-HSC recipient mice 24 weeks post transplant. Shown are overlaps with the phase contrast picture (panels i-iii) or cells on a dark background (panels iv-xv). Bar=5 μm. (I), Percentage of donor-derived LTHSCs polarized for Cdc42 and tubulin sorted 24 weeks post transplant from recipient animals competitively reconstituted with young, aged and aged CASIN treated LT-HSC. Shown are mean values+1 SEM, n=3, ~50 cells scored per sample in total.  p<0.01, * p<0.05.
Figure 8:
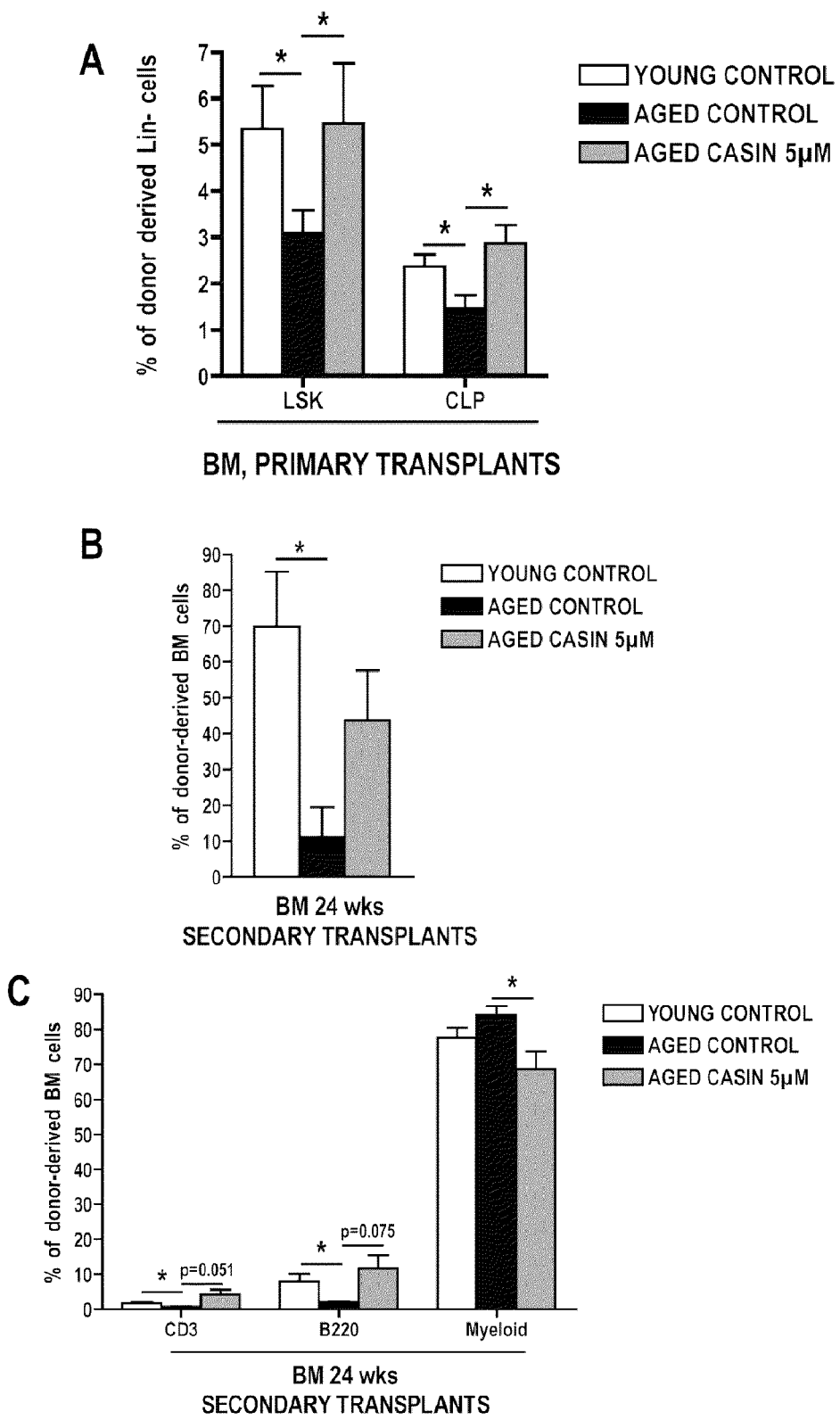
FIG. 8. Pharmacological targeting of Cdc42 activity rejuvenates LT-HSC function. 200 aged and young donor (Ly5.2$^+$) LT-HSCs were cultured for 16 hrs as indicated and subsequently transplanted into recipient (Ly5.1$^+$) mice with $3 \times 10_5$ BM competitor (Ly5.1$^+$) cells. 24 wks post transplant recipient mice were sacrificed and secondary transplants were performed. (A), Percentage of LSKs and CLPs among donor-derived Lin_ cells 24 weeks post primary transplants. * P<0.05; Shown are mean values+1 S.E. (B), Percentage of donor cells (Ly5.2$^+$ cells) in BM 24 wks post secondary transplant. Data Shown are mean values+1 S.E.; * P<0.05. (C), Percentage of B220+, CD3+ and Myeloid cells among donor-derived Ly5.2$^+$ cells in BM 24 weeks post secondary transplant. * P<0.05; Shown are mean values+1 S.E. Data are based on five (primary transplants) and four (secondary transplants) experimental repeats with 5 recipient mice per group (e.g. n=25 for primary and n=20 for secondary transplants).

Finally, it was determined whether inhibition of Cdc42 activity in aged LT-HSCs via CASIN treatment could revert at least in part the altered function of aged LT-HSCs, and thus rejuvenate old stem cell to become functionally younger. Although CASIN acts transiently on Cdc42 activity, surprisingly the increase in the percentage of polar cells among aged LT-HSCs induced by CASIN in vitro remained stable for at least up to 6 hours after CASIN withdrawal (FIG. 7D-E), implying a kind of "polarity memory" upon transient reduction of Cdc42 activity in aged LT-HSCs, which might allow for continuation of the new polar phenotype and the associated function(s) upon transplantation into recipient animals. In subsequent competitive serial transplant experiments, 200 aged LT-HSCs treated with 5 μM CASIN overnight were competitively transplanted into young recipients and compared to transplants with young and aged untreated LT-HSCs (FIG. 4A). In primary recipients, overall donor engraftment after 8 weeks was similar in young, aged and aged CASIN treated LT-HSCs (FIG. 4B), supporting that CASIN treatment did not alter homing of LT-HSCs. Remarkably, CASIN treatment of aged LT-HSCs resulted in an increase in contribution to the B-cell compartment in PB and a reduced contribution to the myeloid lineage (FIG. 4D). In addition, CASIN treatment increased the contribution to LSK and common lymphoid progenitor (CLP) populations to a level indistinguishable from young LT-HSCs (FIG. 8A).

The frequency of donor-derived LT-HSCs among donor-derived LSKs was, as anticipated, doubled in aged control recipients, while upon CASIN treatment this frequency was significantly reduced (FIG. 4F). In addition, upon secondary transplant CASIN treated LT-HSCs presented with an elevated overall regenerative capacity compared to aged LT-HSCs, as indicated by increased and stable chimerism in PB (FIG. 4C). Moreover, CASIN treated aged LT-HSCs proved to be indistinguishable from young LT-HSCs with respect to B-cell and myeloid engraftment in PB and BM (FIG. 4E and FIGS. 8B-C) and, importantly, with respect to the contribution to the LT-HSC pool in BM (FIG. 4G). Finally, the frequency of polar donor-derived LT-HSCs in recipients transplanted with aged, aged CASIN treated and young primary LT-HSCs was determined 24 weeks post transplantation. The data indicate that the percentage of donor-derived polar LT-HSCs in recipients transplanted with aged CASIN treated LT-HSC was similar to the frequency found in young controls and significantly increased, at least with respect to Cdc42 localization, compared to the frequency found in aged untreated controls, implying a lasting effect of transient CASIN treatment on LT-HSC polarity (FIG. 4H-I). In summary, these data identify elevated Cdc42 activity as key modulator of a molecular pathway driving intrinsic mechanisms of stem cell aging. Furthermore, these results demonstrate that lowering Cdc42 activity by CASIN treatment rejuvenated aged LT-HSCs with respect to function (lineage skewing, stem cell contribution and regenerative capacity) and phenotypic (polarity) parameters.

The foregoing data demonstrate a critical mechanistic role of Cdc42 activity in HSC aging and identify it as a target to pharmacologically rejuvenate stem cell intrinsic age-associated phenotypes of LT-HSCs. The differences in polarity between young and aged LT-HSC with respect to Cdc42 and tubulin further support a novel conclusion in which aging-associated changes in LT-HSC self-renewal and differentiation are possibly regulated by changes in stem cell polarity.

EXAMPLE 5

In Vivo Rejuvenation of Skin and Intestinal Epithelium

To test the extent to which CASIN rejuvenates skin and intestinal epithelium in vivo, aged (22-24 month old B1 6) and young (10-12 week old B1 6) mice were injected with CASIN twice daily (2.4 mg/Kg in PBS and 15% EtOH). A group of control mice in each age group were not given the drug. The injections were given 6 hours apart for 5 days. After 28 days, the mice were sacrificed and skin and intestinal samples were processed for immunohistochemistry.

Figure 9:
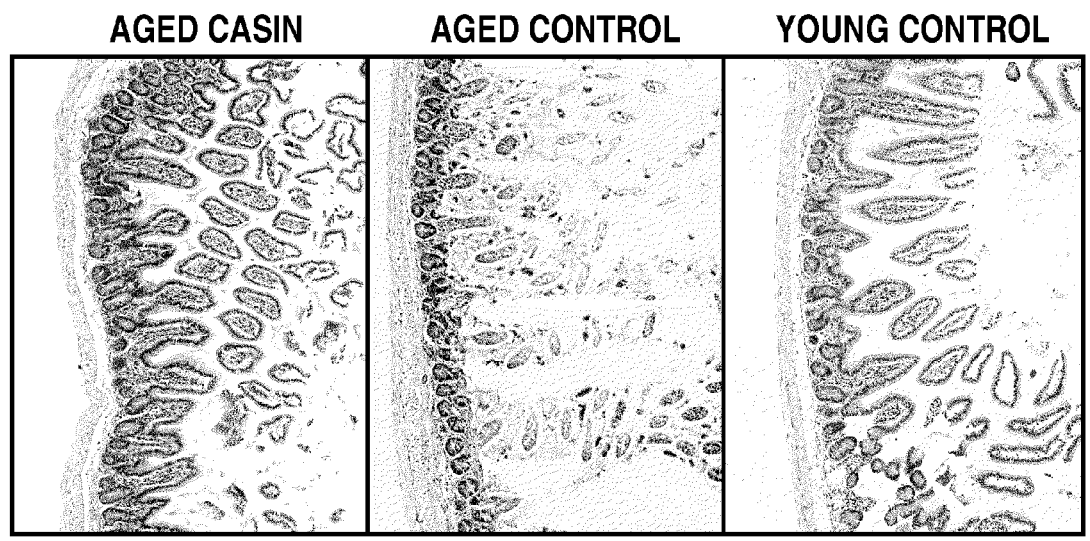
FIG. 9. Immunohistochemical data showing intestinal epithelium in young mice, aged untreated mice, and aged mice treated with CASIN.
Figure 10:
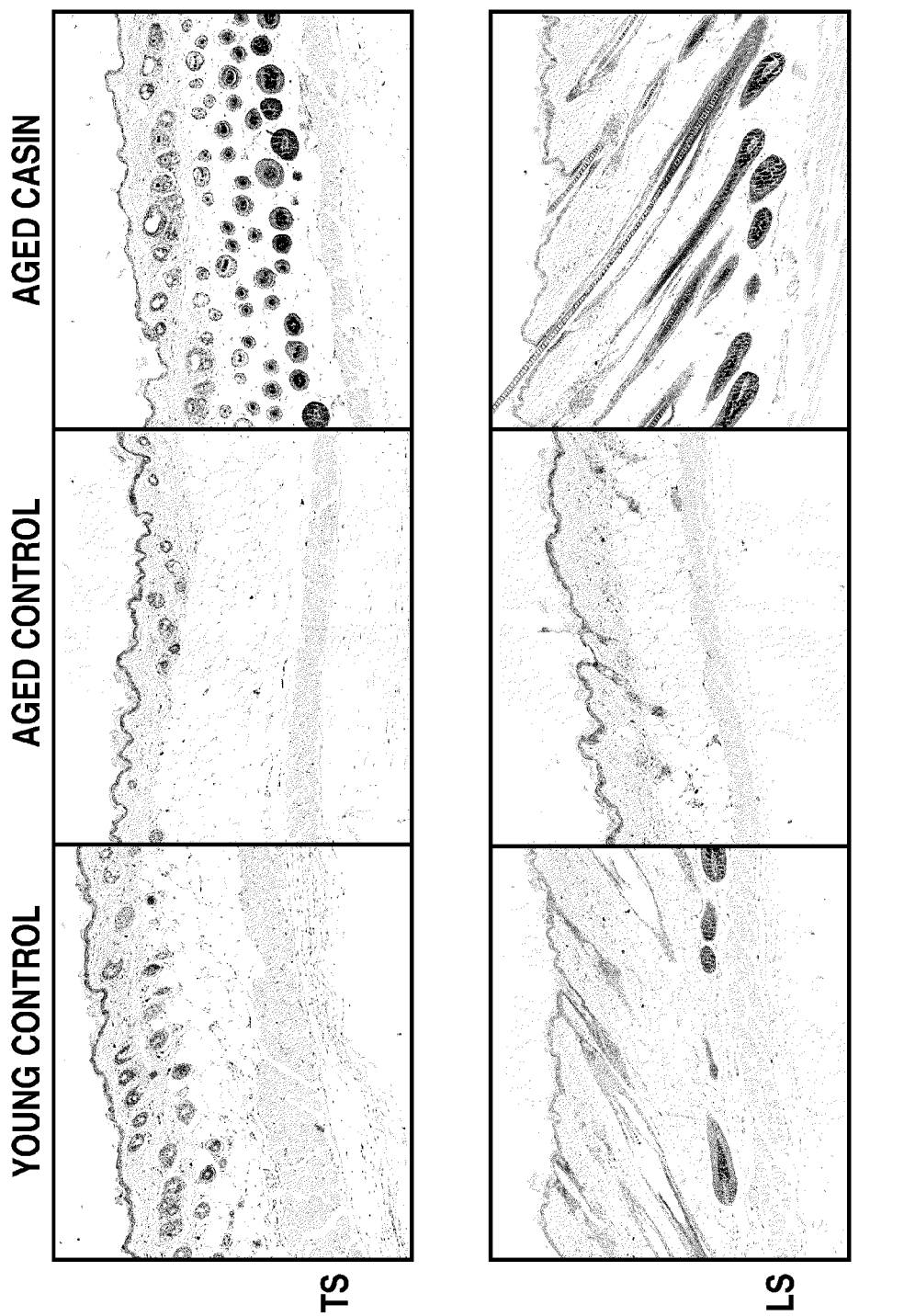
FIG. 10. Immunohistochemical data showing skin epithelium epithelium in young mice, aged untreated mice, and aged mice treated with CASIN. Both transverse section (TS) and longitudinal section (LS) are shown.

The results are shown in FIGS. 9 and 10. As set forth in FIG. 9, intestinal epithelium in aged mice treated with CASIN shows marked improvement in the shape, number and density of crypts, compared to untreated aged mice. The CASIN-treated samples resemble those of young mice much more than the controls, demonstrating the rejuvenating effects of in vivo administration of CASIN on intestinal epithelium, and indicating that those effects persist long after treatment is discontinued.

As set forth in FIG. 10, skin samples in aged mice treated with CASIN shows marked improvement in the number and density of hair follicles, compared to untreated aged mice. The CASIN-treated samples resemble those of young mice much more than the controls, demonstrating the rejuvenating effects of in vivo administration of CASIN on skin epithelium, and indicating that those effects persist long after treatment is discontinued.

EXAMPLE 6

In Vivo Rejuvenation of HSC

To test the extent to which CASIN rejuvenates HSC in vivo, aged (20+ months old mice) are given CASIN i. v. or i.p. twice daily for 28 days and compared to young as well as aged solvent injected control groups. In 28 days most of the HSCs cycle at least once in vivo. Subsequently, PB is harvested every 14 days for a total of 2 months and differential blood counts (myeloid cells, lymphoid cells, red blood cells etc) are determined by hemavat counting and flow cytometry. At 3 months post CASIN treatment, when hematopoesis should be fully supported by stem cell activity of the CASIN exposed HSCs, animals are sacrificed and the number of early hematopoietic progenitor cells (Lineage$^{neg}$c-Kit$^+$Sca-1$^+$ or LSK), long-term repopulating-HSC (LSKCD34$^{low/-}$Flk-2$^-$, LT-HSC), lymphoid-primed multipotent progenitors (LMPPs, LSKCD34$^+$Flk-2$^{+11, 23, 24}$) are determined.

Separately, to investigate the effect of CASIN on stem cell fitness and lineage differentiation, standard competitive transplantation assays are performed using the syngeneic CD45.1/CD45.2 surface marker system to differentiate donor from recipient cells. Sorted C57BL/6 CD45.2+LT-HSCs from CASIN-treated aged animals, as well as from the control groups, are then be transplanted with competitor BM CD45.1+ cells into syngeneic BoyJ CD45.1 recipients (50 HSCs with 4×10$^5$ competitor CD45.1+BM cells). Lineage chimerism (myeloid, B- and T-lymphoid) in peripheral blood (PB) is then determined up to 24-weeks post-transplant. The number of donor-derived LSK or LT-HSC lineages are determined in order to assess possible effect on self-renewal in BM, as well as the polarity properties for assessing a possible restoration of the polarized distributions of key markers of polarity. The results demonstrate that the rejuvenating effects of in vivo administration of CASIN persist long after treatment is discontinued.

Hematopoietic parameters in CASIN-treated aged (20+ months old) animals are similar to that of the young (2-3 months old) animals, and HSCs from CASIN-treated aged animals show in competitive transplant assays a chimerism that is greater than the overall chimerism supported by aged HSCs and similar to that observed for young HSCs, should CASIN be able to rejuvenate aged HSCs. Further, the preferential differentiation towards the myeloid lineage is ameliorated in CASIN-treated aged HSCs. These studies establish CASIN targeting as a viable approach to rejuvenate the aged hematopoietic system.

EXAMPLE 7

Whole Genome Profiling of Rejuvenated HSC

Aged HSCs have distinct whole genome expression profiles. To define the effect of Cdc42 inhibition by CASIN on molecular pathways regulating HSCs, cDNA was derived from linearly amplified RNA from CASIN-treated or untreated aged or young HSCs, using tested amplification, array hybridization and bioinformatic analysis services provided by the company Miltenyi. The goal of these experiments was to identify changes in whole genome expression patterns or in functionally defined groups of genes, rather than changes in individual genes. Differences in expression of functional gene groups was confirmed by real-time RT-PCR of selected genes using the standard ABI/Taqman probe system. These data revealed that, on a molecular level, CASIN treated aged HSCs largely resemble young HSCs.

EXAMPLE 8

In Vivo Rejuvenation of Dermal Tissue

To further assess the effects of in vivo administration of CASIN on aging parameters in the skin, aged mice were treated with CASIN as described in Example 5. The treated and untreated aged and young mice were then tested for skin thickness. The skin of aged mice treated with CASIN exhibited thickness approximately equal to that of young mice. In contrast, the skin of aged, untreated mice exhibited thicknesses that were significantly less than young or CASIN treated aged mice.

EXAMPLE 9

In Vivo Rejuvenation of Dermal Tissue

To further assess the effects of in vivo administration of CASIN on aging parameters in the skin, aged mice are treated with CASIN as described in Example 5. The treated and untreated aged and young mice are then tested for and wound healing, as described below.

When tested for wound healing, the skin of aged mice treated with CASIN respond similarly or nearly identical to the skin of young mice, as described below. In contrast, the skin of aged, untreated mice exhibits impaired wound healing.

On day 28 after initial treatment with CASIN, each mouse is tested with 25 mm oblong full-thickness excision wounds (6 mice of each type per experiment), including the striated muscle layer (*panniculus carnosus*), on the dorsal skin of treated and untreated mice. One day after surgery a clear thin film of dried exudate covers the wounds in both untreated and treated mice. Build-up of dehydrated wound crusts or scabs begin at day 3 and become subsequently more extensive. In the aged, untreated mice, scabs are thicker and extravasation of blood, visible in the gaps within the scabs, is more frequent and extensive than that in the treated mice. In control young mice, and in treated aged mice, loss of wound scabs begins at day 17 and is complete in all mice by day 24 with wounds well-healed and epithelial covering restored. In contrast, the scabs in untreated aged mice start to come off partially around day 14, resulting in a scab with a gaping red wound field, which is evident even at 22 days. Healing of untreated aged mice wounds remains incomplete on day 24, and complete healing in all mice is observed between 25 and 31 days. These experiments indicate that transient treatment (days 1-5) with CASIN causes improved healing of skin wounds.

EXAMPLE 10

Topical Rejuvenation of Dermal Tissue

To further assess the effects of in vivo administration of CASIN on aging parameters in the skin, aged mice are treated with CASIN as described in Example 5. However, instead of intraperitoneal injection, CASIN is administered topically in a formulation designed for non-transdermal use. The treated and untreated aged and young mice are then tested for skin thickness and wound healing. The skin of aged mice topically treated with CASIN exhibits thickness approximately equal to that of young mice. In contrast, the skin of aged, untreated mice exhibits thicknesses that are significantly less than young or topically treated aged mice.

When tested for wound healing, the skin of aged mice topically treated with CASIN respond similarly or nearly identical to the skin of young mice, as described below. In contrast, the skin of aged, untreated mice exhibits impaired wound healing.

EXAMPLE 11

In Vivo Rejuvenation of Intestinal Tissue

To further assess the effects of in vivo administration of CASIN on aging parameters in the intestinal epithelium, aged mice were treated with CASIN as described in Example 5. After 28 days, the mice were sacrificed and intestinal samples were processed for immunohistochemistry, including staining for intestinal stem cell markers Bmi1 and Lgr5.

Intestinal epithelium in aged mice treated with CASIN showed marked improvement in the shape, size and distribution of villi and crypts, compared to untreated aged mice. Staining for stem cell markers indicated a renewed number of stem cells in crypts of treated mice compared to untreated aged mice. The CASIN-treated samples resembled those of young mice much more than the controls, demonstrating the rejuvenating effects of in vivo administration of CASIN on intestinal epithelium, and indicating that those effects persisted long after treatment is discontinued.

EXAMPLE 12

In Vivo Rejuvenation of Intestinal Tissue

CASIN was given at a dose of 2.4 mg/kg twice a day 6 hours apart for 5 days via intraperitoneal injection in both young (10-12 wk old) and aged (22-24 month old) C57BL/6 mice. Aged C57BL/6 mice present with elevated Cdc42 activity in multiple tissues. Weight of the mice was determined in the young and aged control group (no CASIN, just vehicle (PBS/15% Ethanol)) at initiation of the experiment and after 1 week, as well as in the CASIN treated groups (young and aged) at initiation and 1 week after.

Figure 11:
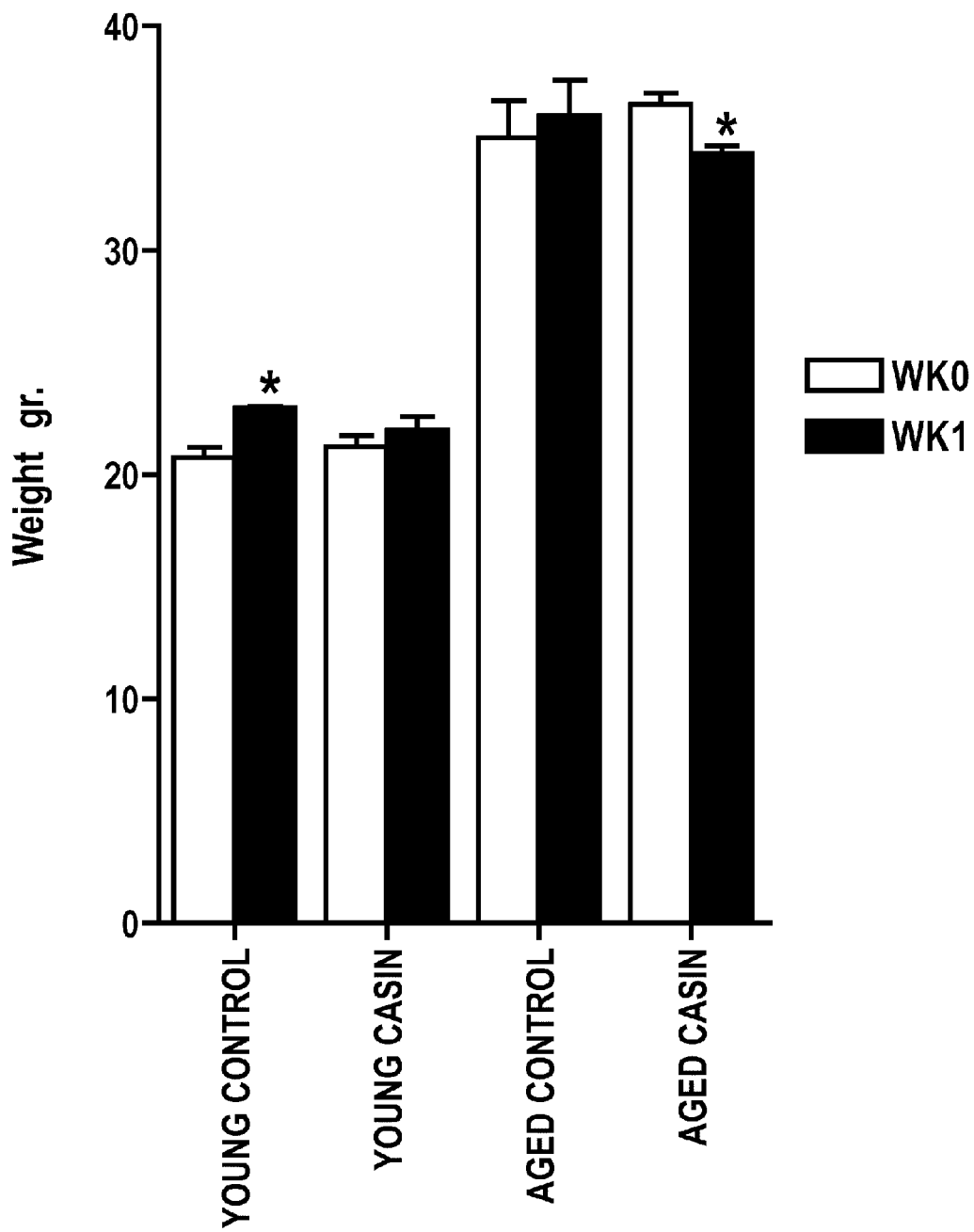
FIG. 11. Weight reduction of mice administered with CASIN was determined Young and aged mice CASIN and control groups were tested for weight gain after 1 week, where only aged CASIN mice demonstrated weight loss.

As shown in FIG. 11, CASIN treatment resulted in a significant reduction in weight in aged animals.

What is claimed is:

1. A method for rejuvenating a blood precursor cell, a dermal epithelial precursor cell or an intestinal epithelial precursor cell in a subject comprising:
   administering to a subject in need of treatment an effective amount of at least one Cdc42-specific inhibitor, wherein the subject is identified as having a blood precursor cell, a dermal epithelial precursor cell or an intestinal epithelial precursor cell with a normalized ratio of GTP-bound Cdc42 to total Cdc42 greater than 1.5 prior to administering said at least one Cdc42-specific inhibitor, and wherein administering the effective amount of the at least one Cdc42-specific inhibitor reduces the normalized ratio of GTP-bound Cdc42 to total Cdc42 in the respective blood precursor cell, dermal epithelial precursor cell or intestinal epithelial precursor cell to a range from about 0.8 to about 1.2, when the normalized ratio of GTP-bound Cdc42 to total Cdc42 is defined as a ratio of GTP-bound Cdc42 to total Cdc42 in an aged cell relative to a ratio of GTP-bound Cdc42 to total Cdc42 in a non-aged cell, and wherein said Cdc42-specific inhibitor comprises a compound of formula (I):

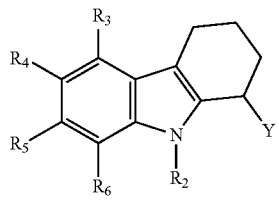

as a single enantiomer, a mixture of enantiomers, pharmaceutically acceptable salt, a solvate, or polymorph thereof, wherein:

Y is selected from the group consisting of —$OR_7$, —$NR_8R_9$, and —$NNR_8R_9$;

$R_7$ is selected from the group consisting of $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl are each optionally substituted with one or more substituents each independently selected from the group consisting of halo, —CN, —OH, $C_{1-6}$ alkoxyl, heteroaryl, $R_{19}$, and —$OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)_uC_{3-7}$cycloalkyl, $C_{2-6}$alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of $R_{21}$ and $R_{22}$, each $R_{21}$ is separately selected from the group consisting of halo, cyano, nitro, and hydroxy, each $R_{22}$ is separately selected from the group consisting of $C_{1-6}$ alkyl, $C_{1-6}$ alkoxy $(CH_2)_uC_{3-7}$ cycloalkyl, $C_{2-6}$ alkenyl, hydroxy-$C_{1-6}$ alkyl, $R_{19}$, and $OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R_2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and $O(CH_2)_u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$, and $R_6$ are each independently selected from the group consisting of hydrogen, halo, cyano, nitro, hydroxy, $C_{1-6}$ alkyl, $(CH_2)_uC_{3-7}$cycloalkyl, $O(CH_2)_u$$C_{3-7}$cycloalkyl, $C_{2-6}$alkenyl, $C_{1-6}$ alkoxy, hydroxyl-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $O(CH_2)_uC_{3-7}$ cycloalkyl, $C_{2-6}$alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

2. A method for rejuvenating a dermal epithelial precursor cell in a subject, wherein the subject is identified as having a blood precursor cell, a dermal epithelial precursor cell or an intestinal epithelial precursor cell with a normalized ratio of GTP-bound Cdc42 to total Cdc42 greater than 1.5 prior to administering said at least one Cdc42-specific inhibitor, and wherein administering the effective amount of the at least one Cdc42-specific inhibitor reduces the normalized ratio of GTP-bound Cdc42 to total Cdc42 in the respective blood precursor cell, dermal epithelial precursor cell or intestinal epithelial precursor cell to a range from about 0.8 to about 1.2, when the normalized ratio of GTP-bound Cdc42 to total Cdc42 is defined as a ratio of GTP-bound Cdc42 to total Cdc42 in an aged cell relative to a ratio of GTP-bound Cdc42 to total Cdc42 in a non-aged cell comprising: administering to a subject in need of treatment an effective amount of at least one Cdc42-specific inhibitor, wherein the effective amount is less than an amount that causes mobilization, and wherein said Cdc42-specific inhibitor comprises a compound of formula (I):

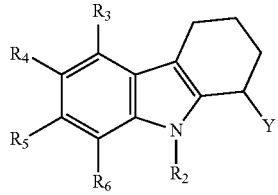

(I)

as a single enantiomer, a mixture of enantiomers, pharmaceutically acceptable salt, a solvate, or polymorph thereof, wherein:

Y is selected from the group consisting of —$OR_7$, —$NR_8R_9$, and —$NNR_8R_9$;

$R_7$ is selected from the group consisting of $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_{2u}C_{3-7}$ cycloalkyl, $C_{2-6}$ alkenyl, $C_{1-6}$ alkoxy, hydroxy-$C_{1-6}$ alkyl, phenyl are each optionally substituted with one or more substitutents each independently selected from the group consisting of halo, —CN, —OH, $C_{1-6}$ alkoxyl, heteroaryl, $R_{19}$, and —$OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ separately from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of and $R_{21}$ and $R_{22}$;

each $R_{21}$ is separately selected from the group consisting of halo, cyano, nitro, and hydroxy, each $R_{22}$ is separately selected from the group consisting of $C_{1-6}$ alkyl, $C_{1-6}$ alkoxy $(CH_2)_uC_{3-7}$ cycloalkyl, $C_{2-6}$ alkenyl, hydroxy-$C_{1-6}$ alkyl, $R_{19}$, and $OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R^2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and $O(CH_2)u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$, and $R_6$ are each independently selected from the group consisting of hydrogen, halo, cyano, nitro, hydroxy, $C_{1-6}$ alkyl, $(CH_2)_uC_{3-7}$cycloalkyl, $O(CH_2)_u$ $C_{3-7}$cycloalkyl, $C_{2-6}$alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $O(CH_2)_uC_{3-7}$ cycloalkyl, $C_{2-6}$alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

3. A method for rejuvenating a blood precursor cell, a dermal epithelial precursor cell or an intestinal epithelial precursor cell in a subject, wherein the subject is identified as having a blood precursor cell, a dermal epithelial precursor cell or an intestinal epithelial precursor cell with a normalized ratio of GTP-bound Cdc42 to total Cdc42 greater than 1.5 prior to administering said at least one Cdc42-specific inhibitor, and wherein administering the effective amount of the at least one Cdc42-specific inhibitor reduces the normalized ratio of GTP-bound Cdc42 to total Cdc42 in the respective blood precursor cell, dermal epithelial precursor cell or intestinal epithelial precursor cell to a range from about 0.8 to about 1.2, when the normalized ratio of GTP-bound Cdc42 to total Cdc42 is defined as a ratio of GTP-bound Cdc42 to total Cdc42 in an aged cell relative to a ratio of GTP-bound Cdc42 to total Cdc42 in a non-aged cell, comprising: administering to a subject in need of treatment an effective amount of at least one Cdc42-specific inhibitor, wherein the effective amount is less than an amount that causes mobilization, and wherein said Cdc42-specific inhibitor comprises a compound of formula (I):

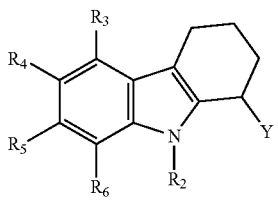

(I)

as a single enantiomer, a mixture of enantiomers, pharmaceutically acceptable salt, a solvate, or polymorph thereof, wherein:

Y is selected from the group consisting of —$OR_7$, —$NR_8R_9$, and —$NNR_8R_9$;

$R_7$ is selected from the group consisting of $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $C_{2-6}$ alkenyl, $C_{1-6}$ alkoxy, hydroxy-$C_{1-6}$ alkyl, phenyl are each optionally substituted with one or more substitutents each independently selected from the group consisting of halo, —CN, —OH, $C_{1-6}$ alkoxyl, heteroaryl, $R_{19}$, and —$OR_{20}$;

$R_8$ and $R_9$ are each separately a hydrogen or $R_{20}$; or $R_8$ and $R_9$ are optionally taken together with the nitrogen to which they are attached to form indolinyl, pyrrolidinyl, piperidinyl, piperazinyl, or morpholinyl, each optionally substituted with one or more substituents each independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro; or $R_8$ and $R_2$ come together to be $C_{1-3}$ alkyl linking together as a ring;

each $R_{20}$ separately selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of $R_{21}$ and $R_{22}$, each $R_{21}$ is separately selected from the group consisting of halo, cyano, nitro, and hydroxy, each $R_{22}$ is separately selected from the group consisting of $C_{1-6}$ alkyl, alkoxy $(CH_2)_uC_{3-7}$ cycloalkyl, $C_{2-6}$ alkenyl, hydroxy-$C_{1-6}$ alkyl, $R_{19}$, and $OR_{20}$, each optionally substituted with one or more substituents each independently selected from the group consisting of halo, cyano, nitro, hydroxy, $C_{1-6}$ alkyl, and $C_{1-6}$ alkoxy;

each u is independently 0, 1, 2, 3, or 4;

$R_2$ is a hydrogen, or selected from the group consisting of $C_{1-6}$ alkyl, $C_{3-7}$ cycloalkyl, and phenyl, said $C_{1-6}$ alkyl, $C_{3-7}$ cycloalkyl, and phenyl, each optionally substituted with one or more substituents each independently selected from the group consisting of halo, cyano, nitro, hydroxy, $C_{1-6}$ alkyl, $(CH_2)_uC_{3-7}$ cycloalkyl $C_{2-6}$ alkenyl, $C_{1-6}$ alkoxy, hydroxy-$C_{1-6}$ alkyl, phenyl, $C_{1-6}$ alkyl substituted with up to 5 fluoro, $C_{1-6}$ alkoxy substituted with up to 5 fluoro, and $O(CH_2)u$phenyl optionally substituted with one or more substituents each independently selected from the group consisting of halo, cyano, nitro, hydroxy, $C_{1-6}$ alkyl, and $C_{1-6}$ alkoxy; or $R_8$ and $R_2$ come together to be $C_{1-3}$ alkyl linking together as a ring;

$R_3$, $R_4$, $R_5$ and $R_6$ are each independently selected from the group consisting of hydrogen, halo, cyano, nitro, hydroxy, $C_{1-6}$ alkyl, $(CH_2)_uC_{3-7}$cycloalkyl, $O(CH_2)_u$ $C_{3-7}$cycloalkyl, $C_{2-6}$alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $O(CH_2)_uC_{3-7}$ cycloalkyl, $C_{2-6}$alkenyl, $C_{1-6}$ alkoxy, hydroxy-$C_{1-6}$ alkyl, and phenyl, each optionally substituted with one or more $R_{23}$, each $R_{23}$ is independently selected from the group consisting of halo, cyano, nitro, hydroxy, $C_{1-6}$ alkyl, $(CH_2)_uC_{3-7}$ cycloalkyl, $C_{2-6}$ alkenyl, $C_{1-6}C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, cyano, nitro, hydroxy, $C_{1-6}$ alkyl, $(CH_2)_uC_{3-7}$ cycloalkyl, $C_{2-6}$alkenyl, $C_{2-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro;

each $R_{19}$ is independently aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro;

each $R_{20}$ is independently hydrogen or aryl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro; and wherein when Y is $NR_8R_9$ then $R_8$ and $R_2$ optionally come together to be $C_{1-3}$ alkyl linking together as a ring, with the proviso when $R_8$ comes together with $R_2$ to be $C_{1-3}$ alkyl linking together as a ring then $R_4$ is not substituted with hydroxyl.

4. The method of claim 1, wherein the blood precursor cell is a hematopoietic cell selected from the group consisting of a progenitor cell and a stem cell.

5. The method of claim 1, wherein the Cdc42-specific inhibitor is CASIN.

6. The method of claim 1 wherein one, two or three of $R_3$, $R_4$, $R_5$ and $R_6$ are not hydrogen.

7. The method of claim 1 wherein $R_4$ is selected from the group consisting of $C_{1-6}$ alkyl, $(CH_2)_uC_{3-7}$cycloalkyl, $O(CH_2)_uC_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $O(CH_2)_uC_{3-7}$ cycloalkyl, $C_{2-6}$ alkenyl, $C_{1-6}$ alkoxy, and phenyl, each optionally substituted with one or more substituents each independently selected from the group consisting of halo $C_{1-6}$ alkyl, $(CH_2)_uC_{3-7}$ cycloalkyl, $C_{2-6}$ alkenyl, $C_{1-6}$ alkoxy, hydroxy-$C_{1-6}$ alkyl, phenyl, $C_{1-6}$ alkyl substituted with up to 5 fluoro, and $C_{1-6}$ alkoxy substituted with up to 5 fluoro.

8. The method of claim 1,
wherein:
Y is $NR_8R_9$,
$R_8$ is hydrogen; and $R_9$ is $C_{1-6}$ alkyl optionally substituted with one or more substituents each independently selected from the group consisting of hydroxy, $R_{19}$ and $OR_{20}$;
each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro, or each $R_{19}$ is independently phenyl optionally substituted with one or more substituents each independently selected from the group consisting of halo, $C_{1-6}$ alkyl, and $C_{1-6}$ alkoxy; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro, or each $R_{20}$ is independently phenyl optionally substituted with one or more substituents each independently selected from the group consisting of halo, $C_{1-6}$ alkyl, and $C_{1-6}$ alkoxy.

9. The method of claim 1, wherein $R_2$ and $R_8$ are hydrogen, or optionally when Y is $NR_8R_9$, $R_8$ and $R_2$ come together to be $C_{1-3}$ alkyl linking together as a ring.

10. The method of claim 1, wherein $R_9$ is hydrogen,
or $R_9$ is $C_{1-6}$ alkyl optionally substituted with one or more substituents each independently selected from the group consisting of hydroxy, $R_{19}$ or $OR_{20}$ where each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and where each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro, or $R_9$ is hydrogen or $C_{1-6}$ alkyl, optionally substituted with one or more substituents each independently selected from the group consisting of hydroxyl, $R_{19}$ and $—OR_{20}$ where each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and where each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

11. The method of claim 1,
wherein $R_4$ is selected from the group consisting of $C_{1-6}$ alkyl, $(CH_2)_uC_{3-7}$cycloalkyl, $O(CH_2)_uC_{3-7}$cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said $C_{1-6}$ alkyl, $(CH_2)_uC_{3-7}$cycloalkyl, $O(CH_2)_uC_{3-7}$cycloalkyl, $C_{1-6}$ alkenyl, $C_{1-6}$ alkoxy, and phenyl, each optionally substituted with one or more R23, each R23 is independently selected from the group consisting of halo, $C_{1-6}$ alkyl, $(CH2)uC3$ 7cycloalkyl, $C_{2-6}$ alkenyl, $C_{1-6}$ alkoxy, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, C1 6 alkyl, $(CH2)uC3$ 7cycloalkyl, $C_{2-6}$ alkenyl, $C_{1-6}$ alkoxy, $C_{1-6}$ alkyl substituted with up to 5 fluoro, and $C_{1-6}$ alkoxy substituted with up to 5 fluoro,
or wherein $R_4$ is selected from the group consisting of $C_{1-6}$ alkyl, C3-7cycloalkyl, OC3 7cycloalkyl, phenyl, $C_{1-6}$ alkyl substituted with up to 5 fluoro, and $C_{1-6}$ alkoxy substituted with up to 5 fluoro, said phenyl optionally substituted with one or more substituents each independently selected from the group consisting of halo, $C_{1-6}$ alkyl,
$C_{1-6}$ alkoxy, $C_{1-6}$ alkyl substituted with up to 5 fluoro, and $C_{1-6}$ alkoxy substituted with up to 5 fluoro.

12. The method of claim 11, wherein Y is $NR_8R_9$ and $R_8$ and $R_2$ come together to be $C_{1-3}$ alkyl linking together as a ring.

13. The method of claim 1, wherein $R_2$ is a hydrogen or selected from the group consisting of $C_{1-6}$ alkyl, $C_{3-7}$ cycloalkyl, and phenyl, said $C_{1-6}$ alkyl optionally substituted with one or more halo.

14. The method of claim 13, wherein R9 is hydrogen, or $C_{1-6}$ alkyl, optionally substituted with one or more substituents each independently selected from the group consisting of hydroxyl, $R_{19}$ and $—OR_{20}$;
each $R_{19}$ is independently phenyl optionally substituted with one or more substituents each independently selected from the group consisting of halo, cyano, $C_{1-6}$ alkyl optionally substituted with up to 5 fluoro, and $C_{1-6}$ alkoxy optionally substituted with up to 5 fluoro; and each $R_{20}$ is independently hydrogen or phenyl optionally substituted with one or more substituents each independently selected from the group consisting of halo, cyano, nitro, hydroxy, $C_{1-6}$ alkyl optionally substituted with up to 5 fluoro, and $C_{1-6}$ alkoxy optionally substituted with up to 5 fluoro.

15. The method of claim 1, wherein the subject has a population of blood precursor cells, dermal epithelial precursor cells or intestinal epithelial precursor cells that exhibit a phenotype typical of an aging cell.

16. The method of claim 2, wherein the topical formulation is a non-transdermal composition.

17. The method of claim 16, wherein the non-transdermal formulation is a matrical or micellar solution, bandage, wound dressing, aerosol spray, foam, non-transdermal topical patch or topical administrative agent.

18. The method of claim 1, wherein the effective amount of Cdc42-specific inhibitor is sufficient to reduce the relative level of GTP-bound Cdc42 in an aged cell.

* * * * *